US012723042B2

(12) United States Patent
Xiang et al.

(10) Patent No.: US 12,723,042 B2
(45) Date of Patent: Sep. 1, 2026

(54) CRYSTAL FORM AND SALT FORM OF FIVE-MEMBERED-FUSED SIX-MEMBERED COMPOUND, PREPARATION METHOD, PHARMACEUTICAL COMPOSITION, AND USE

(71) Applicant: HANGZHOU POLYMED BIOPHARMACEUTICALS, INC., Hangzhou (CN)

(72) Inventors: Jason Shaoyun Xiang, Hangzhou (CN); Lei Wu, Hangzhou (CN)

(73) Assignee: HANGZHOU POLYMED BIOPHARMACEUTICALS, INC., Hangzhou (CN)

(*) Notice: Subject to any disclaimer, the term of this patent is extended or adjusted under 35 U.S.C. 154(b) by 0 days.

(21) Appl. No.: 19/257,024

(22) Filed: Jul. 1, 2025

(65) Prior Publication Data

US 2026/0008776 A1 Jan. 8, 2026

Related U.S. Application Data

(63) Continuation of application No. PCT/CN2024/100322, filed on Jun. 20, 2024.

(30) Foreign Application Priority Data

| | | |
|---|---|---|
| Jun. 21, 2023 | (CN) | 202310744684.5 |
| Jun. 21, 2023 | (CN) | 202310746259.X |
| Jun. 21, 2023 | (CN) | 202310748384.4 |
| Jun. 21, 2023 | (CN) | 202310748633.X |
| Jun. 12, 2024 | (CN) | 202410756994.3 |

(51) Int. Cl.
*C07D 413/14* (2006.01)
*A61K 31/4439* (2006.01)

(52) U.S. Cl.
CPC ........ *C07D 413/14* (2013.01); *A61K 31/4439* (2013.01)

(58) Field of Classification Search
CPC .. C07D 413/14; C07D 401/14; C07D 417/14; C07D 471/04; C07D 519/00; A61K 31/4439; A61K 31/444; A61K 31/4545
See application file for complete search history.

(56) References Cited

U.S. PATENT DOCUMENTS

| | | | |
|---|---|---|---|
| 12,195,479 | B2 | 1/2025 | Xiang et al. |
| 2024/0132473 | A1 | 4/2024 | Wei et al. |

FOREIGN PATENT DOCUMENTS

| | | | |
|---|---|---|---|
| CN | 112480101 A | 3/2021 | |
| CN | 113278017 A | 8/2021 | |
| CN | 118530221 A | 8/2024 | |
| WO | 2022216379 A1 | 10/2022 | |

OTHER PUBLICATIONS

Jan. 27, 2026 First Office Action issued in Chinese Patent Application No. 202480005401.8.
Jan. 23, 2026 Search Report issued in Chinese Patent Application No. 202480005401.8.
Sep. 16, 2024 International Search Report issued in International Patent Application No. PCT/CN2024/100322. (9 pages).
Sep. 16, 2024 Written Opinion of the International Searching Authority issued in International Patent Application No. PCT/CN2024/100322. (12 pages).
Zhai, Wenqiang et al., "Discovery and Optimization of a Potent and Selective Indazolamine Series of IRAK4 Inhibitors" Bioorganic & Medicinal Chemistry Letters, vol. 31, Nov. 24, 2020, p. 127686, figure 1, and supplementary information. (6 pages).
Kiyoi, Hitoshi et al., "FLT3 mutations in acute myeloid leukemia: Therapeutic paradigm beyond inhibitor development", Cancer Science, Feb. 2020; 111(2): 312-322 (11 pages).
Daver, Naval et al., "Targeting FLT3 mutations in AML: review of current knowledge and evidence" Leukemia, Molecular targets for therapy, Feb. 2019; 33(2): 299-312 (14 pages).
Gummadi, V.R. et al., "Discovery of CA-4948, an Orally Bioavailable IRAK4 Inhibitor for Treatment of Hematologic Malignancies" ACS Medicinal Chemistry Letters, Oct. 14, 2020; 11(12): 2374-2381 (8 pages).

(Continued)

*Primary Examiner* — Sahar Javanmard
(74) *Attorney, Agent, or Firm* — Rothwell, Figg, Ernst & Manbeck, P.C.

(57) ABSTRACT

A crystal form and salt form of a five- and six-membered compound, a preparation method therefor, a pharmaceutical composition thereof, and a use thereof are disclosed. Specifically, a crystal form and salt form of a five-membered-fused six-membered compound as shown in formula I, a preparation method therefor, a pharmaceutical composition thereof, and a use thereof are disclosed. The crystal form and salt form of the compound have an inhibitory effect on FLT3 and/or IRAK4. The crystal form has a high single melt point, is thermodynamically stable, and has high crystallinity. The crystal form represents good physical and chemical stability under strong illumination, high temperature and high humidity conditions, and the crystal form has weak hygroscopicity.

(I)

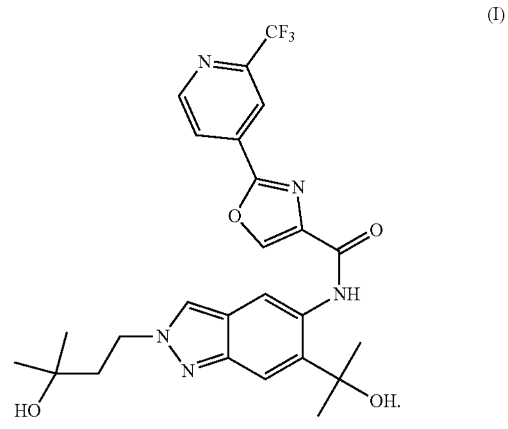

20 Claims, 18 Drawing Sheets

(56) References Cited

OTHER PUBLICATIONS

Rabik, C.A. et al., FLT3-IRAK dual targeting: an exciting new therapeutic option guided by adaptive activation of immune response pathways, Annals of Translational Medicine, Apr. 2020; 8(7): 511 (3 pages).

CRYSTAL FORM AND SALT FORM OF FIVE-MEMBERED-FUSED SIX-MEMBERED COMPOUND, PREPARATION METHOD, PHARMACEUTICAL COMPOSITION, AND USE

CROSS-REFERENCE TO RELATED APPLICATIONS

This application is a continuation application of PCT/CN2024/100322, filed on Jun. 20, 2024, which claims the right of the priorities of Chinese patent application 202310748384.4 filed on Jun. 21, 2023, Chinese patent application 202310744684.5 filed on Jun. 21, 2023, Chinese patent application 202310748633.X filed on Jun. 21, 2023, Chinese patent application 202310746259.X filed on Jun. 21, 2023, and Chinese patent application 202410756994.3 filed on Jun. 12, 2024, the contents of which are incorporated herein by reference in their entireties.

TECHNICAL FIELD

The present disclosure relates to a crystal form, salt form, preparation method, pharmaceutical composition, and use of a five-membered-fused six-membered compound.

BACKGROUND

FMS-like tyrosine kinase 3 (FLT3) is a type III receptor tyrosine kinase, and its mutation is one of the most common genetic alterations and poor prognostic factors in patients with acute myeloid leukemia (AML). The main types of FLT3 mutations are internal tandem duplication mutations in the juxtamembrane domain (FLT3-ITD) and point mutations or deletions in the tyrosine kinase domain (FLT3-TKD), accounting for about 30% of AML patients (Kiyoi H, Kawashima N, Ishikawa Y. *FLT3 mutations in acute myeloid leukemia: Therapeutic paradigm beyond inhibitor development*. Cancer Sci. 2020 February; 111(2): 312-322). Activated FLT3 induces abnormalities in multiple intracellular signaling pathways (such as RAS, PI3K, and STAT5), leading to the survival, proliferation, differentiation, and anti-apoptosis of hematopoietic cells. Furthermore, the mutant-wild-type allele ratio, insertion site, ITD length, karyotype, and presence of NPM1 gene mutations can influence the prognostic effect of FLT3-ITD in newly diagnosed FLT3-ITD-mutated AML patients (Daver N, Schlenk R F, Russell N H, Levis M J. *Targeting FLT3 mutations in AML: review of current knowledge and evidence*. Leukemia. 2019 February; 33(2): 299-312. Doi: 10.1038/s41375-018-0357-9.). Since high-dose chemotherapy and allogeneic hematopoietic stem cell transplantation cannot fully improve the prognosis, patients have a short survival period and are prone to relapse. Therefore, FLT3 kinase inhibitors have become a research hotspot for the treatment of AML. The first-generation FLT3 inhibitors are broad-spectrum inhibitors, such as Lestaurtinib, Sunitinib, Sorafenib, Ponatinib, and Midostaurin, which can inhibit multiple kinases. However, their efficacy is poor, and no clear efficacy is observed when used in combination with chemical drugs, and their toxicity is significantly increased. For example, Midostaurin is not effective as a monotherapy, but when combined with Cytarabine, Daunorubicin, and Cytarabine (FDA approved), it can be used to treat FLT3-mutated AML in adults. Second-generation FLT3 kinase inhibitors such as Gilteritinib, Crenolanib, and Quizartinib are more selective, more active, and less toxic, but still have some off-target effects.

Currently, three FLT3 inhibitors (Quizartinib, Gilteritinib, Midostaurin) have been approved for marketing in Japan and/or the United States for monotherapy or combination therapy with conventional chemotherapeutic agents in AML patients. These inhibitors have shown good therapeutic responses in clinical practice and have improved the prognosis of AML patients to some extent. When used as a monotherapy, the disease relapses rapidly, with both target-dependent and non-target-dependent drug resistance already having emerged. Target-dependent mutations commonly occur in the activation loop (such as aspartate 835, D835) and gatekeeper residues (such as phenylalanine 691, F691), with D835 mutation being the most common target-dependent drug resistance mutation site. Activation of related signaling pathways can also compensate for the inhibition of the FLT3 signaling pathway. Currently, researchers have reduced the proportion of non-target drug resistance by directly inhibiting related signaling pathways (such as PI3K/AKT and/or RAS/MEK/MAPK) or jointly inhibiting cell survival-related signaling pathways through combination therapy, but the effect is still limited (Rabik C A, Wang J, Pratilas C A. *FLT3-IRAK dual targeting: an exciting new therapeutic option guided by adaptive activation of immune response pathways*. Ann Transl Med. 2020 April; 8(7): 511.). After a period of administration of Quizartinib and Gilteritinib, although the expression of pFLT3 and pSTAT5 was reduced, no obvious inhibition of tumor cells was observed. In recurrent cases, the phosphorylation level of IRAK4 was increased in most cases. When combined with IRAK4 inhibitors, the survival rate of tumor cells was reduced, suggesting that IRAK4 can be used as a non-target drug resistance target.

Interleukin-1 receptor-associated kinases (IRAKs) are serine/threonine protein kinases belonging to the tyrosine-like kinase (TLK) family, with IRAK1 and IRAK4 having kinase activity. IRAKs are located downstream of the toll-like receptor and IL-1R pathways and play an important role in innate immune signal transduction. TLR stimulation can recruit MYD88 and activate the receptor complex, which then forms a complex with IRAK4 to subsequently activate IRAK1. Subsequently, TRAF6 is activated by IRAK1, leading to NF-kB activation. Abnormal activation of the IRAK pathway in tumor cells can further promote disease progression through inflammatory responses in the tumor microenvironment (Gummadi V R, Boruah A, Ainan B R, Vare B R, Manda S, Gondle H P, Kumar S N, Mukherjee S, Gore S T, Krishnamurthy N R, Marappan S, Nayak S S, Nellore K, Balasubramanian W R, Bhumireddy A, Gir S, Gopinath S, Samiulla D S, Daginakatte G, Basavaraju A, Chelur S, Eswarappa R, Belliappa C, Subramanya H S, Booher R N, Ramachandra M, Samajdar S. *Discovery of CA-4948, an Orally Bioavailable IRAK4 Inhibitor for Treatment of Hematologic Malignancies*. ACS Med Chem Lett. 2020 Oct. 14; 11(12): 2374-2381.). The development of a FLT3/IRAK4 dual-target compound with potential clinical application value is expected to improve patient prognosis and reduce the possibility of drug resistance.

BRIEF SUMMARY OF THE INVENTION

The present disclosure provides a crystal form, salt form, preparation method, pharmaceutical composition, and use of a five-membered-fused six-membered compound. The crystal forms and salt forms of the compound of the present disclosure exhibit inhibitory effects on FLT3 and/or IRAK4, demonstrating potential clinical application value with expectations to improve patient prognosis and reduce the possibility of drug resistance.

The present disclosure provides a crystal form A of a five-membered-fused six-membered compound represented by formula I, which has an X-ray powder diffraction pattern expressed by 2θ angles comprising characteristic peaks at 13.12±0.20°, 19.05±0.20°, 25.85±0.20°, and 26.73±0.20°;

I

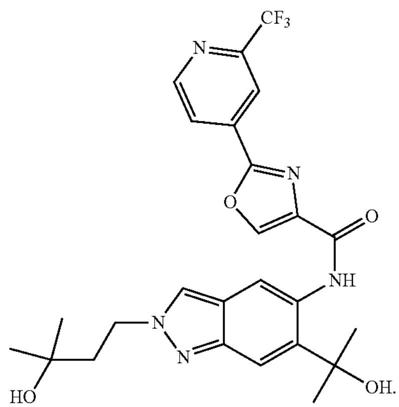

In some embodiments of the present disclosure, the X-ray powder diffraction pattern is measured using Cu—Kα radiation spectral line.

In some embodiments of the present disclosure, the crystal form A has an X-ray powder diffraction pattern expressed by 2θ angles further comprising characteristic peaks at one or more of 7.84±0.20°, 10.25±0.20°, 20.96±0.20°, and 24.46±0.20°.

In some embodiments of the present disclosure, the crystal form A has an X-ray powder diffraction pattern expressed by 2θ angles comprising characteristic peaks at 7.84±0.20°, 10.25±0.20°, 13.12±0.20°, 19.05±0.20°, 20.96±0.20°, 24.46±0.20°, 25.85±0.20°, and 26.73±0.20°.

The present disclosure provides a crystal form A of a five-membered-fused six-membered compound represented by formula I, which has an X-ray powder diffraction pattern expressed by 2θ angles comprising characteristic peaks at 7.84±0.20°, 10.25±0.20°, 20.96±0.20°, 22.36±0.20°, and 25.85±0.20°;

I

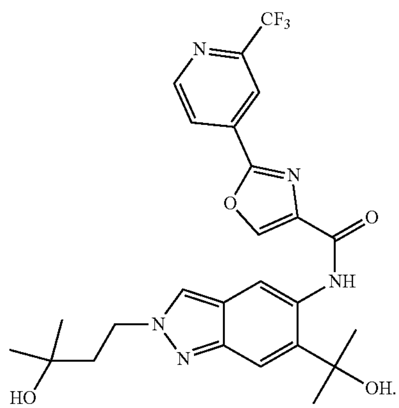

The crystal form A has an X-ray powder diffraction pattern expressed by 2θ angles further comprising characteristic peaks at one or more of 11.33±0.20°, 13.12±0.20°, 14.43±0.20°, 15.52±0.20°, 16.78±0.20°, 17.55±0.20°, 20.77±0.20°, 22.92±0.20°, and 24.46±0.20°.

In some embodiments of the present disclosure, the crystal form A has an X-ray powder diffraction pattern expressed by 2θ angles comprising diffraction peaks at the diffraction angles shown in the following table:

| Number | 2θ Angle/° |
|---|---|
| 1 | 7.84 |
| 2 | 7.99 |
| 3 | 10.25 |
| 4 | 11.33 |
| 5 | 12.21 |
| 6 | 13.12 |
| 7 | 14.43 |
| 8 | 14.71 |
| 9 | 15.52 |
| 10 | 15.67 |
| 11 | 16.18 |
| 12 | 16.36 |
| 13 | 16.57 |
| 14 | 16.78 |
| 15 | 17.19 |
| 16 | 17.55 |
| 17 | 17.90 |
| 18 | 18.25 |
| 19 | 18.70 |
| 20 | 19.05 |
| 21 | 20.21 |
| 22 | 20.44 |
| 23 | 20.77 |
| 24 | 20.96 |
| 25 | 21.32 |
| 26 | 21.66 |
| 27 | 22.36 |
| 28 | 22.60 |
| 29 | 22.92 |
| 30 | 23.15 |
| 31 | 23.44 |
| 32 | 24.01 |
| 33 | 24.46 |
| 34 | 24.71 |
| 35 | 25.45 |
| 36 | 25.85 |
| 37 | 26.08 |
| 38 | 26.73 |
| 39 | 26.92 |
| 40 | 27.08 |
| 41 | 27.47 |
| 42 | 28.33 |
| 43 | 29.29 |
| 44 | 29.46 |
| 45 | 29.64 |
| 46 | 31.45 |
| 47 | 31.64 |
| 48 | 32.28 |
| 49 | 32.54 |
| 50 | 33.31 |
| 51 | 33.64 |
| 52 | 33.96 |
| 53 | 36.97 |
| 54 | 37.35 |
| 55 | 37.58 |
| 56 | 37.73 |
| 57 | 38.31 |
| 58 | 38.70 |
| 59 | 39.05 |
| 60 | 39.27 |
| 61 | 39.77. |

In some embodiments of the present disclosure, diffraction peaks, d-spacing values, and relative intensities of the X-ray powder diffraction pattern of the crystal form A expressed by 2θ angles are shown in the following table:

| Number | 2θ Angle/° | d-Spacing/Å | Relative Intensity/% |
|---|---|---|---|
| 1 | 7.84 | 11.26 | 7.65 |
| 2 | 7.99 | 11.05 | 1.77 |
| 3 | 10.25 | 8.62 | 100 |
| 4 | 11.33 | 7.81 | 16.8 |
| 5 | 12.21 | 7.25 | 2.33 |
| 6 | 13.12 | 6.74 | 16.23 |
| 7 | 14.43 | 6.13 | 12.33 |
| 8 | 14.71 | 6.02 | 2.99 |
| 9 | 15.52 | 5.71 | 20.12 |
| 10 | 15.67 | 5.65 | 12.49 |
| 11 | 16.18 | 5.47 | 5.78 |
| 12 | 16.36 | 5.41) | 6.35 |
| 13 | 16.57 | 5.35 | 5.12 |
| 14 | 16.78 | 5.28 | 40.76 |
| 15 | 17.19 | 5.17 | 1.32 |
| 16 | 17.55 | 5.05 | 20.29 |
| 17 | 17.90 | 4.95 | 3.05 |
| 18 | 18.25 | 4.86 | 4.03 |
| 19 | 18.70 | 4.74 | 4.79 |
| 20 | 19.05 | 4.66 | 4.17 |
| 21 | 20.21 | 4.39 | 3 |
| 22 | 20.44 | 4.34 | 6.18 |
| 23 | 20.77 | 4.27 | 28.56 |
| 24 | 20.96 | 4.24 | 43.1 |
| 25 | 21.32 | 4.16 | 7.24 |
| 26 | 21.66 | 4.10 | 3.96 |
| 27 | 22.36 | 3.97 | 41.38 |
| 28 | 22.60 | 3.93 | 3.14 |
| 29 | 22.92 | 3.88 | 33.80 |
| 30 | 23.15 | 3.84 | 6.25 |
| 31 | 23.44 | 3.79 | 1.38 |
| 32 | 24.01 | 3.70 | 13.70 |
| 33 | 24.46 | 3.63 | 25.66 |
| 34 | 24.71 | 3.60 | 3.71 |
| 35 | 25.45 | 3.50 | 5.37 |
| 36 | 25.85 | 3.44 | 49.49 |
| 37 | 26.08 | 3.41 | 7.69 |
| 38 | 26.73 | 3.33 | 11.86 |
| 39 | 26.92 | 3.31 | 1.04 |
| 40 | 27.08 | 3.29 | 1.92 |
| 41 | 27.47 | 3.24 | 1.07 |
| 42 | 28.33 | 3.15 | 7.54 |
| 43 | 29.29 | 3.05 | 3.02 |
| 44 | 29.46 | 3.03 | 5.97 |
| 45 | 29.64 | 3.01 | 2.03 |
| 46 | 31.45 | 2.84 | 1.99 |
| 47 | 31.64 | 2.83 | 2.59 |
| 48 | 32.28 | 2.77 | 3.79 |
| 49 | 32.54 | 2.75 | 5.94 |
| 50 | 33.31 | 2.69 | 1.44 |
| 51 | 33.64 | 2.66 | 3.15 |
| 52 | 33.96 | 2.64 | 4.50 |
| 53 | 36.97 | 2.43 | 1.35 |
| 54 | 37.35 | 2.41 | 3.94 |
| 55 | 37.58 | 2.39 | 0.61 |
| 56 | 37.73 | 2.38 | 2.33 |
| 57 | 38.31 | 2.35 | 1.34 |
| 58 | 38.70 | 2.33 | 0.4 |
| 59 | 39.05 | 2.30 | 4.73 |
| 60 | 39.27 | 2.29 | 1.37 |
| 61 | 39.77 | 2.26 | 0.20. |

In some embodiments of the present disclosure, the X-ray powder diffraction (XRPD) pattern of the crystal form A is substantially as shown in FIG. 1.

In some embodiments of the present disclosure, the crystal form A has a differential scanning calorimetry analysis pattern showing an onset of an endothermic peak at 231.31±2° C., and further reaches a peak value of the endothermic peak at 232.04±2° C.; and even further has an enthalpy value of 111.300 J/g.

In some embodiments of the present disclosure, the crystal form A has a differential scanning calorimetry analysis pattern showing an onset of an endothermic peak at 237.74±2° C., and further reaches a peak value of the endothermic peak at 244.16±2° C.; and even further has an enthalpy value of 69.104 J/g.

In some embodiments of the present disclosure, the differential scanning calorimetry (DSC) analysis pattern of the crystal form A is substantially as shown in FIG. 2.

In some embodiments of the present disclosure, the crystal form A has a thermal gravimetric analysis pattern showing a weight loss of 0.428% at 200° C.; the "%" represents mass percentage.

In some embodiments of the present disclosure, the thermal gravimetric analysis (TGA) pattern of the crystal form A is substantially as shown in FIG. 2.

The present disclosure provides a crystal form C of a five-membered-fused six-membered compound represented by formula I, which has an X-ray powder diffraction pattern expressed by 2θ angles comprising characteristic peaks at 11.05±0.20°, 14.21±0.20°, 18.83±0.20°, and 28.80±0.20°;

I

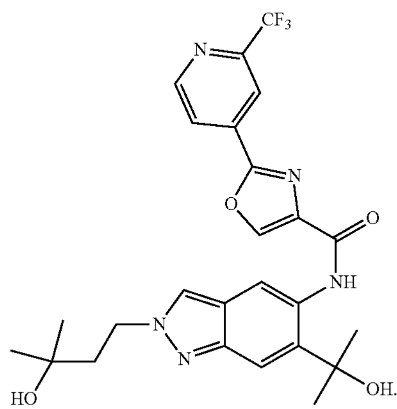

In some embodiments of the present disclosure, the crystal form C has an X-ray powder diffraction pattern expressed by 2θ angles further comprising characteristic peaks at one or more of 7.02±0.20°, 9.78±0.20°, 20.44±0.20°, and 23.98±0.20°.

In some embodiments of the present disclosure, the crystal form C has an X-ray powder diffraction pattern expressed by 2θ angles comprising characteristic peaks at 7.02±0.20°, 9.78±0.20°, 11.05±0.20°, 14.21±0.20°, 18.83±0.20°, 20.44±0.20°, 23.98±0.20°, and 28.80±0.20°.

The present disclosure provides a crystal form C of a five-membered-fused six-membered compound represented by formula I, which has an X-ray powder diffraction pattern expressed by 2θ angles comprising characteristic peaks at 7.02±0.20°, 9.78±0.20°, 11.05±0.20°, 14.21±0.20°, 18.83±0.20°, and 20.44±0.20°;

I

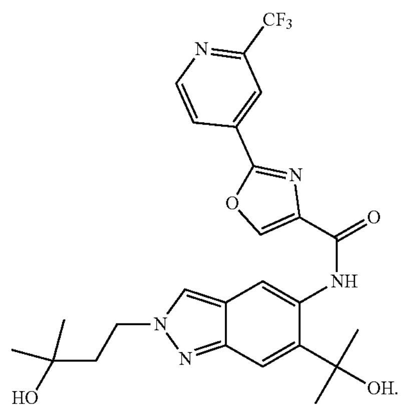

In some embodiments of the present disclosure, the crystal form C has an X-ray powder diffraction pattern expressed by 2θ angles further comprising characteristic peaks at one or more of 11.59±0.20°, 18.19±0.20°, 21.17±0.20°, 22.87±0.20°, 23.98±0.20°, 24.19±0.20°, 25.71±0.20°, and 28.80±0.20°.

In some embodiments of the present disclosure, the crystal form C has an X-ray powder diffraction pattern expressed by 2θ angles comprising diffraction peaks at the diffraction angles shown in the following table:

| Number | 2θ Angle/° |
|---|---|
| 1 | 7.02 |
| 2 | 9.78 |
| 3 | 10.19 |
| 4 | 11.05 |
| 5 | 11.31 |
| 6 | 11.59 |
| 7 | 12.53 |
| 8 | 13.85 |
| 9 | 14.21 |
| 10 | 14.41 |
| 11 | 15.20 |
| 12 | 15.37 |
| 13 | 15.75 |
| 14 | 16.17 |
| 15 | 16.60 |
| 16 | 17.97 |
| 17 | 18.19 |
| 18 | 18.83 |
| 19 | 19.79 |
| 20 | 20.00 |
| 21 | 20.44 |
| 22 | 21.17 |
| 23 | 22.13 |
| 24 | 22.37 |
| 25 | 22.87 |
| 26 | 23.43 |
| 27 | 23.66 |
| 28 | 23.98 |
| 29 | 24.19 |
| 30 | 25.47 |
| 31 | 25.71 |
| 32 | 25.87 |
| 33 | 26.77 |
| 34 | 27.00 |
| 35 | 27.44 |
| 36 | 27.78 |
| 37 | 28.06 |
| 38 | 28.80 |
| 39 | 29.19 |
| 40 | 29.39 |
| 41 | 30.84 |
| 42 | 31.60 |

-continued

| Number | 2θ Angle/° |
|---|---|
| 43 | 32.85 |
| 44 | 33.40 |
| 45 | 33.99 |
| 46 | 34.43 |
| 47 | 35.89 |
| 48 | 36.64 |
| 49 | 36.99 |
| 50 | 37.41 |
| 51 | 38.41 |
| 52 | 38.57. |

In some embodiments of the present disclosure, diffraction peaks, d-spacing values, and relative intensities of the X-ray powder diffraction pattern of the crystal form C expressed by 2θ angles are shown in the following table:

| Number | 2θ Angle/° | d-Spacing/Å | Relative Intensity/% |
|---|---|---|---|
| 1 | 7.02 | 12.58 | 64.32 |
| 2 | 9.78 | 9.03 | 73.15 |
| 3 | 10.19 | 8.67 | 9.94 |
| 4 | 11.05 | 8.00 | 100.00 |
| 5 | 11.31 | 7.82 | 4.23 |
| 6 | 11.59 | 7.63 | 22.75 |
| 7 | 12.53 | 7.06 | 2.07 |
| 8 | 13.85 | 6.39 | 2.37 |
| 9 | 14.21 | 6.23 | 62.08 |
| 10 | 14.41 | 6.14 | 9.66 |
| 11 | 15.20 | 5.82 | 5.14 |
| 12 | 15.37 | 5.76 | 3.46 |
| 13 | 15.75 | 5.62 | 5.39 |
| 14 | 16.17 | 5.48 | 3.06 |
| 15 | 16.60 | 5.34 | 12.13 |
| 16 | 17.97 | 4.93 | 16.96 |
| 17 | 18.19 | 4.87 | 44.30 |
| 18 | 18.83 | 4.71 | 96.60 |
| 19 | 19.79 | 4.48 | 3.93 |
| 20 | 20.00 | 4.44 | 16.90 |
| 21 | 20.44 | 4.34 | 78.81 |
| 22 | 21.17 | 4.19 | 20.65 |
| 23 | 22.13 | 4.01 | 8.72 |
| 24 | 22.37 | 3.97 | 12.57 |
| 25 | 22.87 | 3.88 | 20.69 |
| 26 | 23.43 | 3.79 | 3.29 |
| 27 | 23.66 | 3.76 | 8.82 |
| 28 | 23.98 | 3.71 | 34.12 |
| 29 | 24.19 | 3.68 | 23.56 |
| 30 | 25.47 | 3.49 | 13.34 |
| 31 | 25.71 | 3.46 | 41.53 |
| 32 | 25.87 | 3.44 | 5.23 |
| 33 | 26.77 | 3.33 | 9.59 |
| 34 | 27.00 | 3.30 | 15.36 |
| 35 | 27.44 | 3.25 | 2.73 |
| 36 | 27.78 | 3.21 | 2.25 |
| 37 | 28.06 | 3.18 | 12.60 |
| 38 | 28.80 | 3.10 | 33.97 |
| 39 | 29.19 | 3.06 | 3.30 |
| 40 | 29.39 | 3.04 | 2.64 |
| 41 | 30.84 | 2.90 | 2.14 |
| 42 | 31.60 | 2.83 | 1.63 |
| 43 | 32.85 | 2.73 | 9.80 |
| 44 | 33.40 | 2.68 | 1.73 |
| 45 | 33.99 | 2.64 | 2.62 |
| 46 | 34.43 | 2.60 | 2.87 |
| 47 | 35.89 | 2.50 | 1.58 |
| 48 | 36.64 | 2.45 | 11.29 |
| 49 | 36.99 | 2.43 | 7.51 |
| 50 | 37.41 | 2.40 | 1.77 |
| 51 | 38.41 | 2.34 | 10.89 |
| 52 | 38.57 | 2.33 | 10.28. |

In some embodiments of the present disclosure, the X-ray powder diffraction (XRPD) pattern of the crystal form C is substantially as shown in FIG. 5.

In some embodiments of the present disclosure, the crystal form C has a differential scanning calorimetry analysis pattern showing an onset of an endothermic peak at 63.69±2° C., and further reaches a peak value of the endothermic peak at 82.10±2° C.; and even further has an enthalpy value of 61.396 J/g.

In some embodiments of the present disclosure, the crystal form C has a differential scanning calorimetry analysis pattern showing an onset of an endothermic peak at 126.27±2° C., and further reaches a peak value of the endothermic peak at 134.20±2° C.; and even further has an enthalpy value of 42.089 J/g.

In some embodiments of the present disclosure, the crystal form C has a differential scanning calorimetry analysis pattern showing an onset of an endothermic peak at 230.61±2° C., and further reaches a peak value of the endothermic peak at 231.73±2° C.; and even further has an enthalpy value of 103.46 J/g.

In some embodiments of the present disclosure, the differential scanning calorimetry (DSC) analysis pattern of the crystal form C is substantially as shown in FIG. 6.

In some embodiments of the present disclosure, the crystal form C has a thermal gravimetric analysis pattern showing a weight loss of 3.778% at 73.91° C.; the "%" represents mass percentage.

In some embodiments of the present disclosure, the thermal gravimetric analysis (TGA) pattern of the crystal form C is substantially as shown in FIG. 6.

The present disclosure provides a crystal form B of a five-membered-fused six-membered compound represented by formula I, which has an X-ray powder diffraction pattern expressed by 2θ angles comprising characteristic peaks at 9.94±0.20°, 11.81±0.20°, 16.26±0.20°, and 18.47±0.20°;

I

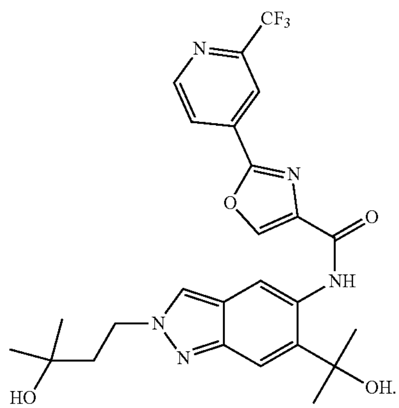

In some embodiments of the present disclosure, the crystal form B has an X-ray powder diffraction pattern expressed by 2θ angles further comprising characteristic peaks at one or more of 11.41±0.20°, 14.41±0.20°, 20.73±0.20°, and 23.39±0.20°.

In some embodiments of the present disclosure, the crystal form B has an X-ray powder diffraction pattern expressed by 2θ angles comprising characteristic peaks at 9.94±0.20°, 11.41±0.20°, 11.81±0.20°, 14.41±0.20°, 16.26±0.20°, 18.47±0.20°, 20.73±0.20°, and 23.39±0.20°.

In some embodiments of the present disclosure, the crystal form B has an X-ray powder diffraction pattern expressed by 2θ angles comprising diffraction peaks at the diffraction angles shown in the following table:

| Number | 2θ Angle/° |
|---|---|
| 1 | 7.12 |
| 2 | 9.94 |
| 3 | 10.24 |
| 4 | 11.20 |
| 5 | 11.41 |
| 6 | 11.81 |
| 7 | 12.36 |
| 8 | 14.42 |
| 9 | 15.89 |
| 10 | 16.26 |
| 11 | 17.01 |
| 12 | 18.18 |
| 13 | 18.47 |
| 14 | 19.25 |
| 15 | 20.12 |
| 16 | 20.31 |
| 17 | 20.73 |
| 18 | 22.45 |
| 19 | 23.15 |
| 20 | 23.39 |
| 21 | 24.85 |
| 22 | 25.26 |
| 23 | 26.52 |
| 24 | 27.38 |
| 25 | 27.89 |
| 26 | 28.21 |
| 27 | 28.48 |
| 28 | 30.33 |
| 29 | 30.91 |
| 30 | 31.37 |
| 31 | 32.97 |
| 32 | 33.23 |
| 33 | 34.44 |
| 34 | 34.74 |
| 35 | 35.08 |
| 36 | 37.79. |

In some embodiments of the present disclosure, diffraction peaks, d-spacing values, and relative intensities of the X-ray powder diffraction pattern of the crystal form B expressed by 2θ angles are shown in the following table:

| Number | 2θ Angle/° | d-Spacing/Å | Relative Intensity/% |
|---|---|---|---|
| 1 | 7.12 | 12.40 | 16.52 |
| 2 | 9.94 | 8.89 | 74.06 |
| 3 | 10.24 | 8.63 | 10.16 |
| 4 | 11.20 | 7.89 | 31.34 |
| 5 | 11.41 | 7.75 | 42.69 |
| 6 | 11.81 | 7.49 | 12.75 |
| 7 | 12.36 | 7.16 | 2.61 |
| 8 | 14.42 | 6.14 | 55.24 |
| 9 | 15.89 | 5.57 | 36.43 |
| 10 | 16.26 | 5.45 | 25.97 |
| 11 | 17.01 | 5.21 | 4.16 |
| 12 | 18.18 | 4.88 | 14.48 |
| 13 | 18.47 | 4.80 | 27.34 |
| 14 | 19.25 | 4.61 | 28.04 |
| 15 | 20.12 | 4.41 | 12.85 |
| 16 | 20.31 | 4.37 | 15.69 |
| 17 | 20.73 | 4.28 | 100.00 |
| 18 | 22.45 | 3.96 | 6.45 |
| 19 | 23.15 | 3.84 | 13.45 |
| 20 | 23.39 | 3.80 | 85.19 |
| 21 | 24.85 | 3.58 | 10.82 |
| 22 | 25.26 | 3.52 | 14.37 |
| 23 | 26.52 | 3.36 | 5.76 |
| 24 | 27.38 | 3.26 | 17.04 |
| 25 | 27.89 | 3.20 | 17.16 |
| 26 | 28.21 | 3.16 | 22.03 |
| 27 | 28.48 | 3.13 | 6.27 |
| 28 | 30.33 | 2.94 | 8.00 |
| 29 | 30.91 | 2.89 | 1.94 |
| 30 | 31.37 | 2.85 | 6.16 |
| 31 | 32.97 | 2.71 | 5.78 |
| 32 | 33.23 | 2.69 | 11.97 |

-continued

| Number | 2θ Angle/° | d-Spacing/Å | Relative Intensity/% |
|---|---|---|---|
| 33 | 34.44 | 2.60 | 5.97 |
| 34 | 34.74 | 2.58 | 1.19 |
| 35 | 35.08 | 2.56 | 6.45 |
| 36 | 37.79 | 2.38 | 6.74. |

In some embodiments of the present disclosure, the X-ray powder diffraction (XRPD) pattern of the crystal form B is substantially as shown in FIG. 3.

In some embodiments of the present disclosure, the crystal form B has a differential scanning calorimetry analysis pattern showing an onset of an endothermic peak at 60.85±2° C., and further reaches a peak value of the endothermic peak at 72.84±2° C.; and even further has an enthalpy value of 32.752 J/g.

In some embodiments of the present disclosure, the crystal form B has a differential scanning calorimetry analysis pattern showing an onset of an endothermic peak at 151.04±2° C., and further reaches a peak value of the endothermic peak at 153.19±2° C.; and even further has an enthalpy value of 4.135 J/g.

In some embodiments of the present disclosure, the crystal form B has a differential scanning calorimetry analysis pattern showing an onset of an endothermic peak at 230.51±2° C., and further reaches a peak value of the endothermic peak at 231.37±2° C.; and even further has an enthalpy value of 113.950 J/g.

In some embodiments of the present disclosure, the differential scanning calorimetry (DSC) analysis pattern of the crystal form B is substantially as shown in FIG. 4.

In some embodiments of the present disclosure, the crystal form B has a thermal gravimetric analysis pattern showing a weight loss of 4.741% at 122.68° C.; the "%" represents mass percentage.

In some embodiments of the present disclosure, the thermal gravimetric analysis (TGA) pattern of the crystal form B is substantially as shown in FIG. 4.

The present disclosure provides a crystal form D of a five-membered-fused six-membered compound represented by formula I, which has an X-ray powder diffraction pattern expressed by 2θ angles comprising characteristic peaks at 9.51±0.20°, 15.35±0.20°, 19.27±0.20°, and 24.20±0.20°;

I

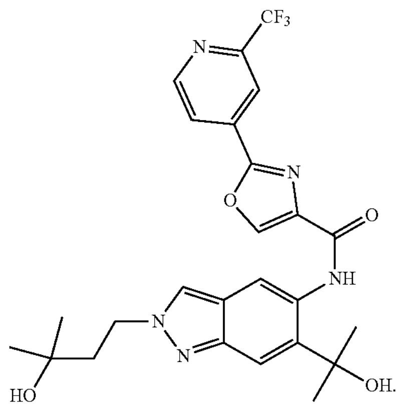

In some embodiments of the present disclosure, the crystal form D has an X-ray powder diffraction pattern expressed by 2θ angles further comprising characteristic peaks at one or more of 9.90±0.20°, 20.01±0.20°, 20.75±0.20°, and 29.18±0.20°.

In some embodiments of the present disclosure, the crystal form D has an X-ray powder diffraction pattern expressed by 2θ angles comprising characteristic peaks at 9.51±0.20°, 9.90±0.20°, 15.35±0.20°, 19.27±0.20°, 20.01±0.20°, 20.75±0.20°, 24.20±0.20°, and 29.18±0.20°.

In some embodiments of the present disclosure, the crystal form D has an X-ray powder diffraction pattern expressed by 2θ angles comprising diffraction peaks at the diffraction angles shown in the following table:

| Number | 2θ Angle/° |
|---|---|
| 1 | 7.73 |
| 2 | 9.51 |
| 3 | 9.90 |
| 4 | 10.16 |
| 5 | 10.87 |
| 6 | 11.18 |
| 7 | 12.86 |
| 8 | 13.34 |
| 9 | 14.40 |
| 10 | 15.35 |
| 11 | 15.86 |
| 12 | 16.79 |
| 13 | 19.27 |
| 14 | 20.01 |
| 15 | 20.57 |
| 16 | 20.75 |
| 17 | 22.36 |
| 18 | 23.34 |
| 19 | 24.20 |
| 20 | 24.78 |
| 21 | 25.20 |
| 22 | 25.88 |
| 23 | 26.49 |
| 24 | 27.32 |
| 25 | 29.18 |
| 26 | 29.69 |
| 27 | 30.87 |
| 28 | 33.29 |
| 29 | 34.20 |
| 30 | 34.65. |

In some embodiments of the present disclosure, diffraction peaks, d-spacing values, and relative intensities of the X-ray powder diffraction pattern of the crystal form D expressed by 2θ angles are shown in the following table:

| Number | 2θ Angle/° | d-Spacing/Å | Relative Intensity/% |
|---|---|---|---|
| 1 | 7.73 | 11.43 | 2.13 |
| 2 | 9.51 | 9.29 | 100.00 |
| 3 | 9.90 | 8.93 | 22.69 |
| 4 | 10.16 | 8.70 | 3.27 |
| 5 | 10.87 | 8.13 | 1.81 |
| 6 | 11.18 | 7.91 | 5.16 |
| 7 | 12.86 | 6.88 | 3.51 |
| 8 | 13.34 | 6.63 | 0.46 |
| 9 | 14.40 | 6.15 | 4.94 |
| 10 | 15.35 | 5.77 | 5.65 |
| 11 | 15.86 | 5.58 | 5.09 |
| 12 | 16.79 | 5.28 | 0.35 |
| 13 | 19.27 | 4.60 | 31.92 |
| 14 | 20.01 | 4.43 | 19.00 |
| 15 | 20.57 | 4.31 | 3.92 |
| 16 | 20.75 | 4.28 | 8.66 |
| 17 | 22.36 | 3.97 | 0.99 |
| 18 | 23.34 | 3.81 | 1.46 |
| 19 | 24.20 | 3.68 | 26.23 |
| 20 | 24.78 | 3.59 | 1.33 |

-continued

| Number | 2θ Angle/° | d-Spacing/Å | Relative Intensity/% |
|---|---|---|---|
| 21 | 25.20 | 3.53 | 3.79 |
| 22 | 25.88 | 3.44 | 0.89 |
| 23 | 26.49 | 3.36 | 0.77 |
| 24 | 27.32 | 3.26 | 1.18 |
| 25 | 29.18 | 3.06 | 4.82 |
| 26 | 29.69 | 3.01 | 4.53 |
| 27 | 30.87 | 2.89 | 0.93 |
| 28 | 33.29 | 2.69 | 0.63 |
| 29 | 34.20 | 2.62 | 6.19 |
| 30 | 34.65 | 2.59 | 2.26. |

In some embodiments of the present disclosure, the X-ray powder diffraction (XRPD) pattern of the crystal form D is substantially as shown in FIG. 7.

In some embodiments of the present disclosure, the crystal form D has a differential scanning calorimetry analysis pattern showing an onset of an endothermic peak at 231.13±2° C., and further reaches a peak value of the endothermic peak at 232.25±2° C.; and even further has an enthalpy value of 115.52 J/g.

In some embodiments of the present disclosure, the differential scanning calorimetry (DSC) analysis pattern of the crystal form D is substantially as shown in FIG. 8.

In some embodiments of the present disclosure, the crystal form D has a thermal gravimetric analysis pattern showing a weight loss of 2.826% at 116.38° C.; the "%" represents mass percentage.

In some embodiments of the present disclosure, the thermal gravimetric analysis (TGA) pattern of the crystal form D is substantially as shown in FIG. 8.

The present disclosure provides a crystal form E of a five-membered-fused six-membered compound represented by formula I, which has an X-ray powder diffraction pattern expressed by 2θ angles comprising characteristic peaks at 9.21±0.20°, 10.61±0.20°, 13.93±0.20°, 18.66±0.20°, and 23.43±0.20°;

I

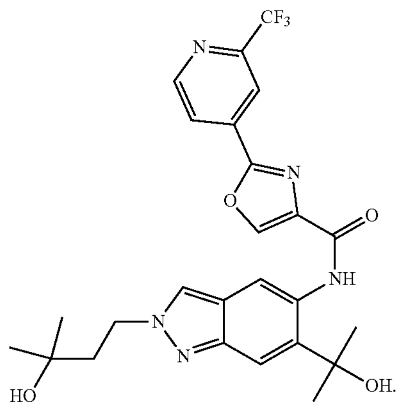

In some embodiments of the present disclosure, the crystal form E has an X-ray powder diffraction pattern expressed by 2θ angles further comprising characteristic peaks at one or more of 20.06±0.20°, 21.85±0.20°, and 28.25±0.20°.

In some embodiments of the present disclosure, the crystal form E has an X-ray powder diffraction pattern expressed by 2θ angles comprising characteristic peaks at 9.21±0.20°, 10.61±0.20°, 13.93±0.20°, 18.66±0.20°, 20.06±0.20°, 21.85±0.20°, 23.43±0.20°, and 28.25±0.20°.

In some embodiments of the present disclosure, the crystal form E has an X-ray powder diffraction pattern expressed by 2θ angles comprising diffraction peaks at the diffraction angles shown in the following table:

| Number | 2θ Angle/° |
|---|---|
| 1 | 9.23 |
| 2 | 9.77 |
| 3 | 10.61 |
| 4 | 12.71 |
| 5 | 13.15 |
| 6 | 13.94 |
| 7 | 14.51 |
| 8 | 14.88 |
| 9 | 15.75 |
| 10 | 17.09 |
| 11 | 18.15 |
| 12 | 18.67 |
| 13 | 19.43 |
| 14 | 20.06 |
| 15 | 20.90 |
| 16 | 21.85 |
| 17 | 23.42 |
| 18 | 27.97 |
| 19 | 28.25 |
| 20 | 33.50. |

In some embodiments of the present disclosure, diffraction peaks, d-spacing values, and relative intensities of the X-ray powder diffraction pattern of the crystal form E expressed by 2θ angles are shown in the following table:

| Number | 2θ Angle/° | d-Spacing/Å | Relative Intensity/% |
|---|---|---|---|
| 1 | 9.23 | 9.57 | 100.00 |
| 2 | 9.77 | 9.04 | 9.50 |
| 3 | 10.61 | 8.33 | 5.54 |
| 4 | 12.71 | 6.96 | 10.31 |
| 5 | 13.15 | 6.73 | 1.61 |
| 6 | 13.94 | 6.35 | 2.08 |
| 7 | 14.51 | 6.10 | 1.06 |
| 8 | 14.88 | 5.95 | 1.39 |
| 9 | 15.75 | 5.63 | 2.39 |
| 10 | 17.09 | 5.18 | 4.94 |
| 11 | 18.15 | 4.88 | 0.44 |
| 12 | 18.67 | 4.75 | 41.44 |
| 13 | 19.43 | 4.57 | 4.85 |
| 14 | 20.06 | 4.42 | 8.06 |
| 15 | 20.90 | 4.25 | 2.38 |
| 16 | 21.85 | 4.07 | 6.93 |
| 17 | 23.42 | 3.80 | 23.02 |
| 18 | 27.97 | 3.19 | 4.30 |
| 19 | 28.25 | 3.16 | 3.48 |
| 20 | 33.50 | 2.67 | 4.56. |

In some embodiments of the present disclosure, the X-ray powder diffraction (XRPD) pattern of the crystal form E is substantially as shown in FIG. 9.

In some embodiments of the present disclosure, the crystal form E has a differential scanning calorimetry analysis pattern showing an onset of an endothermic peak at 48.59±2° C., and further reaches a peak value of the endothermic peak at 51.08±2° C.; and even further has an enthalpy value of 5.451 J/g.

In some embodiments of the present disclosure, the crystal form E has a differential scanning calorimetry analysis pattern showing an onset of an endothermic peak at 90.07±2° C., and further reaches a peak value of the endothermic peak at 95.66±2° C.; and even further has an enthalpy value of 19.797 J/g.

In some embodiments of the present disclosure, the crystal form E has a differential scanning calorimetry analysis pattern showing an onset of an endothermic peak at 225.15±2° C., and further reaches a peak value of the endothermic peak at 228.25±2° C.; and even further has an enthalpy value of 86.445 J/g.

In some embodiments of the present disclosure, the differential scanning calorimetry (DSC) analysis pattern of the crystal form E is substantially as shown in FIG. 10.

In some embodiments of the present disclosure, the crystal form E has a thermal gravimetric analysis pattern showing a weight loss of 5.585% at 119.49° C.; the "%" represents mass percentage.

In some embodiments of the present disclosure, the thermal gravimetric analysis (TGA) pattern of the crystal form E is substantially as shown in FIG. 10.

The present disclosure provides a crystal form F of a five-membered-fused six-membered compound represented by formula I, which has an X-ray powder diffraction pattern expressed by 2θ angles comprising characteristic peaks at 5.53±0.20°, 5.93±0.20°, 10.38±0.20°, and 22.37±0.20°;

I

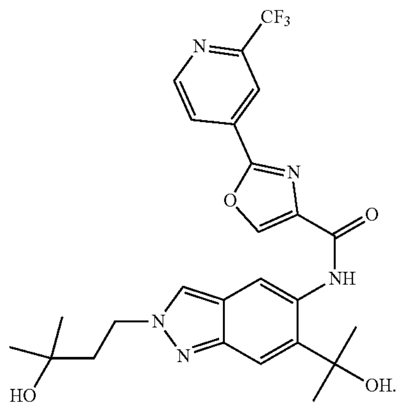

In some embodiments of the present disclosure, the crystal form F has an X-ray powder diffraction pattern expressed by 2θ angles further comprising characteristic peaks at one or more of 10.21±0.20°, 11.11±0.20°, 16.72±0.20°, and 25.78±0.20°.

In some embodiments of the present disclosure, the crystal form F has an X-ray powder diffraction pattern expressed by 2θ angles comprising characteristic peaks at 5.53±0.20°, 5.93±0.20°, 10.21±0.20°, 10.38±0.20°, 11.11±0.20°, 16.72±0.20°, 22.37±0.20°, and 25.78±0.20°.

In some embodiments of the present disclosure, the crystal form F has an X-ray powder diffraction pattern expressed by 2θ angles comprising diffraction peaks at the diffraction angles shown in the following table:

| Number | 2θ Angle/° |
|---|---|
| 1 | 5.53 |
| 2 | 5.93 |
| 3 | 6.12 |
| 4 | 7.95 |
| 5 | 9.85 |
| 6 | 10.21 |
| 7 | 10.38 |
| 8 | 10.55 |
| 9 | 11.11 |
| 10 | 11.47 |
| 11 | 12.35 |
| 12 | 13.25 |

-continued

| Number | 2θ Angle/° |
|---|---|
| 13 | 14.55 |
| 14 | 14.87 |
| 15 | 15.86 |
| 16 | 16.72 |
| 17 | 16.91 |
| 18 | 17.70 |
| 19 | 17.94 |
| 20 | 19.83 |
| 21 | 21.15 |
| 22 | 21.83 |
| 23 | 22.37 |
| 24 | 23.06 |
| 25 | 23.37 |
| 26 | 24.14 |
| 27 | 24.59 |
| 28 | 24.84 |
| 29 | 25.78 |
| 30 | 25.98 |
| 31 | 26.22 |
| 32 | 26.88 |
| 33 | 27.43 |
| 34 | 28.09 |
| 35 | 31.42 |
| 36 | 33.85 |
| 37 | 34.09 |
| 38 | 35.57. |

In some embodiments of the present disclosure, diffraction peaks, d-spacing values, and relative intensities of the X-ray powder diffraction pattern of the crystal form F expressed by 2θ angles are shown in the following table:

| Number | 2θ Angle/° | d-Spacing/Å | Relative Intensity/% |
|---|---|---|---|
| 1 | 5.53 | 15.96 | 26.20 |
| 2 | 5.93 | 14.89 | 13.26 |
| 3 | 6.12 | 14.43 | 34.33 |
| 4 | 7.95 | 11.11 | 33.35 |
| 5 | 9.85 | 8.97 | 2.34 |
| 6 | 10.21 | 8.66 | 28.81 |
| 7 | 10.38 | 8.52 | 82.19 |
| 8 | 10.55 | 8.38 | 13.78 |
| 9 | 11.11 | 7.96 | 96.68 |
| 10 | 11.47 | 7.71 | 7.48 |
| 11 | 12.35 | 7.16 | 18.98 |
| 12 | 13.25 | 6.68 | 2.69 |
| 13 | 14.55 | 6.08 | 2.97 |
| 14 | 14.87 | 5.96 | 6.52 |
| 15 | 15.86 | 5.59 | 44.50 |
| 16 | 16.72 | 5.30 | 33.17 |
| 17 | 16.91 | 5.24 | 23.83 |
| 18 | 17.70 | 5.01 | 4.35 |
| 19 | 17.94 | 4.94 | 3.33 |
| 20 | 19.83 | 4.47 | 4.64 |
| 21 | 21.15 | 4.20 | 43.26 |
| 22 | 21.83 | 4.07 | 37.17 |
| 23 | 22.37 | 3.97 | 100.00 |
| 24 | 23.06 | 3.85 | 7.85 |
| 25 | 23.37 | 3.80 | 29.30 |
| 26 | 24.14 | 3.68 | 3.89 |
| 27 | 24.59 | 3.62 | 8.33 |
| 28 | 24.84 | 3.58 | 10.99 |
| 29 | 25.78 | 3.45 | 23.92 |
| 30 | 25.98 | 3.43 | 13.74 |
| 31 | 26.22 | 3.40 | 3.24 |
| 32 | 26.88 | 3.31 | 9.38 |
| 33 | 27.43 | 3.25 | 15.36 |
| 34 | 28.09 | 3.17 | 13.63 |
| 35 | 31.42 | 2.85 | 20.13 |
| 36 | 33.85 | 2.65 | 15.91 |
| 37 | 34.09 | 2.63 | 2.69 |
| 38 | 35.57 | 2.52 | 4.70. |

In some embodiments of the present disclosure, the X-ray powder diffraction (XRPD) pattern of the crystal form F is substantially as shown in FIG. 11.

In some embodiments of the present disclosure, the crystal form F has a differential scanning calorimetry analysis pattern showing an onset of an endothermic peak at 49.64±2° C., and further reaches a peak value of the endothermic peak at 52.43±2° C.; and even further has an enthalpy value of 3.400 J/g.

In some embodiments of the present disclosure, the crystal form F has a differential scanning calorimetry analysis pattern showing an onset of an endothermic peak at 97.99±2° C., and further reaches a peak value of the endothermic peak at 103.02±2° C.; and even further has an enthalpy value of 9.028 J/g.

In some embodiments of the present disclosure, the crystal form F has a differential scanning calorimetry analysis pattern showing an onset of an endothermic peak at 225.07±2° C., and further reaches a peak value of the endothermic peak at 226.71±2° C.; and even further has an enthalpy value of 92.201 J/g.

In some embodiments of the present disclosure, the differential scanning calorimetry (DSC) analysis pattern of the crystal form F is substantially as shown in FIG. 12.

In some embodiments of the present disclosure, the crystal form F has a thermal gravimetric analysis pattern showing a weight loss of 1.066% at 127.37° C.; the "%" represents mass percentage.

In some embodiments of the present disclosure, the thermal gravimetric analysis (TGA) pattern of the crystal form F is substantially as shown in FIG. 12.

The present disclosure provides a crystal form G of a five-membered-fused six-membered compound represented by formula I, which has an X-ray powder diffraction pattern expressed by 2θ angles comprising characteristic peaks at 9.74±0.20°, 13.56±0.20°, 16.39±0.20°, and 24.51±0.20°;

I

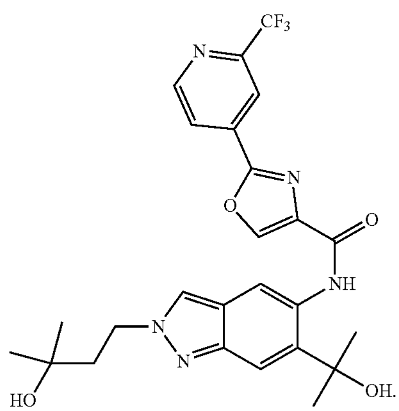

In some embodiments of the present disclosure, the crystal form G has an X-ray powder diffraction pattern expressed by 2θ angles further comprising characteristic peaks at one or more of 7.09±0.20°, 18.50±0.20°, 20.94±0.20°, and 23.36±0.20°.

In some embodiments of the present disclosure, the crystal form G has an X-ray powder diffraction pattern expressed by 2θ angles comprising characteristic peaks at 7.09±0.20°, 9.74±0.20°, 13.56±0.20°, 16.39±0.20°, 18.50±0.20°, 20.94±0.20°, 23.36±0.20°, and 24.51±0.20°.

The present disclosure provides a crystal form G of a five-membered-fused six-membered compound represented by formula I, which has an X-ray powder diffraction pattern expressed by 2θ angles comprising characteristic peaks at 9.74±0.20°, 13.56±0.20°, 11.07±0.20°, 11.45±0.20°, 16.39±0.20°, 20.94±0.20°, and 23.36±0.20°;

I

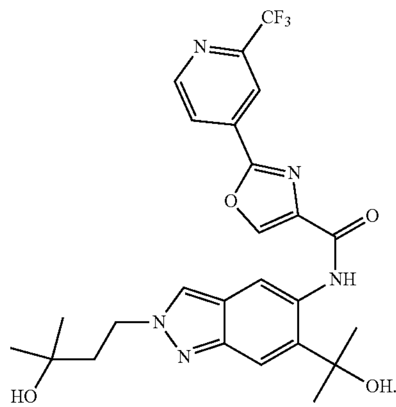

In some embodiments of the present disclosure, the crystal form G has an X-ray powder diffraction pattern expressed by 2θ angles further comprising characteristic peaks at one or more of 7.09±0.20°, 14.28±0.20°, 15.61±0.20°, 18.5±0.20°, 20.36±0.20°, and 24.51±0.20°.

In some embodiments of the present disclosure, the crystal form G has an X-ray powder diffraction pattern expressed by 2θ angles comprising diffraction peaks at the diffraction angles shown in the following table:

| Number | 2θ Angle/° |
|---|---|
| 1 | 4.86 |
| 2 | 7.09 |
| 3 | 9.74 |
| 4 | 10.35 |
| 5 | 11.07 |
| 6 | 11.45 |
| 7 | 13.56 |
| 8 | 14.28 |
| 9 | 15.42 |
| 10 | 15.61 |
| 11 | 15.87 |
| 12 | 16.39 |
| 13 | 18.07 |
| 14 | 18.50 |
| 15 | 19.27 |
| 16 | 19.66 |
| 17 | 19.94 |
| 18 | 20.13 |
| 19 | 20.36 |
| 20 | 20.94 |
| 21 | 21.52 |
| 22 | 22.49 |
| 23 | 23.22 |
| 24 | 23.36 |
| 25 | 24.13 |
| 26 | 24.51 |
| 27 | 26.89 |
| 28 | 27.52 |
| 29 | 28.25 |
| 30 | 28.91 |
| 31 | 29.38 |
| 32 | 30.18 |
| 33 | 31.69 |
| 34 | 33.35 |

-continued

| Number | 2θ Angle/° |
|---|---|
| 35 | 34.88 |
| 36 | 39.18. |

In some embodiments of the present disclosure, diffraction peaks, d-spacing values, and relative intensities of the X-ray powder diffraction pattern of the crystal form G expressed by 2θ angles are shown in the following table:

| Number | 2θ Angle/° | d-Spacing/Å | Relative Intensity/% |
|---|---|---|---|
| 1 | 4.86 | 18.17 | 1.49 |
| 2 | 7.09 | 12.46 | 19.43 |
| 3 | 9.74 | 9.07 | 100.00 |
| 4 | 10.35 | 8.54 | 5.18 |
| 5 | 11.07 | 7.99 | 43.14 |
| 6 | 11.45 | 7.72 | 50.03 |
| 7 | 13.56 | 6.52 | 81.21 |
| 8 | 14.28 | 6.20 | 24.70 |
| 9 | 15.42 | 5.74 | 1.10 |
| 10 | 15.61 | 5.67 | 29.98 |
| 11 | 15.87 | 5.58 | 7.21 |
| 12 | 16.39 | 5.40 | 39.10 |
| 13 | 18.07 | 4.91 | 5.95 |
| 14 | 18.50 | 4.79 | 30.59 |
| 15 | 19.27 | 4.60 | 13.00 |
| 16 | 19.66 | 4.51 | 29.62 |
| 17 | 19.94 | 4.45 | 15.93 |
| 18 | 20.13 | 4.41 | 28.57 |
| 19 | 20.36 | 4.36 | 38.61 |
| 20 | 20.94 | 4.24 | 72.47 |
| 21 | 21.52 | 4.13 | 5.95 |
| 22 | 22.49 | 3.95 | 7.89 |
| 23 | 23.22 | 3.83 | 29.88 |
| 24 | 23.36 | 3.81 | 70.43 |
| 25 | 24.13 | 3.68 | 4.12 |
| 26 | 24.51 | 3.63 | 48.21 |
| 27 | 26.89 | 3.31 | 16.42 |
| 28 | 27.52 | 3.24 | 2.70 |
| 29 | 28.25 | 3.16 | 38.13 |
| 30 | 28.91 | 3.09 | 3.95 |
| 31 | 29.38 | 3.04 | 8.70 |
| 32 | 30.18 | 2.96 | 7.62 |
| 33 | 31.69 | 2.82 | 3.66 |
| 34 | 33.35 | 2.68 | 13.63 |
| 35 | 34.88 | 2.57 | 5.89 |
| 36 | 39.18 | 2.30 | 1.42. |

In some embodiments of the present disclosure, the X-ray powder diffraction (XRPD) pattern of the crystal form G is substantially as shown in FIG. 13.

In some embodiments of the present disclosure, the crystal form G has a differential scanning calorimetry analysis pattern showing an onset of an endothermic peak at 63.20±2° C., and further reaches a peak value of the endothermic peak at 76.01±2° C.; and even further has an enthalpy value of 25.610 J/g.

In some embodiments of the present disclosure, the crystal form G has a differential scanning calorimetry analysis pattern showing an onset of an endothermic peak at 150.82±2° C., and further reaches a peak value of the endothermic peak at 153.33±2° C.; and even further has an enthalpy value of 12.882 J/g.

In some embodiments of the present disclosure, the crystal form G has a differential scanning calorimetry analysis pattern showing an onset of an endothermic peak at 230.69±2° C., and further reaches a peak value of the endothermic peak at 231.37±2° C.; and even further has an enthalpy value of 111.380 J/g.

In some embodiments of the present disclosure, the differential scanning calorimetry (DSC) analysis pattern of the crystal form G is substantially as shown in FIG. 14.

In some embodiments of the present disclosure, the crystal form G has a thermal gravimetric analysis pattern showing a weight loss of 3.405% at 130.90° C.; the "%" represents mass percentage.

In some embodiments of the present disclosure, the thermal gravimetric analysis (TGA) pattern of the crystal form G is substantially as shown in FIG. 14.

The present disclosure also provides a preparation method for the crystal form G of the five-membered-fused six-membered compound represented by formula I, comprising the following operation: cooling a solution of the five-membered-fused six-membered compound represented by formula I to obtain the crystal form; wherein the solvent of the solution is an alcohol solvent.

In a certain embodiment, the alcohol solvent may be methanol.

In a certain embodiment, in the preparation method for crystal form G, the mass-to-volume ratio of the five-membered-fused six-membered compound represented by formula I to the alcohol solvent may be (10-100):1 mg/mL, such as 50:1 mg/mL.

In a certain embodiment, in the preparation method for crystal form G, the temperature of the solution is 30 to 70° C., such as 40° C., 45° C., 50° C., 55° C., 60° C., 65° C., and 70° C.

In a certain embodiment, in the preparation method for crystal form G, the rate for cooling is 3 to 10° C./hour, such as 5° C./hour.

In a certain embodiment, in the preparation method for crystal form G, the time for cooling is 1 to 20 hours, preferably 14 hours.

The present disclosure provides a salt of a five-membered-fused six-membered compound represented by formula I, wherein the salt is a hydrochloride salt, a sulfate salt, a phosphate salt, a sodium salt, or a potassium salt;

I

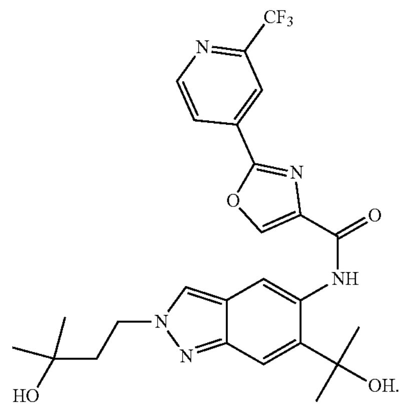

In a certain embodiment, the hydrochloride salt is preferably a monohydrochloride salt (the "monohydrochloride salt" means that the molar ratio of hydrochloric acid to the compound represented by formula I in the hydrochloride salt is 1:1).

In a certain embodiment, the sulfate salt is preferably a monosulfate salt (the "monosulfate salt" means that the molar ratio of sulfuric acid to the compound represented by formula I in the sulfate salt is 1:1).

In a certain embodiment, the phosphate salt is preferably a monophosphate salt (the "monophosphate salt" means that the molar ratio of phosphoric acid to the compound represented by formula I in the phosphate salt is 1:1).

In a certain embodiment, the sodium salt is preferably a monosodium salt (the "monosodium salt" means that the molar ratio of sodium ions to anions of the compound represented by formula I in the sodium salt is 1:1).

In a certain embodiment, the potassium salt is preferably a monopotassium salt (the "monopotassium salt" means that the molar ratio of potassium ions to anions of the compound represented by formula I in the potassium salt is 1:1).

In a certain embodiment, the hydrochloride salt is crystal form A, wherein the crystal form A has an X-ray powder diffraction pattern expressed by 2θ angles using Cu—Kα radiation and comprising characteristic peaks at 10.81±0.20°, 20.20±0.20°, 22.70±0.20°, 23.74±0.20°, 29.89±0.20°, and 39.32±0.20°.

In a certain embodiment, in the crystal form A of the hydrochloride salt, the X-ray powder diffraction pattern thereof expressed by 2θ angles further comprises characteristic peaks at one or more of 11.72±0.20°, 21.88±0.20°, 28.61±0.20°, and 31.26±0.20°.

In a certain embodiment, in the crystal form A of the hydrochloride salt, the X-ray powder diffraction pattern thereof expressed by 2θ angles comprises characteristic peaks at 10.81±0.20°, 11.72±0.20°, 20.20±0.20°, 21.88±0.20°, 22.70±0.20°, 23.74±0.20°, 28.61±0.20°, 29.89±0.20°, 31.26±0.20°, and 39.32±0.20°.

In a certain embodiment, in the crystal form A of the hydrochloride salt, diffraction peaks in the X-ray powder diffraction pattern of the crystal form A expressed by 2θ angles may be shown in the following table:

| Number | 2θ Angle/° |
|---|---|
| 1 | 7.37 |
| 2 | 9.06 |
| 3 | 10.81 |
| 4 | 11.24 |
| 5 | 11.72 |
| 6 | 12.60 |
| 7 | 13.67 |
| 8 | 14.91 |
| 9 | 15.20 |
| 10 | 16.26 |
| 11 | 16.76 |
| 12 | 17.10 |
| 13 | 18.12 |
| 14 | 18.45 |
| 15 | 18.79 |
| 16 | 19.26 |
| 17 | 19.68 |
| 18 | 19.97 |
| 19 | 20.20 |
| 20 | 20.46 |
| 21 | 21.01 |
| 22 | 21.16 |
| 23 | 21.32 |
| 24 | 21.88 |
| 25 | 22.50 |
| 26 | 22.70 |
| 27 | 23.00 |
| 28 | 23.74 |
| 29 | 24.18 |
| 30 | 24.51 |
| 31 | 24.96 |
| 32 | 25.32 |
| 33 | 25.53 |
| 34 | 25.68 |
| 35 | 26.02 |
| 36 | 26.34 |

-continued

| Number | 2θ Angle/° |
|---|---|
| 37 | 26.64 |
| 38 | 26.89 |
| 39 | 27.70 |
| 40 | 28.04 |
| 41 | 28.39 |
| 42 | 28.61 |
| 43 | 28.84 |
| 44 | 29.24 |
| 45 | 29.89 |
| 46 | 30.18 |
| 47 | 31.00 |
| 48 | 31.27 |
| 49 | 32.58 |
| 50 | 32.99 |
| 51 | 33.55 |
| 52 | 33.91 |
| 53 | 35.80 |
| 54 | 36.28 |
| 55 | 36.90 |
| 56 | 37.23 |
| 57 | 37.38 |
| 58 | 38.28 |
| 59 | 38.57 |
| 60 | 39.32 |
| 61 | 39.54. |

In a certain embodiment, in the crystal form A of the hydrochloride salt, diffraction peaks and relative intensities in the X-ray powder diffraction pattern of the crystal form A expressed by 2θ angles and relative intensities may be further shown in the following table:

| Number | 2θ Angle/° | Relative Intensity/% |
|---|---|---|
| 1 | 7.37 | 36.01 |
| 2 | 9.06 | 3.59 |
| 3 | 10.81 | 7.77 |
| 4 | 11.24 | 2.66 |
| 5 | 11.72 | 75.99 |
| 6 | 12.60 | 3.84 |
| 7 | 13.67 | 23.57 |
| 8 | 14.91 | 4.83 |
| 9 | 15.20 | 9.70 |
| 10 | 16.26 | 18.08 |
| 11 | 16.76 | 17.45 |
| 12 | 17.10 | 5.33 |
| 13 | 18.12 | 30.64 |
| 14 | 18.45 | 100.00 |
| 15 | 18.79 | 29.90 |
| 16 | 19.26 | 3.08 |
| 17 | 19.68 | 4.03 |
| 18 | 19.97 | 71.79 |
| 19 | 20.20 | 25.35 |
| 20 | 20.46 | 16.12 |
| 21 | 21.01 | 9.74 |
| 22 | 21.16 | 2.32 |
| 23 | 21.32 | 2.27 |
| 24 | 21.88 | 58.88 |
| 25 | 22.50 | 4.04 |
| 26 | 22.70 | 33.39 |
| 27 | 23.00 | 5.40 |
| 28 | 23.74 | 7.95 |
| 29 | 24.18 | 26.66 |
| 30 | 24.51 | 1.87 |
| 31 | 24.96 | 4.32 |
| 32 | 25.32 | 4.69 |
| 33 | 25.53 | 26.11 |
| 34 | 25.68 | 6.57 |
| 35 | 26.02 | 53.73 |
| 36 | 26.34 | 6.08 |
| 37 | 26.64 | 4.71 |
| 38 | 26.89 | 4.40 |
| 39 | 27.70 | 3.30 |

-continued

| Number | 2θ Angle/° | Relative Intensity/% |
|---|---|---|
| 40 | 28.04 | 4.87 |
| 41 | 28.39 | 5.80 |
| 42 | 28.61 | 33.77 |
| 43 | 28.84 | 2.44 |
| 44 | 29.24 | 4.23 |
| 45 | 29.89 | 22.55 |
| 46 | 30.18 | 4.77 |
| 47 | 31.00 | 3.91 |
| 48 | 31.27 | 20.50 |
| 49 | 32.58 | 3.16 |
| 50 | 32.99 | 6.18 |
| 51 | 33.55 | 2.49 |
| 52 | 33.91 | 7.17 |
| 53 | 35.80 | 2.64 |
| 54 | 36.28 | 1.61 |
| 55 | 36.90 | 2.07 |
| 56 | 37.23 | 15.53 |
| 57 | 37.38 | 10.29 |
| 58 | 38.28 | 2.79 |
| 59 | 38.57 | 4.30 |
| 60 | 39.32 | 11.50 |
| 61 | 39.54 | 4.26. |

In a certain embodiment, the crystal form A of the hydrochloride salt has an X-ray powder diffraction (XRPD) pattern substantially as shown in FIG. 17.

In a certain embodiment, the crystal form A of the hydrochloride salt has a thermal gravimetric analysis pattern showing a weight loss of 2.070% at 125.06° C.; the "%" represents mass percentage; the crystal form A has a differential scanning calorimetry analysis pattern showing an onset of an endothermic peak at 184.04±2° C., and further reaches a peak value of the endothermic peak at 188.62±2° C.; and even further has an enthalpy value of 344.80 J/g.

In a certain embodiment, the crystal form A of the hydrochloride salt has a thermal gravimetric analysis and differential scanning calorimetry analysis pattern substantially as shown in FIG. 18.

In a certain embodiment, the hydrochloride salt is crystal form B, wherein the crystal form B has an X-ray powder diffraction pattern expressed by 2θ angles using Cu—Kα radiation and comprising characteristic peaks at 8.2±0.20°, 13.28±0.20°, 18.87±0.20°, 25.07±0.20°, 34.76±0.20°, and 35.21±0.20°.

In a certain embodiment, in the crystal form B of the hydrochloride salt, the X-ray powder diffraction pattern thereof expressed by 2θ angles further comprises characteristic peaks at one or more of 13.93±0.20°, 15.28±0.20°, 27.18±0.20°, and 28.99±0.20°.

In a certain embodiment, in the crystal form B of the hydrochloride salt, the X-ray powder diffraction pattern thereof expressed by 2θ angles comprises characteristic peaks at 8.2±0.20°, 13.28±0.20°, 13.93±0.20°, 15.28±0.20°, 18.87±0.20°, 25.07±0.20°, 27.18±0.20°, 28.99±0.20°, 34.76±0.20°, and 35.21±0.20°.

In a certain embodiment, in the crystal form B of the hydrochloride salt, diffraction peaks in the X-ray powder diffraction pattern of the crystal form B expressed by 2θ angles may be shown in the following table:

| Number | 2θ Angle/° |
|---|---|
| 1 | 7.37 |
| 2 | 7.70 |
| 3 | 8.20 |

-continued

| Number | 2θ Angle/° |
|---|---|
| 4 | 13.02 |
| 5 | 13.28 |
| 6 | 13.93 |
| 7 | 14.78 |
| 8 | 14.89 |
| 9 | 15.28 |
| 10 | 15.58 |
| 11 | 16.85 |
| 12 | 18.07 |
| 13 | 18.18 |
| 14 | 18.54 |
| 15 | 18.87 |
| 16 | 19.51 |
| 17 | 20.18 |
| 18 | 21.08 |
| 19 | 21.43 |
| 20 | 21.62 |
| 21 | 22.51 |
| 22 | 24.21 |
| 23 | 24.45 |
| 24 | 24.69 |
| 25 | 25.07 |
| 26 | 25.88 |
| 27 | 26.40 |
| 28 | 26.61 |
| 29 | 26.90 |
| 30 | 27.18 |
| 31 | 28.99 |
| 32 | 29.99 |
| 33 | 31.68 |
| 34 | 31.89 |
| 35 | 32.28 |
| 36 | 32.58 |
| 37 | 33.53 |
| 38 | 33.89 |
| 39 | 34.36 |
| 40 | 34.58 |
| 41 | 34.76 |
| 42 | 35.21 |
| 43 | 35.72 |
| 44 | 37.54 |
| 45 | 37.75 |
| 46 | 38.45 |
| 47 | 39.01. |

In a certain embodiment, in the crystal form B of the hydrochloride salt, diffraction peaks and relative intensities in the X-ray powder diffraction pattern of the crystal form B expressed by 2θ angles and relative intensities may be further shown in the following table:

| Number | 2θ Angle/° | Relative Intensity/% |
|---|---|---|
| 1 | 7.37 | 4.70 |
| 2 | 7.70 | 15.07 |
| 3 | 8.20 | 8.58 |
| 4 | 13.02 | 7.88 |
| 5 | 13.28 | 6.95 |
| 6 | 13.93 | 17.06 |
| 7 | 14.78 | 17.67 |
| 8 | 14.89 | 6.60 |
| 9 | 15.28 | 21.74 |
| 10 | 15.58 | 29.78 |
| 11 | 16.85 | 49.54 |
| 12 | 18.07 | 36.85 |
| 13 | 18.18 | 12.64 |
| 14 | 18.54 | 9.66 |
| 15 | 18.87 | 20.22 |
| 16 | 19.51 | 4.71 |
| 17 | 20.18 | 17.14 |
| 18 | 21.08 | 5.60 |
| 19 | 21.43 | 5.65 |
| 20 | 21.62 | 15.34 |

-continued

| Number | 2θ Angle/° | Relative Intensity/% |
|---|---|---|
| 21 | 22.51 | 26.94 |
| 22 | 24.21 | 35.79 |
| 23 | 24.45 | 13.47 |
| 24 | 24.69 | 8.62 |
| 25 | 25.07 | 6.87 |
| 26 | 25.88 | 26.18 |
| 27 | 26.40 | 100.00 |
| 28 | 26.61 | 12.46 |
| 29 | 26.90 | 15.65 |
| 30 | 27.18 | 32.10 |
| 31 | 28.99 | 6.89 |
| 32 | 29.99 | 2.75 |
| 33 | 31.68 | 5.43 |
| 34 | 31.89 | 3.26 |
| 35 | 32.28 | 9.17 |
| 36 | 32.58 | 2.64 |
| 37 | 33.53 | 4.05 |
| 38 | 33.89 | 4.61 |
| 39 | 34.36 | 7.05 |
| 40 | 34.58 | 10.26 |
| 41 | 34.76 | 4.78 |
| 42 | 35.21 | 5.49 |
| 43 | 35.72 | 6.06 |
| 44 | 37.54 | 1.35 |
| 45 | 37.75 | 5.80 |
| 46 | 38.45 | 6.20 |
| 47 | 39.01 | 3.80. |

In a certain embodiment, the crystal form B of the hydrochloride salt has an X-ray powder diffraction (XRPD) pattern substantially as shown in FIG. 19.

In a certain embodiment, the crystal form B of the hydrochloride salt has a thermal gravimetric analysis pattern showing a weight loss of 7.216% at 96.43° C.; the "%" represents mass percentage; the crystal form B has a differential scanning calorimetry analysis pattern showing an onset of an endothermic peak at 173.54±2° C., and further reaches a peak value of the endothermic peak at 184.54±2° C.; and even further has an enthalpy value of 259.36 J/g.

In a certain embodiment, the crystal form B of the hydrochloride salt has a thermal gravimetric analysis and differential scanning calorimetry analysis pattern substantially as shown in FIG. 20.

In a certain embodiment, the sulfate salt is crystal form A, wherein the crystal form A has an X-ray powder diffraction pattern expressed by 2θ angles using Cu—Kα radiation and comprising characteristic peaks at 19.62±0.20°, 27.19±0.20°, 28.70±0.20°, 32.36±0.20°, 33.43±0.20°, and 34.15±0.20°.

In a certain embodiment, in the crystal form A of the sulfate salt, the X-ray powder diffraction pattern thereof expressed by 2θ angles further comprises characteristic peaks at one or more of 14.94±0.20°, 17.42±0.20°, 22.76±0.20°, and 26.46±0.20°.

In a certain embodiment, in the crystal form A of the sulfate salt, the X-ray powder diffraction pattern thereof expressed by 2θ angles comprises characteristic peaks at 14.94±0.20°, 17.42±0.20°, 19.62±0.20°, 22.76±0.20°, 26.46±0.20°, 27.19±0.20°, 28.70±0.20°, 32.36±0.20°, 33.43±0.20°, and 34.15±0.20°.

In a certain embodiment, in the crystal form A of the sulfate salt, diffraction peaks in the X-ray powder diffraction pattern of the crystal form A expressed by 2θ angles may be shown in the following table:

| Number | 2θ Angle/° |
|---|---|
| 1 | 6.70 |
| 2 | 8.70 |
| 3 | 10.12 |
| 4 | 13.53 |
| 5 | 14.14 |
| 6 | 14.29 |
| 7 | 14.94 |
| 8 | 16.11 |
| 9 | 16.78 |
| 10 | 17.25 |
| 11 | 17.42 |
| 12 | 18.45 |
| 13 | 18.97 |
| 14 | 19.48 |
| 15 | 19.62 |
| 16 | 20.46 |
| 17 | 20.87 |
| 18 | 21.06 |
| 19 | 22.40 |
| 20 | 22.53 |
| 21 | 22.77 |
| 22 | 23.07 |
| 23 | 23.50 |
| 24 | 24.18 |
| 25 | 24.49 |
| 26 | 24.78 |
| 27 | 25.01 |
| 28 | 25.80 |
| 29 | 26.14 |
| 30 | 26.46 |
| 31 | 26.67 |
| 32 | 27.19 |
| 33 | 27.46 |
| 34 | 28.71 |
| 35 | 28.95 |
| 36 | 32.36 |
| 37 | 33.43 |
| 38 | 34.15 |
| 39 | 37.89 |
| 40 | 38.89 |
| 41 | 39.49. |

In a certain embodiment, in the crystal form A of the sulfate salt, diffraction peaks and relative intensities in the X-ray powder diffraction pattern of the crystal form A expressed by 2θ angles and relative intensities may be further shown in the following table:

| Number | 2θ Angle/° | Relative Intensity/% |
|---|---|---|
| 1 | 6.70 | 11.30 |
| 2 | 8.70 | 89.89 |
| 3 | 10.12 | 20.98 |
| 4 | 13.53 | 18.48 |
| 5 | 14.14 | 11.75 |
| 6 | 14.29 | 33.44 |
| 7 | 14.94 | 21.72 |
| 8 | 16.11 | 33.48 |
| 9 | 16.78 | 32.28 |
| 10 | 17.25 | 3.85 |
| 11 | 17.42 | 19.13 |
| 12 | 18.45 | 11.11 |
| 13 | 18.97 | 21.83 |
| 14 | 19.48 | 3.25 |
| 15 | 19.62 | 7.45 |
| 16 | 20.46 | 100.00 |
| 17 | 20.87 | 26.20 |
| 18 | 21.06 | 11.87 |
| 19 | 22.40 | 3.32 |
| 20 | 22.53 | 7.49 |
| 21 | 22.77 | 31.90 |
| 22 | 23.07 | 2.58 |
| 23 | 23.50 | 10.91 |
| 24 | 24.18 | 22.88 |

-continued

| Number | 2θ Angle/° | Relative Intensity/% |
|---|---|---|
| 25 | 24.49 | 57.84 |
| 26 | 24.78 | 37.97 |
| 27 | 25.01 | 7.00 |
| 28 | 25.80 | 3.52 |
| 29 | 26.14 | 6.31 |
| 30 | 26.46 | 13.48 |
| 31 | 26.67 | 20.63 |
| 32 | 27.19 | 12.62 |
| 33 | 27.46 | 14.71 |
| 34 | 28.71 | 6.06 |
| 35 | 28.95 | 6.19 |
| 36 | 32.36 | 5.15 |
| 37 | 33.43 | 6.27 |
| 38 | 34.15 | 7.30 |
| 39 | 37.89 | 7.71 |
| 40 | 38.89 | 5.71 |
| 41 | 39.49 | 3.17. |

In a certain embodiment, the crystal form A of the sulfate salt has an X-ray powder diffraction (XRPD) pattern substantially as shown in FIG. 21.

In a certain embodiment, the crystal form A of the sulfate salt has a thermal gravimetric analysis pattern showing a weight loss of 3.880% at 118.49° C.; the "%" represents mass percentage; the crystal form A has a differential scanning calorimetry analysis pattern showing an onset of an endothermic peak at 149.86±2° C., and further reaches a peak value of the endothermic peak at 160.23±2° C.; and even further has an enthalpy value of 229.21 J/g.

In a certain embodiment, the crystal form A of the sulfate salt has a thermal gravimetric analysis and differential scanning calorimetry analysis pattern substantially as shown in FIG. 22.

In a certain embodiment, the sulfate salt is crystal form B, wherein the crystal form B has an X-ray powder diffraction pattern expressed by 2θ angles using Cu—Kα radiation and comprising characteristic peaks at 15.86±0.20°, 16.53±0.20°, 20.05±0.20°, 28.46±0.20°, and 30.59±0.20°.

In a certain embodiment, in the crystal form B of the sulfate salt, the X-ray powder diffraction pattern thereof expressed by 2θ angles further comprises characteristic peaks at one or more of 9.00±0.20°, 12.52±0.20°, 21.21±0.20°, and 22.36±0.20°.

In a certain embodiment, in the crystal form B of the sulfate salt, the X-ray powder diffraction pattern thereof expressed by 2θ angles comprises characteristic peaks at 9.00±0.20°, 12.52±0.20°, 15.86±0.20°, 16.53±0.20°, 20.05±0.20°, 21.21±0.20°, 22.36±0.20°, 28.46±0.20°, and 30.59±0.20°.

In a certain embodiment, in the crystal form B of the sulfate salt, diffraction peaks in the X-ray powder diffraction pattern of the crystal form B expressed by 2θ angles may be shown in the following table:

| Number | 2θ Angle/° |
|---|---|
| 1 | 9.00 |
| 2 | 10.48 |
| 3 | 12.52 |
| 4 | 15.86 |
| 5 | 16.53 |
| 6 | 17.44 |
| 7 | 17.93 |
| 8 | 19.03 |
| 9 | 20.50 |
| 10 | 21.21 |
| 11 | 22.36 |
| 12 | 23.25 |
| 13 | 24.24 |
| 14 | 25.94 |
| 15 | 27.61 |
| 16 | 28.46 |
| 17 | 29.04 |
| 18 | 30.59. |

In a certain embodiment, in the crystal form B of the sulfate salt, diffraction peaks and relative intensities in the X-ray powder diffraction pattern of the crystal form B expressed by 2θ angles and relative intensities may be further shown in the following table:

| Number | 2θ Angle/° | Relative Intensity/% |
|---|---|---|
| 1 | 9.00 | 48.50 |
| 2 | 10.48 | 9.08 |
| 3 | 12.52 | 50.23 |
| 4 | 15.86 | 9.46 |
| 5 | 16.53 | 10.26 |
| 6 | 17.44 | 5.91 |
| 7 | 17.93 | 4.51 |
| 8 | 19.03 | 10.62 |
| 9 | 20.50 | 30.90 |
| 10 | 21.21 | 100.00 |
| 11 | 22.36 | 76.43 |
| 12 | 23.25 | 22.69 |
| 13 | 24.24 | 9.68 |
| 14 | 25.94 | 18.77 |
| 15 | 27.61 | 23.48 |
| 16 | 28.46 | 15.18 |
| 17 | 29.04 | 6.60 |
| 18 | 30.59 | 29.81. |

In a certain embodiment, the crystal form B of the sulfate salt has an X-ray powder diffraction (XRPD) pattern substantially as shown in FIG. 23.

In a certain embodiment, the crystal form B of the sulfate salt has a thermal gravimetric analysis pattern showing a weight loss of 6.895% at 92.04° C.; the "%" represents mass percentage; the crystal form B has a differential scanning calorimetry analysis pattern showing an onset of an endothermic peak at 126.34±2° C., and further reaches a peak value of the endothermic peak at 139.98±2° C.; and even further has an enthalpy value of 230.50 J/g.

In a certain embodiment, the crystal form B of the sulfate salt has a thermal gravimetric analysis and differential scanning calorimetry analysis pattern substantially as shown in FIG. 24.

In a certain embodiment, the sulfate salt is crystal form C, wherein the crystal form C has an X-ray powder diffraction pattern expressed by 2θ angles using Cu—Kα radiation and comprising characteristic peaks at 7.70±0.20°, 12.87±0.20°, 19.87±0.20°, 21.55±0.20°, and 25.94±0.20°.

In a certain embodiment, in the crystal form C of the sulfate salt, the X-ray powder diffraction pattern thereof expressed by 2θ angles further comprises characteristic peaks at one or more of 8.74±0.20°, 10.67±0.20°, 18.64±0.20°, and 19.05±0.20°.

In a certain embodiment, in the crystal form C of the sulfate salt, the X-ray powder diffraction pattern thereof expressed by 2θ angles comprises characteristic peaks at 7.70±0.20°, 8.74±0.20°, 10.67±0.20°, 12.87±0.20°, 18.64±0.20°, 19.05±0.20°, 19.87±0.20°, 21.55±0.20°, and 25.94±0.20°.

In a certain embodiment, in the crystal form C of the sulfate salt, diffraction peaks in the X-ray powder diffraction pattern of the crystal form C expressed by 2θ angles may be shown in the following table:

| Number | 2θ Angle/° |
|---|---|
| 1 | 6.72 |
| 2 | 7.70 |
| 3 | 8.53 |
| 4 | 8.74 |
| 5 | 10.67 |
| 6 | 12.87 |
| 7 | 13.57 |
| 8 | 14.38 |
| 9 | 14.78 |
| 10 | 15.53 |
| 11 | 17.42 |
| 12 | 18.34 |
| 13 | 18.64 |
| 14 | 19.05 |
| 15 | 19.87 |
| 16 | 20.50 |
| 17 | 21.29 |
| 18 | 21.55 |
| 19 | 22.41 |
| 20 | 23.03 |
| 21 | 23.35 |
| 22 | 24.22 |
| 23 | 24.55 |
| 24 | 24.85 |
| 25 | 25.94 |
| 26 | 26.74 |
| 27 | 27.55 |
| 28 | 28.40. |

In a certain embodiment, in the crystal form C of the sulfate salt, diffraction peaks and relative intensities in the X-ray powder diffraction pattern of the crystal form C expressed by 2θ angles and relative intensities may be further shown in the following table:

| Number | 2θ Angle/° | Relative Intensity/% |
|---|---|---|
| 1 | 6.72 | 10.88 |
| 2 | 7.70 | 13.86 |
| 3 | 8.53 | 21.83 |
| 4 | 8.74 | 13.91 |
| 5 | 10.67 | 7.39 |
| 6 | 12.87 | 27.52 |
| 7 | 13.57 | 7.10 |
| 8 | 14.38 | 32.55 |
| 9 | 14.78 | 11.30 |
| 10 | 15.53 | 16.49 |
| 11 | 17.42 | 13.53 |
| 12 | 18.34 | 17.52 |
| 13 | 18.64 | 11.56 |
| 14 | 19.05 | 20.18 |
| 15 | 19.87 | 14.35 |
| 16 | 20.50 | 13.78 |
| 17 | 21.29 | 57.72 |
| 18 | 21.55 | 100.00 |
| 19 | 22.41 | 75.28 |
| 20 | 23.03 | 14.56 |
| 21 | 23.35 | 19.69 |
| 22 | 24.22 | 11.28 |
| 23 | 24.55 | 14.26 |
| 24 | 24.85 | 8.50 |
| 25 | 25.94 | 51.32 |
| 26 | 26.74 | 9.46 |
| 27 | 27.55 | 10.67 |
| 28 | 28.40 | 20.19. |

In a certain embodiment, the crystal form C of the sulfate salt has an X-ray powder diffraction (XRPD) pattern substantially as shown in FIG. 25.

In a certain embodiment, the crystal form C of the sulfate salt has a thermal gravimetric analysis pattern showing a weight loss of 10.471% at 102.19° C.; the "%" represents mass percentage; the crystal form C has a differential scanning calorimetry analysis pattern showing an onset of an endothermic peak at 117.30±2° C., and further reaches a peak value of the endothermic peak at 122.26±2° C.; and even further has an enthalpy value of 54.426 J/g.

In a certain embodiment, the crystal form C of the sulfate salt has a thermal gravimetric analysis and differential scanning calorimetry analysis pattern substantially as shown in FIG. 26.

In a certain embodiment, the phosphate salt is crystal form A, wherein the crystal form A has an X-ray powder diffraction pattern expressed by 2θ angles using Cu—Kα radiation and comprising characteristic peaks at 10.04±0.20°, 14.10±0.20°, 18.10±0.20°, 22.80±0.20°, 24.57±0.20°, 28.44±0.20°, and 30.82±0.20°;

In a certain embodiment, in the crystal form A of the phosphate salt, the X-ray powder diffraction pattern thereof expressed by 2θ angles further comprises characteristic peaks at one or more of 6.57±0.20°, 18.53±0.20°, 19.97±0.20°, 22.43±0.20°, and 27.18±0.20°.

In a certain embodiment, in the crystal form A of the phosphate salt, the X-ray powder diffraction pattern thereof expressed by 2θ angles comprises characteristic peaks at 6.57±0.20°, 10.04±0.20°, 14.10±0.20°, 18.10±0.20°, 18.53±0.20°, 19.97±0.20°, 22.43±0.20°, 22.80±0.20°, 24.57±0.20°, 27.18±0.20°, 28.44±0.20°, and 30.82±0.20°.

In a certain embodiment, in the crystal form A of the phosphate salt, diffraction peaks in the X-ray powder diffraction pattern of the crystal form A expressed by 2θ angles may be shown in the following table:

| Number | 2θ Angle/° |
|---|---|
| 1 | 6.57 |
| 2 | 8.74 |
| 3 | 10.04 |
| 4 | 13.23 |
| 5 | 14.10 |
| 6 | 14.24 |
| 7 | 14.64 |
| 8 | 14.78 |
| 9 | 15.52 |
| 10 | 16.54 |
| 11 | 17.12 |
| 12 | 17.79 |
| 13 | 18.10 |
| 14 | 18.33 |
| 15 | 18.53 |
| 16 | 18.75 |
| 17 | 19.97 |
| 18 | 20.30 |
| 19 | 20.67 |
| 20 | 21.43 |
| 21 | 21.80 |
| 22 | 22.15 |
| 23 | 22.43 |
| 24 | 22.79 |
| 25 | 23.15 |
| 26 | 24.03 |
| 27 | 24.34 |
| 28 | 24.59 |
| 29 | 25.40 |
| 30 | 26.11 |
| 31 | 26.80 |
| 32 | 27.18 |
| 33 | 28.44 |

-continued

| Number | 2θ Angle/° |
|---|---|
| 34 | 28.65 |
| 35 | 30.01 |
| 36 | 30.15 |
| 37 | 30.48 |
| 38 | 30.82 |
| 39 | 31.52 |
| 40 | 32.13 |
| 41 | 33.16 |
| 42 | 33.57 |
| 43 | 37.00 |
| 44 | 37.38 |
| 45 | 37.78 |
| 46 | 39.00 |
| 47 | 39.29. |

In a certain embodiment, in the crystal form A of the phosphate salt, diffraction peaks and relative intensities in the X-ray powder diffraction pattern of the crystal form A expressed by 2θ angles and relative intensities may be further shown in the following table:

| Number | 2θ Angle/° | Relative Intensity/% |
|---|---|---|
| 1 | 6.57 | 75.66 |
| 2 | 8.74 | 100.00 |
| 3 | 10.04 | 11.10 |
| 4 | 13.23 | 29.20 |
| 5 | 14.10 | 6.52 |
| 6 | 14.24 | 4.71 |
| 7 | 14.64 | 4.03 |
| 8 | 14.78 | 6.29 |
| 9 | 15.52 | 48.30 |
| 10 | 16.54 | 13.08 |
| 11 | 17.12 | 2.96 |
| 12 | 17.79 | 8.17 |
| 13 | 18.10 | 5.62 |
| 14 | 18.33 | 1.24 |
| 15 | 18.53 | 5.68 |
| 16 | 18.75 | 2.09 |
| 17 | 19.97 | 68.80 |
| 18 | 20.30 | 31.67 |
| 19 | 20.67 | 10.76 |
| 20 | 21.43 | 2.89 |
| 21 | 21.80 | 4.42 |
| 22 | 22.15 | 4.98 |
| 23 | 22.43 | 8.59 |
| 24 | 22.79 | 17.34 |
| 25 | 23.15 | 2.86 |
| 26 | 24.03 | 6.25 |
| 27 | 24.34 | 14.16 |
| 28 | 24.59 | 11.80 |
| 29 | 25.40 | 10.69 |
| 30 | 26.11 | 5.04 |
| 31 | 26.80 | 23.50 |
| 32 | 27.18 | 7.35 |
| 33 | 28.44 | 5.05 |
| 34 | 28.65 | 1.63 |
| 35 | 30.01 | 2.19 |
| 36 | 30.15 | 1.57 |
| 37 | 30.48 | 3.17 |
| 38 | 30.82 | 5.31 |
| 39 | 31.52 | 1.21 |
| 40 | 32.13 | 3.31 |
| 41 | 33.16 | 2.37 |
| 42 | 33.57 | 3.95 |
| 43 | 37.00 | 3.20 |
| 44 | 37.38 | 3.89 |
| 45 | 37.78 | 4.99 |
| 46 | 39.00 | 7.81 |
| 47 | 39.29 | 3.96. |

In a certain embodiment, the crystal form A of the phosphate salt has an X-ray powder diffraction (XRPD) pattern substantially as shown in FIG. 27.

In a certain embodiment, the crystal form A of the phosphate salt has a thermal gravimetric analysis pattern showing a weight loss of 0.776% at 142.87° C.; the "%" represents mass percentage; the crystal form A has a differential scanning calorimetry analysis pattern showing an onset of an endothermic peak at 179.76±2° C., and further reaches a peak value of the endothermic peak at 180.61±2° C.; and even further has an enthalpy value of 265.82 J/g.

In a certain embodiment, the crystal form A of the phosphate salt has a thermal gravimetric analysis and differential scanning calorimetry analysis pattern substantially as shown in FIG. 28.

In a certain embodiment, the phosphate salt is crystal form B, wherein the crystal form B has an X-ray powder diffraction pattern expressed by 2θ angles using Cu—Kα radiation and comprising characteristic peaks at 17.96±0.20°, 21.10±0.20°, 21.41±0.20°, 23.38±0.20°, 26.91±0.20°, and 28.9±0.20°.

In a certain embodiment, in the crystal form B of the phosphate salt, the X-ray powder diffraction pattern thereof expressed by 2θ angles further comprises characteristic peaks at one or more of 7.40±0.20°, 17.61±0.20°, 19.69±0.20°, and 24.93±0.20°.

In a certain embodiment, in the crystal form B of the phosphate salt, the X-ray powder diffraction pattern thereof expressed by 2θ angles comprises characteristic peaks at 7.40±0.20°, 17.61±0.20°, 17.96±0.20°, 19.69±0.20°, 21.10±0.20°, 21.41±0.20°, 23.38±0.20°, 24.93±0.20°, 26.91±0.20°, and 28.9±0.20°.

In a certain embodiment, in the crystal form B of the phosphate salt, diffraction peaks in the X-ray powder diffraction pattern of the crystal form B expressed by 2θ angles may be shown in the following table:

| Number | 2θ Angle/° |
|---|---|
| 1 | 7.40 |
| 2 | 8.27 |
| 3 | 8.60 |
| 4 | 11.48 |
| 5 | 12.57 |
| 6 | 14.27 |
| 7 | 16.12 |
| 8 | 16.58 |
| 9 | 17.00 |
| 10 | 17.37 |
| 11 | 17.60 |
| 12 | 17.96 |
| 13 | 19.69 |
| 14 | 19.99 |
| 15 | 20.55 |
| 16 | 21.10 |
| 17 | 21.41 |
| 18 | 21.81 |
| 19 | 22.21 |
| 20 | 22.43 |
| 21 | 23.38 |
| 22 | 24.32 |
| 23 | 24.93 |
| 24 | 26.26 |
| 25 | 26.69 |
| 26 | 26.91 |
| 27 | 28.93 |
| 28 | 29.17 |
| 29 | 30.10 |
| 30 | 33.34 |
| 31 | 34.00. |

In a certain embodiment, in the crystal form B of the phosphate salt, diffraction peaks and relative intensities in the X-ray powder diffraction pattern of the crystal form B expressed by 2θ angles and relative intensities may be further shown in the following table:

| Number | 2θ Angle/° | Relative Intensity/% |
|---|---|---|
| 1 | 7.40 | 46.75 |
| 2 | 8.27 | 23.62 |
| 3 | 8.60 | 24.03 |
| 4 | 11.48 | 1.21 |
| 5 | 12.57 | 32.13 |
| 6 | 14.27 | 13.47 |
| 7 | 16.12 | 3.26 |
| 8 | 16.58 | 19.21 |
| 9 | 17.00 | 15.96 |
| 10 | 17.37 | 23.05 |
| 11 | 17.60 | 32.63 |
| 12 | 17.96 | 100.00 |
| 13 | 19.69 | 21.01 |
| 14 | 19.99 | 12.91 |
| 15 | 20.55 | 11.19 |
| 16 | 21.10 | 2.53 |
| 17 | 21.41 | 21.86 |
| 18 | 21.81 | 18.04 |
| 19 | 22.21 | 10.66 |
| 20 | 22.43 | 21.14 |
| 21 | 23.38 | 3.83 |
| 22 | 24.32 | 46.26 |
| 23 | 24.93 | 12.48 |
| 24 | 26.26 | 9.46 |
| 25 | 26.69 | 7.28 |
| 26 | 26.91 | 41.15 |
| 27 | 28.93 | 4.10 |
| 28 | 29.17 | 1.50 |
| 29 | 30.10 | 7.53 |
| 30 | 33.34 | 15.02 |
| 31 | 34.00 | 4.71. |

In a certain embodiment, the crystal form B of the phosphate salt has an X-ray powder diffraction (XRPD) pattern substantially as shown in FIG. 29.

In a certain embodiment, the crystal form B of the phosphate salt has a thermal gravimetric analysis pattern showing a weight loss of 1.071% at 74.52° C.; the "%" represents mass percentage; the crystal form B has a differential scanning calorimetry analysis pattern showing an onset of an endothermic peak at 159.94±2° C., and further reaches a peak value of the endothermic peak at 169.82±2° C.; and even further has an enthalpy value of 77.238 J/g.

In a certain embodiment, the crystal form B of the phosphate salt has a thermal gravimetric analysis and differential scanning calorimetry analysis pattern substantially as shown in FIG. 30.

In a certain embodiment, the sodium salt is crystal form A, wherein the crystal form A has an X-ray powder diffraction pattern expressed by 2θ angles using Cu—Kα radiation and comprising characteristic peaks at 7.04±0.20°, 11.05±0.20°, 11.55±0.20°, 15.18±0.20°, 17.98±0.20°, 22.09±0.20°, 25.65±0.20°, and 28.76±0.20°.

In a certain embodiment, in the crystal form A of the sodium salt, the X-ray powder diffraction pattern thereof expressed by 2θ angles further comprises characteristic peaks at one or more of 9.78±0.20°, 14.20±0.20°, 18.81±0.20°, 19.97±0.20°, and 24.13±0.20°.

In a certain embodiment, in the crystal form A of the sodium salt, the X-ray powder diffraction pattern thereof expressed by 2θ angles comprises characteristic peaks at 7.04±0.20°, 9.78±0.20°, 11.05±0.20°, 11.55±0.20°, 14.20±0.20°, 15.18±0.20°, 17.98±0.20°, 18.81±0.20°, 19.97±0.20°, 22.09±0.20°, 24.13±0.20°, 25.65±0.20°, and 28.76±0.20°.

In a certain embodiment, in the crystal form A of the sodium salt, diffraction peaks in the X-ray powder diffraction pattern of the crystal form A expressed by 2θ angles may be shown in the following table:

| Number | 2θ Angle/° |
|---|---|
| 1 | 7.04 |
| 2 | 9.78 |
| 3 | 10.23 |
| 4 | 11.05 |
| 5 | 11.36 |
| 6 | 11.55 |
| 7 | 11.69 |
| 8 | 12.52 |
| 9 | 13.86 |
| 10 | 14.20 |
| 11 | 14.37 |
| 12 | 15.19 |
| 13 | 15.45 |
| 14 | 15.80 |
| 15 | 16.22 |
| 16 | 16.60 |
| 17 | 17.98 |
| 18 | 18.15 |
| 19 | 18.36 |
| 20 | 18.81 |
| 21 | 19.71 |
| 22 | 19.97 |
| 23 | 20.43 |
| 24 | 21.13 |
| 25 | 21.27 |
| 26 | 21.47 |
| 27 | 21.71 |
| 28 | 22.10 |
| 29 | 22.40 |
| 30 | 22.87 |
| 31 | 23.35 |
| 32 | 23.61 |
| 33 | 23.94 |
| 34 | 24.13 |
| 35 | 25.34 |
| 36 | 25.65 |
| 37 | 25.98 |
| 38 | 26.45 |
| 39 | 26.72 |
| 40 | 26.96 |
| 41 | 27.14 |
| 42 | 27.39 |
| 43 | 27.80 |
| 44 | 28.01 |
| 45 | 28.76 |
| 46 | 29.13 |
| 47 | 30.63 |
| 48 | 32.11 |
| 49 | 32.66 |
| 50 | 32.90 |
| 51 | 33.36 |
| 52 | 33.99 |
| 53 | 34.39 |
| 54 | 34.82 |
| 55 | 35.48 |
| 56 | 35.88 |
| 57 | 36.26 |
| 58 | 36.69 |
| 59 | 37.05 |
| 60 | 37.38 |
| 61 | 38.15 |
| 62 | 38.34 |
| 63 | 38.54. |

In a certain embodiment, in the crystal form A of the sodium salt, diffraction peaks and relative intensities in the X-ray powder diffraction pattern of the crystal form A expressed by 2θ angles and relative intensities may be further shown in the following table:

| Number | 2θ Angle/° | Relative Intensity/% |
|---|---|---|
| 1 | 7.04 | 94.24 |
| 2 | 9.78 | 52.18 |
| 3 | 10.23 | 16.52 |
| 4 | 11.05 | 70.55 |
| 5 | 11.36 | 8.33 |
| 6 | 11.55 | 17.04 |
| 7 | 11.69 | 0.38 |
| 8 | 12.52 | 2.29 |
| 9 | 13.86 | 2.51 |
| 10 | 14.20 | 61.97 |
| 11 | 14.37 | 8.29 |
| 12 | 15.19 | 6.46 |
| 13 | 15.45 | 10.23 |
| 14 | 15.80 | 7.14 |
| 15 | 16.22 | 6.98 |
| 16 | 16.60 | 8.33 |
| 17 | 17.98 | 26.11 |
| 18 | 18.15 | 25.57 |
| 19 | 18.36 | 7.63 |
| 20 | 18.81 | 100.00 |
| 21 | 19.71 | 4.66 |
| 22 | 19.97 | 15.97 |
| 23 | 20.43 | 56.69 |
| 24 | 21.13 | 11.53 |
| 25 | 21.27 | 30.04 |
| 26 | 21.47 | 2.87 |
| 27 | 21.71 | 6.10 |
| 28 | 22.10 | 5.93 |
| 29 | 22.40 | 23.61 |
| 30 | 22.87 | 23.72 |
| 31 | 23.35 | 2.52 |
| 32 | 23.61 | 9.38 |
| 33 | 23.94 | 26.65 |
| 34 | 24.13 | 23.38 |
| 35 | 25.34 | 2.23 |
| 36 | 25.65 | 58.17 |
| 37 | 25.98 | 20.02 |
| 38 | 26.45 | 6.11 |
| 39 | 26.72 | 7.30 |
| 40 | 26.96 | 15.00 |
| 41 | 27.14 | 3.51 |
| 42 | 27.39 | 3.34 |
| 43 | 27.80 | 3.85 |
| 44 | 28.01 | 12.30 |
| 45 | 28.76 | 36.73 |
| 46 | 29.13 | 3.17 |
| 47 | 30.63 | 2.86 |
| 48 | 32.11 | 1.84 |
| 49 | 32.66 | 9.66 |
| 50 | 32.90 | 9.18 |
| 51 | 33.36 | 2.21 |
| 52 | 33.99 | 2.61 |
| 53 | 34.39 | 6.04 |
| 54 | 34.82 | 3.74 |
| 55 | 35.48 | 3.60 |
| 56 | 35.88 | 1.53 |
| 57 | 36.26 | 1.47 |
| 58 | 36.69 | 15.38 |
| 59 | 37.05 | 2.39 |
| 60 | 37.38 | 1.35 |
| 61 | 38.15 | 0.86 |
| 62 | 38.34 | 10.48 |
| 63 | 38.54 | 5.74. |

In a certain embodiment, the crystal form A of the sodium salt has an X-ray powder diffraction (XRPD) pattern substantially as shown in FIG. 31.

In a certain embodiment, the crystal form A of the sodium salt has a thermal gravimetric analysis pattern showing a weight loss of 6.279% at 116.94° C.; the "%" represents mass percentage; the crystal form A has a differential scanning calorimetry analysis pattern showing an onset of an endothermic peak at 228.53±2° C., and further reaches a peak value of the endothermic peak at 230.66±2° C.; and even further has an enthalpy value of 107.61 J/g.

In a certain embodiment, the crystal form A of the sodium salt has a thermal gravimetric analysis and differential scanning calorimetry analysis pattern substantially as shown in FIG. 32.

In a certain embodiment, the potassium salt is crystal form A, wherein the crystal form A has an X-ray powder diffraction pattern expressed by 2θ angles using Cu—Kα radiation and comprising characteristic peaks at 7.04±0.20°, 9.75±0.20°, 11.05±0.20°, 11.49±0.20°, 14.20±0.20°, 15.06±0.20°, 18.06±0.20°, 25.58±0.20°, and 30.93±0.20°.

In a certain embodiment, in the crystal form A of the potassium salt, the X-ray powder diffraction pattern thereof expressed by 2θ angles further comprises characteristic peaks at one or more of 19.46±0.20°, 19.96±0.20°, 23.54±0.20°, and 27.92±0.20°.

In a certain embodiment, in the crystal form A of the potassium salt, the X-ray powder diffraction pattern thereof expressed by 2θ angles comprises characteristic peaks at 7.04±0.20°, 9.75±0.20°, 11.05±0.20°, 11.49±0.20°, 14.20±0.20°, 15.06±0.20°, 18.06±0.20°, 19.46±0.20°, 19.96±0.20°, 23.54±0.20°, 25.58±0.20°, 27.92±0.20°, and 30.93±0.20°.

In a certain embodiment, in the crystal form A of the potassium salt, diffraction peaks in the X-ray powder diffraction pattern of the crystal form A expressed by 2θ angles may be shown in the following table:

| Number | 2θ Angle/° |
|---|---|
| 1 | 7.04 |
| 2 | 9.76 |
| 3 | 10.28 |
| 4 | 11.05 |
| 5 | 11.48 |
| 6 | 13.77 |
| 7 | 14.21 |
| 8 | 15.06 |
| 9 | 15.49 |
| 10 | 16.23 |
| 11 | 16.56 |
| 12 | 17.85 |
| 13 | 18.06 |
| 14 | 18.66 |
| 15 | 19.46 |
| 16 | 19.96 |
| 17 | 20.35 |
| 18 | 20.72 |
| 19 | 20.97 |
| 20 | 21.30 |
| 21 | 21.58 |
| 22 | 22.50 |
| 23 | 22.88 |
| 24 | 23.54 |
| 25 | 23.88 |
| 26 | 24.07 |
| 27 | 25.58 |
| 28 | 26.03 |
| 29 | 26.75 |
| 30 | 26.97 |
| 31 | 27.38 |
| 32 | 27.92 |
| 33 | 28.76 |
| 34 | 30.56 |
| 35 | 30.93 |
| 36 | 32.58 |
| 37 | 33.01 |
| 38 | 33.69 |
| 39 | 34.44. |

In a certain embodiment, in the crystal form A of the potassium salt, diffraction peaks and relative intensities in the X-ray powder diffraction pattern of the crystal form A expressed by 2θ angles and relative intensities may be further shown in the following table:

| Number | 2θ Angle/° | Relative Intensity/% |
|---|---|---|
| 1 | 7.04 | 25.69 |
| 2 | 9.76 | 17.41 |
| 3 | 10.28 | 5.10 |
| 4 | 11.05 | 6.29 |
| 5 | 11.48 | 15.99 |
| 6 | 13.77 | 1.60 |
| 7 | 14.21 | 72.55 |
| 8 | 15.06 | 10.02 |
| 9 | 15.49 | 25.51 |
| 10 | 16.23 | 2.54 |
| 11 | 16.56 | 5.98 |
| 12 | 17.85 | 21.03 |
| 13 | 18.06 | 11.65 |
| 14 | 18.66 | 53.46 |
| 15 | 19.46 | 17.87 |
| 16 | 19.96 | 19.71 |
| 17 | 20.35 | 6.36 |
| 18 | 20.72 | 5.03 |
| 19 | 20.97 | 19.73 |
| 20 | 21.30 | 15.56 |
| 21 | 21.58 | 2.45 |
| 22 | 22.50 | 23.44 |
| 23 | 22.88 | 13.73 |
| 24 | 23.54 | 32.35 |
| 25 | 23.88 | 6.23 |
| 26 | 24.07 | 57.22 |
| 27 | 25.58 | 100.00 |
| 28 | 26.03 | 20.71 |
| 29 | 26.75 | 11.42 |
| 30 | 26.97 | 16.86 |
| 31 | 27.38 | 8.76 |
| 32 | 27.92 | 23.58 |
| 33 | 28.76 | 51.14 |
| 34 | 30.56 | 2.76 |
| 35 | 30.93 | 7.85 |
| 36 | 32.58 | 5.39 |
| 37 | 33.01 | 6.45 |
| 38 | 33.69 | 3.97 |
| 39 | 34.44 | 2.57. |

In a certain embodiment, the crystal form A of the potassium salt has an X-ray powder diffraction (XRPD) pattern substantially as shown in FIG. 33.

In a certain embodiment, the crystal form A of the potassium salt has a thermal gravimetric analysis pattern showing a weight loss of 8.352% at 183.95° C.; the "%" represents mass percentage; the crystal form A has a differential scanning calorimetry analysis pattern showing an onset of an endothermic peak at 217.76±2° C., and further reaches a peak value of the endothermic peak at 222.51±2° C.; and even further has an enthalpy value of 102.94 J/g.

In a certain embodiment, the crystal form A of the potassium salt has a thermal gravimetric analysis and differential scanning calorimetry analysis pattern substantially as shown in FIG. 34.

The present disclosure also provides a pharmaceutical composition comprising one or more of the salt, crystal form A, crystal form B, crystal form C, crystal form D, crystal form E, crystal form F, and crystal form G of the five-membered-fused six-membered compound represented by formula I, and a pharmaceutical excipient.

In a certain embodiment, the pharmaceutical composition comprises the crystal form A or crystal form C of the five-membered-fused six-membered compound represented by formula I, and a pharmaceutical excipient.

In a certain embodiment, the pharmaceutical composition comprises one or more of the crystal form B, crystal form D, crystal form E, crystal form F, and crystal form G of the five-membered-fused six-membered compound represented by formula I, and a pharmaceutical excipient.

In a certain embodiment, the pharmaceutical composition comprises the salt of the five-membered-fused six-membered compound represented by formula I, and a pharmaceutical excipient.

In a certain embodiment, the pharmaceutical excipient may be a conventional pharmaceutical excipient in the art, preferably one or more of DMSO, Tween 80, polyethylene glycol 15-hydroxystearate, and saline; further, the pharmaceutical excipient consists of 5% DMSO, 10% Tween 80, 5% polyethylene glycol 15-hydroxystearate, and 80% saline, where % represents volume ratio.

In a certain embodiment, the mass-to-volume ratio of the salt of the five-membered-fused six-membered compound represented by formula I to the pharmaceutical excipient is 4:1 mg/mL.

The present disclosure also provides a use of substance Z in the manufacture of an FLT3 and/or IRAK4 inhibitor or a medicament for treating and/or preventing diseases related to FLT3 and/or IRAK4, wherein the substance Z is one or more of the salt, crystal form A, crystal form B, crystal form C, crystal form D, crystal form E, crystal form F, and crystal form G of the five-membered-fused six-membered compound represented by formula I.

In a certain embodiment, the substance Z is the crystal form A or crystal form C of the five-membered-fused six-membered compound represented by formula I.

In a certain embodiment, the substance Z is one or more of the crystal form B, crystal form D, crystal form E, crystal form F, and crystal form G of the five-membered-fused six-membered compound represented by formula I.

In a certain embodiment, the substance Z is the salt of the five-membered-fused six-membered compound represented by formula I.

The diseases related to FLT3 include hematological tumors and/or solid tumors.

The hematological tumors may be selected from one or more of acute lymphoblastic leukemia, acute myeloid leukemia, acute promyelocytic leukemia, chronic lymphocytic leukemia, chronic myeloid leukemia, chronic neutrophilic leukemia, acute undifferentiated leukemia, anaplastic large cell lymphoma, prolymphocytic leukemia, juvenile myelomonocytic leukemia, myelodysplastic syndrome, non-Hodgkin's lymphoma, multiple myeloma, myeloproliferative diseases, mantle cell lymphoma, and adult de novo acute myeloid leukemia;

the solid tumors may be selected from one or more of colorectal cancer, renal cell carcinoma, non-small cell lung cancer, bladder cancer, ovarian cancer, breast cancer, pancreatic cancer, gastric adenocarcinoma, prostate cancer, and lung cancer.

The diseases related to IRAK4 include autoimmune diseases, inflammatory diseases, cardiovascular diseases, cancer, or central nervous system diseases.

The autoimmune diseases may be selected from one or more of rheumatoid arthritis, osteoarthritis, juvenile arthritis, multiple sclerosis, lupus, diabetes (such as type I diabetes), psoriasis, psoriatic arthritis, atopic dermatitis, chronic obstructive pulmonary disease, Crohn's disease, ulcerative colitis, and irritable bowel syndrome.

The inflammatory diseases may be selected from, but not limited to, one or more of rheumatoid arthritis, osteoarthritis, juvenile arthritis, multiple sclerosis, lupus, diabetes (such as type I diabetes), psoriasis, psoriatic arthritis, atopic dermatitis, chronic obstructive pulmonary disease, Crohn's disease, ulcerative colitis, and irritable bowel syndrome.

The cardiovascular diseases may be stroke or atherosclerosis.

The present disclosure also provides a method for treating and/or preventing diseases related to FLT3 and/or IRAK4, comprising administering to a patient an effective amount of substance Z, wherein substance Z is one or more of the salt, crystal form A, crystal form B, crystal form C, crystal form D, crystal form E, crystal form F, or crystal form G of the five-membered-fused six-membered compound represented by formula I.

In a certain embodiment, the substance Z is the crystal form A or crystal form C of the five-membered-fused six-membered compound represented by formula I.

In a certain embodiment, the substance Z is one or more of the crystal form B, crystal form D, crystal form E, crystal form F, and crystal form G of the five-membered-fused six-membered compound represented by formula I.

In a certain embodiment, the substance Z is the salt of the five-membered-fused six-membered compound represented by formula I.

In a certain embodiment, the diseases related to FLT3 are the diseases related to FLT3 described in any one of the above embodiments.

In a certain embodiment, the diseases related to IRAK4 are the diseases related to IRAK4 described in any one of the above embodiments.

The present disclosure also provides a use of substance Z in the manufacture of a medicament, wherein substance Z is one or more of the salt, crystal form A, crystal form B, crystal form C, crystal form D, crystal form E, crystal form F, and crystal form G of the five-membered-fused six-membered compound represented by formula I; the medicament is used for treating and/or preventing one or more of hematological tumors, solid tumors, autoimmune diseases, inflammatory diseases, cardiovascular diseases, cancer, and central nervous system diseases.

In a certain embodiment, the substance Z is the crystal form A or crystal form C of the five-membered-fused six-membered compound represented by formula I.

In a certain embodiment, the substance Z is one or more of the crystal form B, crystal form D, crystal form E, crystal form F, and crystal form G of the five-membered-fused six-membered compound represented by formula I.

In a certain embodiment, the substance Z is the salt of the five-membered-fused six-membered compound represented by formula I.

In a certain embodiment, the hematological tumors are the hematological tumors described in any one of the above embodiments.

In a certain embodiment, the solid tumors are the solid tumors described in any one of the above embodiments.

In a certain embodiment, the autoimmune diseases are the autoimmune diseases described in any one of the above embodiments.

In a certain embodiment, the inflammatory diseases are the inflammatory diseases described in any one of the above embodiments.

In a certain embodiment, the cardiovascular diseases are the cardiovascular diseases described in any one of the above embodiments.

The present disclosure also provides a method for treating and/or preventing a disease, comprising administering to a patient an effective amount of substance Z, wherein substance Z is one or more of the salt, crystal form A, crystal form B, crystal form C, crystal form D, crystal form E, crystal form F, and crystal form G of the five-membered-fused six-membered compound represented by formula I; the disease is one or more selected from hematological tumors, solid tumors, autoimmune diseases, inflammatory diseases, cardiovascular diseases, cancer, and central nervous system diseases. In a certain embodiment, the substance Z is the crystal form A or crystal form C of the five-membered-fused six-membered compound represented by formula I.

In a certain embodiment, the substance Z is one or more of the crystal form B, crystal form D, crystal form E, crystal form F, and crystal form G of the five-membered-fused six-membered compound represented by formula I.

In a certain embodiment, the substance Z is the salt of the five-membered-fused six-membered compound represented by formula I.

In a certain embodiment, the hematological tumors are the hematological tumors described in any one of the above embodiments.

In a certain embodiment, the solid tumors are the solid tumors described in any one of the above embodiments.

In a certain embodiment, the autoimmune diseases are the autoimmune diseases described in any one of the above embodiments.

In a certain embodiment, the inflammatory diseases are the inflammatory diseases described in any one of the above embodiments.

In a certain embodiment, the cardiovascular diseases are the cardiovascular diseases described in any one of the above embodiments.

The present disclosure provides a compound represented by formula II-49-3

II-49-3

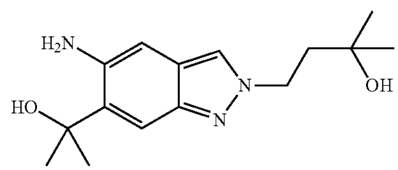

The present disclosure also provides a preparation method for the crystal form A of the five-membered-fused six-membered compound represented by formula I, comprising the following steps: adding a poor solvent to a solution of the five-membered-fused six-membered compound represented by formula I, and cooling to crystallize to obtain the crystal form A.

In a certain embodiment, in the preparation method for crystal form A, the solvent for the solution of the five-membered-fused six-membered compound represented by formula I may be a mixed solvent of a sulfoxide solvent and an alcohol solvent.

In a certain embodiment, in the preparation method for crystal form A, the sulfoxide solvent may be dimethyl sulfoxide.

In a certain embodiment, in the preparation method for crystal form A, the alcohol solvent may be ethanol and/or isopropyl alcohol.

In a certain embodiment, in the preparation method for crystal form A, the poor solvent may be an alcohol solvent and/or water, such as ethanol and/or isopropyl alcohol.

In a certain embodiment, in the preparation method for crystal form A, in the solution of the five-membered-fused six-membered compound represented by formula I, the mass-to-volume ratio of the five-membered-fused six-membered compound represented by formula I to the solvent of the solution of the five-membered-fused six-membered compound represented by formula I may be 1:(1-10) g/mL, such as 1:5 g/mL.

In a certain embodiment, in the preparation method for crystal form A, in the solvent of the solution of the five-membered-fused six-membered compound represented by formula I, the volume ratio of the sulfoxide solvent to the alcohol solvent may be (1-5):1, such as 2:1.

In a certain embodiment, in the preparation method for crystal form A, the volume ratio of the solution of the five-membered-fused six-membered compound represented by formula I to the poor solvent may be (1-10):18.3, such as 5:18.3.

In a certain embodiment, in the preparation method for crystal form A, the temperature for adding the poor solvent may be 20 to 65° C., such as 50° C.

In a certain embodiment, in the preparation method for crystal form A, the temperature for cooling the solution may be 30 to 70° C., such as 30° C., 40° C., 50° C., and 65° C.

In a certain embodiment, in the preparation method for crystal form A, the rate for cooling is 5 to 15° C./hour, such as 10° C./hour.

In a certain embodiment, in the preparation method for crystal form A, the time for cooling is 10 to 30 hours.

The present disclosure also provides a preparation method for the crystal form C of the five-membered-fused six-membered compound represented by formula I, comprising the following step: volatilizing a suspension of the five-membered-fused six-membered compound represented by formula I to obtain the crystal form C.

In a certain embodiment, in the preparation method for crystal form C, the solvent for the suspension is a mixture of an organic solvent and water.

In a certain embodiment, in the preparation method for crystal form C, the organic solvent may be one or more of alcohol solvents, ketone solvents, and nitrile solvents, such as ethanol, acetone, or acetonitrile.

In a certain embodiment, in the preparation method for crystal form C, the volume ratio of the organic solvent to water may be 60:40 to 99:1, such as 95:5.

In a certain embodiment, in the preparation method for crystal form C, the mass-to-volume ratio of the five-membered-fused six-membered compound represented by formula I to the solvent in the suspension may be (10-100):1 mg/mL, such as 50:1 mg/mL.

In a certain embodiment, in the preparation method for crystal form C, the temperature for volatilizing is room temperature.

In a certain embodiment, in the preparation method for crystal form C, the time for volatilizing is 1 to 5 days, preferably 3 days.

The terms "compound" and "pharmaceutically acceptable salt" may exist in the form of a single tautomer or a mixture thereof if tautomers exist, preferably predominantly in the form of the more stable tautomer.

The term "substantially" means that the positions of the peaks in the figure may vary slightly with minor changes in measurement equipment, measurement conditions, or between batches of products to be tested, and should not be considered as absolute values.

The term "pharmaceutical excipient" refers to the excipients and additives used in the production of medicaments and the preparation of prescriptions, encompassing all substances included in the pharmaceutical preparation other than the active ingredient. For details, please refer to the *Pharmacopoeia of the People's Republic of China* (2020 Edition) or *Handbook of Pharmaceutical Excipients* (Raymond C Rowe, 2009).

The term "treat/treatment" refers to any one of the following: (1) alleviating one or more biological manifestations of a disease; (2) interfering with one or more points in the biological cascade that triggers the disease; (3) slowing the progression of one or more biological manifestations of the disease.

The term "prevent/prevention" refers to reducing the risk of developing a disease.

The term "patient" refers to any animal that has received or is about to receive treatment, preferably a mammal, and most preferably a human. Mammals include, but are not limited to, cattle, horses, sheep, pigs, cats, dogs, mice, rats, rabbits, guinea pigs, monkeys, humans, and the like.

The term "room temperature" refers to 20 to 30° C., preferably 25° C.

The above preferred conditions can be combined arbitrarily to obtain preferred embodiments of the present disclosure without violating common knowledge in the art.

The reagents and starting materials used in the present disclosure are all commercially available.

The positive and progressive effects of the present disclosure are that the salts and crystal forms of the compound of the present disclosure exhibit inhibitory effects on FLT3 and/or IRAK4. Some crystal forms and salt forms of the present disclosure have high single melting points, demonstrating thermodynamic stability and high crystallinity. The crystal forms exhibit good physical and chemical stability under conditions of strong illumination, high temperature, and high humidity, while also having weak hygroscopicity. Some salt forms of the present disclosure can significantly enhance the plasma concentration and exposure of the compound in rats compared to the free base.

DETAILED DESCRIPTION OF THE INVENTION

Figure 1:
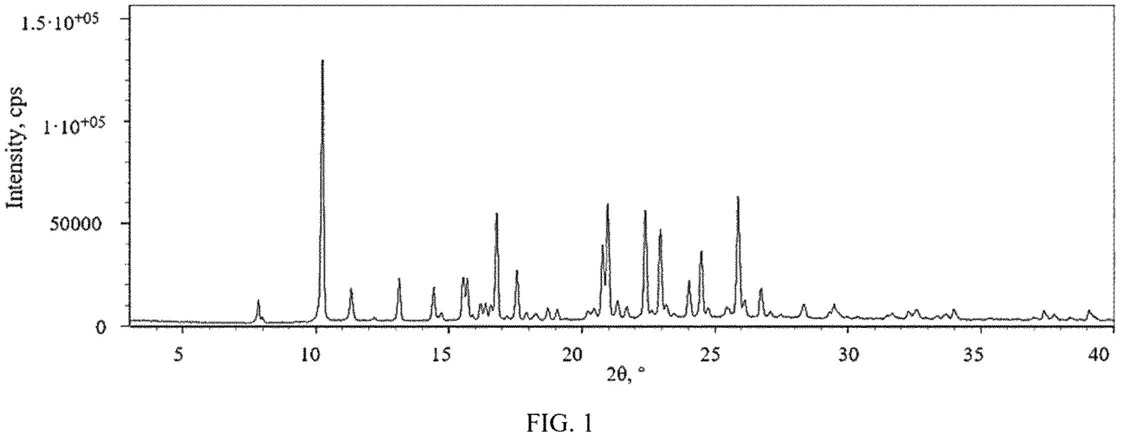
FIG. 1 shows the X-ray powder diffraction pattern of crystal form A.

The present disclosure will be described in detail below by way of examples, but the scope of the present disclosure is not limited thereto. Experimental methods that do not indicate specific conditions in the following examples should be selected according to conventional methods and conditions, or according to product specifications.

Abbreviation and Full Name Comparison Table

-continued

| Abbreviation | Full Name |
|---|---|
| API | Active Pharmaceutical Ingredient |
| AR | Analytical Reagent |
| DCM | Dichloromethane |
| DSC | Differential Scanning Calorimeter |
| DVS | Dynamic Vapor Sorption |
| EA | Ethyl Acetate |
| EtOH | Ethanol |
| FaSSIF | Fasted-State Simulated Intestinal Fluid |
| FeSSIF | Fed-State Simulated Intestinal Fluid |
| HPLC | High Performance Liquid Chromatograph |
| ICH | International Conference on Harmonisation |
| IPA | Isopropyl Alcohol |
| MeOH | Methanol |
| MW | Molecular Weight |
| NMR | Nuclear Magnetic Resonance |
| PK | Pharmacokinetics |
| PLM | Polarized Light Microscope |
| RH | Relative Humidity |
| RT | Room Temperature |
| SGF | Simulated Gastric Fluid |
| SIF | Simulated Intestinal Fluid |
| SOP | Standard Operating Procedure |
| TGA | Thermal Gravimetric Analysis |
| THF | Tetrahydrofuran |
| $T_m$ | Melting Point |
| UPLC | Ultra Performance Liquid Chromatography |
| XRPD | X-ray Powder Diffraction |

Instrument, Equipment, and Test Conditions

X-ray powder diffraction (XRPD) was performed on products of crystal forms. Approximately 10 mg of the product was placed on a glass slide, flattened, and loaded into the instrument to initiate the program. For differential scanning calorimeter (DSC), 1 to 3 mg of the sample was weighed into an aluminum pan, sealed, punctured, and then placed onto the sample platform for testing, with the program set and run. For thermal gravimetric analysis (TGA), the aluminum pan was first tared, followed by weighing 3 to 10 mg of the sample into the aluminum pan, which was then placed onto the sample platform for testing, with the program set and run. For polarized light microscope (PLM), a small amount of sample was placed on a clean glass slide, dispersed by dropping a small amount of silicone oil, placed on the instrument for adjusting the magnification and exposure intensity, observed and took photos to save the data.

| TGA- Method | |
|---|---|
| Equipment | NETZSCH; TG209 F3 |
| Temperature Range | RT-300° C. |
| Heating Rate | 10° C./min |
| $N_2$ Flow Rate | 50 mL/min |
| Type of Crucible | Aluminum Crucible |
| **DSC- Method** | |
| Equipment | NETZSCH DSC 3500 |
| Temperature Range | 30-300° C. |
| Heating Rate | 10° C./min |
| $N_2$ Flow Rate | 50 mL/min |
| Type of Crucible | Aluminum Crucible |
| **XRPD- Method** | |
| Equipment | Rigaku; MiniFlex600 |
| Radiation Source | CuKα (40 kV, 15 mA) |
| Scanning Rate | 10°/min |
| Scanning Range | 3°-40° (2θ) |

-continued

| Microscopic Examination | |
|---|---|
| Equipment | Olympus; BX53M |
| Hygroscopicity | |
| Equipment | Surface Measurement System DVS-1, 25 ± 0.5° C. |
| NMR | |
| Equipment | Bruker AVANCE III 400 M |
| HPLC-Method | |
| Chromatographic Column | YMC-Triart C18 (100 × 2.0 mm 1.9 μm) PN TA12S05-1546PTH or Waters ACQUITY UPLC@BEH C18 (100 × 2.1 mm 1.7 μm) PN 186002352 |
| Column Temperature | 40° C. |
| Mobile Phase | A: 0.05% formic acid aqueous solution; B: 0.05% formic acid acetonitrile solution |
| Detection Wavelength | 210 nm |

The counterions and solvents used in the present disclosure are shown in the following table:

| Counterions | Name | CAS No. | Molecular Weight | pKa |
|---|---|---|---|---|
| Acid | Hydrochloric Acid | 7647-01-0 | 36.46 | −6.00 |
| | Sulfuric Acid | 7664-93-9 | 98.08 | −3.00, 1.92 |
| | Galactonic Acid | 526-99-8 | 210.14 | 3.08, 3.63 |
| | D-Gluconic Acid | 526-95-4 | 196.16 | 3.76 |
| | Maleic Acid | 110-16-7 | 116.07 | 1.92, 6.23 |
| | Phosphoric Acid | 7664-38-2 | 98.00 | 1.96, 7.12, 12.32 |
| | L-Glutamic Acid | 617-65-2 | 147.13 | 4.25, 2.19, |
| | Hippuric Acid | 495-69-2 | 179 | 3.55 |
| | L-Aspartic Acid | 56-84-8 | 133.11 | 1.88, 3.65, 9.60 |
| | L-Tartaric Acid | 868-14-4 | 150.09 | 3.02, 4.36 |
| | Fumaric Acid | 110-17-8 | 116.07 | 3.03, 4.38 |
| | Acetic Acid | 64-19-7 | 60.05 | 4.76 |
| | Citric Acid | 77-92-9 | 192.12 | 3.13, 4.76 |
| | L-Malic Acid | 97-67-6 | 134.09 | 3.46, 5.10 |
| | L-Arginine | 74-79-3 | 174.20 | 13.2 |
| Base | Sodium Hydroxide | 1310-73-2 | 40.00 | ca. 14 |
| | Potassium Hydroxide | 1310-58-3 | 56.11 | ca. 14 |
| Solvent | Ethanol | 64-17-5 | 46.07 | // |
| | Ethyl Acetate | 141-78-6 | 88.11 | // |
| | Acetone | 67-64-1 | 58.08 | // |
| | Tetrahydrofuran | 109-99-9 | 72.11 | // |
| | Acetonitrile | 67-64-1 | 41.06 | // |
| | Ethanol/water = 95/5 (v/v) | // | // | // |

Example 1: Preparation of Compound

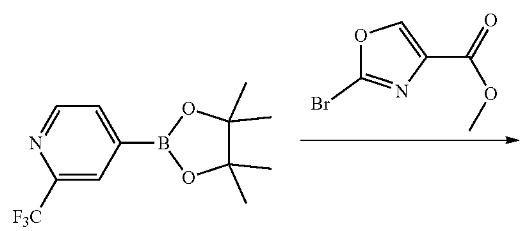

-continued

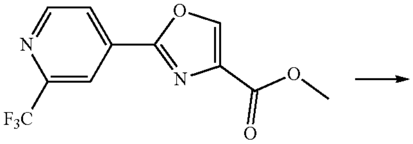

II-8-1

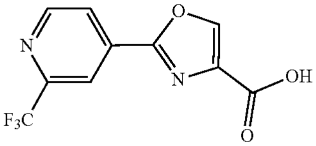

II-8-2

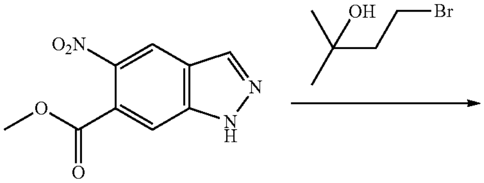

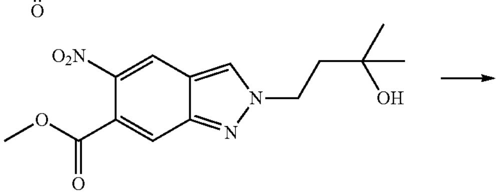

II-49-1-P2

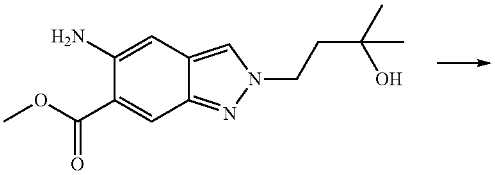

II-49-2

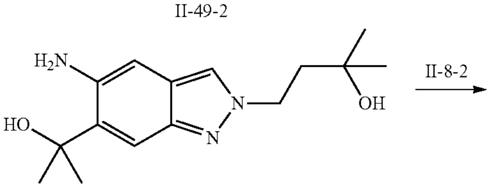

II-49-3

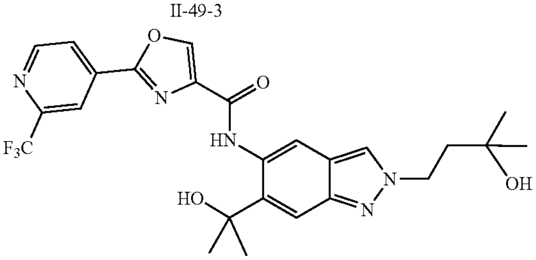

I

Step 1: Synthesis of II-8-1

A mixture of 2-(trifluoromethyl)pyridine-4-boronic acid pinacol ester (286.32 mg, 1.05 mmol), methyl 2-bromooxazole-4-carboxylate (0.18 g, 873.81 mol), Pd(dppf)$Cl_2$ (115.24 mg, 0.16 mmol), cesium carbonate (569.41 mg, 1.75 mmol), and anhydrous 1,4-dioxane (6 mL) was stirred at 80° C. under nitrogen atmosphere for 4 hours until the reaction was complete. The reaction mixture was diluted by adding $H_2O$ (10 mL) and extracted with EA (10 mL×3) under stirring. The combined organic phases were washed with brine (10 mL), dried over anhydrous $Na_2SO_4$, filtered, and concentrated under vacuum to obtain a crude product. The crude product was purified by silica gel chromatography and eluted with PE/EA=10:3 to obtain a white solid product II-8-1 (0.23 g, yield: 84.66%), MS (ESI) m/z: 272.0 $[M+H]^+$.

Step 2: Synthesis of II-8-2

To a solution of II-8-1 (0.23 g, 845.03 mol), $H_2O$ (1 mL), and THF (3 mL) was added lithium hydroxide (40.48 mg, 1.69 mmol), and the mixture was stirred at 25° C. under nitrogen atmosphere for 3 hours until the reaction was complete. The reaction mixture was diluted by adding $H_2O$ (10 mL), acidified to pH=3-4 under stirring, and extracted with EA (10 mL×3). The combined organic phases were washed with brine (20 mL), dried over anhydrous $Na_2SO_4$, filtered, and concentrated under vacuum to obtain a white solid product II-8-2 (0.2 g, crude product), MS (ESI) m/z: 259.0 $[M+H]^+$.

Step 3: Synthesis of II-49-1-P2

To a solution of methyl 5-nitro-1H-indazole-6-carboxylate (1 g, 4.52 mmol) in DMF (10 mL) were added $Cs_2CO_3$ (2.62 g, 13.56 mmol) and 4-bromo-2-methylbutan-2-ol (1.13 g, 6.78 mmol) at 25° C. The mixture was stirred at 100° C. for 16 hours until the reaction was complete. The reaction mixture was diluted with $H_2O$ (30 mL) and then extracted with EA (30 mL×3). The combined organic layers were washed with brine (30 mL×3), dried over anhydrous $Na_2SO_4$, filtered, and concentrated under reduced pressure to obtain a yellow solid crude product (6.00 g). The crude product was purified by silica gel column chromatography (PE:EtOAc=2:1) to obtain alight yellow solid product II-49-1-P2 (510.00 mg, 1.66 mmol, yield: 35.24%), MS (ESI) m/z: 308.1 $[M+H]^+$. II-49-1-P1: $^1$H NMR (400 MHz, Chloroform-d) δ 8.46 (s, 1H), 8.21 (s, 1H), 7.74 (s, 1H), 4.61 (t, J=8.0 Hz, 2H), 3.95 (s, 3H), 2.11 (t, J=8.0 Hz, 2H), 1.30 (s, 6H). II-49-1-P2: $^1$H NMR (400 MHz, Chloroform-d) δ 8.40 (s, 1H), 8.23 (s, 1H), 8.01 (s, 1H), 4.68 (t, J=8.0 Hz, 2H), 3.92 (s, 3H), 2.22 (t, J=8.0 Hz, 2H), 1.30 (s, 6H).

Step 4: Synthesis of II-49-2

To a mixture of II-49-1-P2 (0.5 g, 1.63 mmol), EtOH (6 mL), and $H_2O$ (2.5 mL) were added $NH_4Cl$ (43.00 mg, 811.32 mol) and iron powder (908.72 mg, 16.27 mmol). The mixture was stirred at 80° C. for 16 hours until the reaction was complete. The reaction mixture was diluted with $H_2O$ (20 mL) and then extracted with EA (20 mL×3). The combined organic layers were washed with brine (20 mL), dried over $Na_2SO_4$, filtered, and concentrated under reduced pressure. The yellow solid product II-49-2 (400.00 mg) was obtained, MS (ESI) m/z: 278.1 $[M+H]^+$.

Step 5: Synthesis of II-49-3

To a stirred solution of II-49-2 (400 mg, 1.44 mmol) and THF (10 mL) was added methylmagnesium chloride (539.40 mg, 7.21 mmol) at 0° C., and the mixture was stirred for another 16 hours until the reaction was complete. The reaction mixture was diluted with $H_2O$ (20 mL), adjusted to pH=7-8 with $NH_4Cl$ aqueous solution (1 M), and extracted with EA (20 mL×3). The combined organic layers were washed with brine (20 mL), dried over $Na_2SO_4$, filtered, and concentrated under reduced pressure. The crude product was subjected to reverse-phase preparative HPLC (Prep-C18, 5 μM Xbridge column, 19×150 mm, with both solvents containing 0.1% ammonium bicarbonate) to obtain a yellow oily product II-49-3 (210.00 mg, 681.42 gmol, yield: 47.24%), MS (ESI) m/z: 278.2 $[M+H]^+$.

Step 6: Synthesis of Five-Membered-Fused Six-Membered Compound Represented by Formula I To a mixture of II-8-2 (20 mg, 77.47 mol, 1.0 eq) and DCM (2 mL) were added II-49-3 (21.49 mg, 77.47 mol, 1.0 eq), 2-(7-azabenzotriazol-1-yl)-N,N,N',N'-tetramethyluronium hexafluorophosphate (HATU) (60 mg, 232.42 mol, 3.0 eq), and DIPEA (80 mg, 77.47 μmol, 1.0 eq) at 25° C. After the addition, the resulting mixture was stirred for 1 hour until the reaction was complete. The reaction mixture was concentrated to dryness under reduced pressure. The residue was diluted by adding $H_2O$ (10 mL) and extracted with EA (10 mL×3). The combined organic layers were washed with brine (10 mL), dried over anhydrous $Na_2SO_4$, filtered, and concentrated under reduced pressure to obtain a crude product. The crude product was subjected to reverse-phase preparative HPLC (Prep-C18, 5 μM Xbridge column, 19×150 mm, Waters; two mobile phase solvents (water and acetonitrile) both containing 0.1% ammonium bicarbonate) to obtain a white solid product (i.e., the five-membered-fused six-membered compound represented by formula I) (23.90 mg, 47.34 mol, yield: 61.11%, purity: 98%), MS (ESI) m/z: 518.2 $[M+H]^+$. $^1$H NMR (400 MHz, Chloroform-d) δ 11.38 (s, 1H), 8.91 (d, J=4.0 Hz, 1H), 8.71 (s, 1H), 8.45 (s, 1H), 8.30 (s, 1H), 8.14 (dd, J=4.0, 1.2 Hz, 1H), 7.90 (s, 1H), 7.68 (s, 1H), 4.57 (t, J=8.0 Hz, 2H), 2.68 (s, 1H), 2.37 (s, 1H), 2.18 (t, J=8.0 Hz, 2H), 1.79 (s, 6H), 1.31 (s, 6H).

Example 2 Evaluation of Inhibition of Kinase Activity by Compounds

The $IC_{50}$ values of the compounds for competitively binding ATP to kinases IRAK4 and FLT3 were determined using a fluorescence microfluidic mobility shift assay. The initial detection concentration of the compounds was 10 μM, with 4-fold gradient dilution to 0.38 nM, and detected in duplicate. Among them, commercially available staurosporine was used as the standard control in this experiment.

Reagent and consumable information is as follows:

IRAK4 Kinase (Carna, Cat. No. 09-145, Lot. No. 14CBS-0020 H)
FLT3 Kinase (Carna, Cat. No. 08-154, Lot. No. 07CBS-2350)
Substrate Peptide FAM-P2 (GL Biochem, Cat. No. 112394, Lot. No. P131014-XP112394)
Substrate Peptide FAM-P8 (GL Biochem, Cat. No. 112396, Lot. No. P170731-SY112396)
ATP (Adenosine Triphosphate, Sigma, Cat. No. A7699-1G, CAS No. 987-65-5)
DMSO (Dimethyl Sulfoxide, Sigma, Cat. No. D2650)
EDTA (Ethylenediaminetetraacetic Acid, Sigma, Cat. No. E5134, CAS No. 60-00-4)
Staurosporine (Selleckchem, Cat. No. S1421)
HEPES (4-(2-Hydroxyethyl)-1-piperazineethanesulfonic Acid, Gibco, Cat. No. 15630-080)
Brij-35 Solution (Polyoxyethylene Lauryl Ether, Sigma, Cat. No. B41840-100 mL)
DTT (Dithiothreitol, Sigma, Cat. No. D0632-20G)

0.2% Coating Reagent #3 (0.2% Coating Reagent, Perkin Elmer, Cat. No. 760050)

96-Well Plate (Corning, Cat. No. 3365)

384-Well Plate (Corning, Cat. No. 3573)

Experimental Operation Method:

1) FLT3 and IRAK4 kinases were dissolved in kinase buffer (50 mM HEPES pH 7.5, 10 mM $MgCl_2$, 2 mM DTT, and 0.01% Brij-35) to final concentrations of 0.9 nM, 30 nM, and 6 nM, respectively.

2) Substrate peptides FAM-P2 and FAM-P8 were mixed with ATP in the above kinase buffer, respectively. Among them, the final concentrations of the substrate peptide FAM-P2 and ATP for determining FLT3 were 3 μM and 97 μM, respectively; the final concentrations of the substrate peptide FAM-P8 and ATP for determining IRAK4 were 3 μM and 10 μM, respectively.

3) Compound dilution: Compounds were first diluted to 50 μM, followed by 4-fold gradient dilution using DMSO. Among them, the solution without compounds and kinases served as the blank control, corresponding to the "minimum value" mentioned below. The solution containing kinases, ATP, DMSO, and buffer but no compounds served as the positive control, corresponding to the "maximum value" mentioned below.

4) Kinase reaction and termination: 10 μL of kinase buffer was added to a 384-well plate containing 5 μL of the test compound, followed by incubation at room temperature for 10 minutes. Then, L of buffer containing substrate peptide and ATP was added to the 384-well plate, and the mixture was incubated at 28° C. for one hour. Subsequently, 25 μL of termination solution (100 mM HEPES pH 7.5, 50 mM EDTA, 0.2% Coating Reagent #3, and 0.015% Brij-35) was added to each well to terminate the reaction.

5) Data reading: The conversion rate data were read using the CaliperEZ Reader II instrument under the following setting conditions: downstream voltage −500 V, upstream voltage −2250 V, baseline pressure −0.5 PSI, and screening pressure −1.2 PSI.

6) Data calculation: The conversion rate data were copied from the CaliperEZ Reader II and converted into inhibition rate data, with the following calculation formula:

$$\text{Inhibition percentage (\%)} = (\text{maximum value} - \text{conversion rate}) / (\text{maximum value} - \text{minimum value}) * 100\%$$

$IC_{50}$ values were fitted using XLFit excel add-in version 5.4.0.8, with the fitting formula:

$$Y = \text{Bottom} + (\text{Top} - \text{Bottom}) / \left(1 + \left(IC_{50}/X\right) \wedge HillSlope\right)$$

The kinase activity data for the compound are shown below:

| FLT3 $IC_{50}$ (nM) | IRAK4 $IC_{50}$ (nM) |
|---|---|
| 2.2 | 2.7 |

Example 3 Determination of $IC_{50}$ Values for Compound's Killing Activity Against MV4-11 Cells Reagent and consumable information is as follows:

MV4-11 Cells (ATCC, Cat. No. CRL-9591)

DPBS (Dulbecco's Phosphate Buffered Saline, Biosera, Cat. No. LM-S2041/500)

IMDM Medium (Thermo, Cat. No. 12440053)

Fetal Bovine Serum (Biological, Cat. No. 04-002-1A)

Penicillin-Streptomycin Solution (Invitrogen, Cat. No. 15140122)

Dimethyl Sulfoxide (Sigma, Cat. No. D2650)

CellTiter-Glo Luminescent Cell Viability Assay (Promega, Cat. No. G7573)

96-Well Plate (Corning, Cat. No. 3903)

CTG Experimental Steps

1. MV-4-11 cells were cultured in a complete IMDM medium (IMDM+10% fetal bovine serum+1% Penicillin-Streptomycin, a mixture of penicillin and streptomycin).
2. MV-4-11 cells with good cell status were collected and washed twice with DPBS (Dulbecco's phosphate buffered saline).
3. MV-4-11 cells were resuspended in a complete IMDM medium, adjusted to a cell density of $1.11 \times 10^6$ cells/mL, and 90 μL of the mixture was added to each well of a 96-well plate.
4. A 10-fold concentration of the compound solution was prepared in a complete IMDM medium, and 10 μL of the 10-fold concentration of the compound solution was added to each well of the 96-well plate. After mixing well, the 96-well plate was incubated in a 37° C., 5% $CO_2$ incubator for 72 hours.
5. After the incubation, the 96-well plate was removed and equilibrated at room temperature for 30 minutes. Then, 100 μL of CellTiter-Glo reagent was added to each well and mixed on a horizontal shaker for 2 minutes.
6. The 96-well plate was removed and equilibrated at room temperature for 10 minutes, and then the chemiluminescence value was measured using a microplate reader.

Conclusion: The cell killing activity data of the compound against MV4-11 shows that the $IC_{50}$ value is 21 nM.

Example 4 Preparation of Crystal Form 4.1 Preparation of Crystal Form A 1 g of the five-membered-fused six-membered compound represented by formula I prepared in Example 1 was weighed into a reaction vessel, followed by the addition of 5V DMSO/IPA (volume ratio 2:1, where V represents 1 mL of solvent per 1 g of solute). The mixture was heated to 65° C. with stirring to obtain a clear solution. The solution was then cooled to 50° C. and stirred for 0.5 hours. Subsequently, 18.3V IPA was added at 50° C., and the reaction was carried out for 3 hours. The temperature was further reduced to 20° C. at a rate of 10° C./hour, followed by stirring at 20° C. overnight (approximately 16 hours) to obtain a solid. The filter cake was washed with 2V IPA and vacuum-dried at 50° C. to obtain crystal form A of the free base.

4.2 Preparation of Crystal Form B 30 mg of the five-membered-fused six-membered compound represented by formula I prepared in Example 1 was weighed and added with 0.6 mL of methanol. The mixture was suspended at room temperature for 3 days, followed by filtration to obtain crystal form B as a solid.

4.3 Preparation of Crystal Form C 30 mg of the five-membered-fused six-membered compound represented by formula I prepared in Example 1 was weighed and added with 0.6 mL of acetone/water (95/5, v/v). The mixture was suspended at room temperature for 3 days, followed by filtration to obtain crystal form C as a solid.

4.4 Preparation of Crystal Form D 30 mg of the five-membered-fused six-membered compound represented by formula I prepared in Example 1 was weighed and added with 0.6 mL of methanol. The mixture was suspended at room temperature for 3 days, filtered to obtain a saturated solution, and then slowly volatilized at room temperature to obtain crystal form D as a solid.

4.5 Preparation of Crystal Form E 30 mg of the five-membered-fused six-membered compound represented by formula I prepared in Example 1 was weighed and added with 0.6 mL of ethanol. The mixture was suspended at room temperature for 3 days, filtered to obtain a saturated solution, and then slowly volatilized at room temperature to obtain crystal form E as a solid.

4.6 Preparation of Crystal Form F 30 mg of the five-membered-fused six-membered compound represented by formula I prepared in Example 1 was weighed and added with 0.6 mL of acetone-water (95/5, v/v). The mixture was suspended at room temperature for 3 days, filtered to obtain a saturated solution, and then slowly volatilized at room temperature to obtain crystal form F as a solid.

4.7 Preparation of Crystal Form G 30 mg of the five-membered-fused six-membered compound represented by formula I prepared in Example 1 was weighed and added with 0.6 mL of methanol. The mixture was dissolved completely at 70° C., then cooled to 5° C. at a rate of 5° C. per hour. The suspension was filtered to obtain crystal form G as a solid.

Example 5 Simulated Granulation Test

Dry method: Crystal form A of the five-membered-fused six-membered compound represented by formula I was directly ground for 30 minutes.

Wet method: The granulation solvent ethanol was added dropwise to the surface of crystal form A of the five-membered-fused six-membered compound represented by formula I until the solid was sufficiently wetted, followed by grinding for 30 minutes. The resulting solids were then characterized by XRPD, DSC, and the like to evaluate the solid crystal form and crystallinity. The purpose was to determine whether polymorphs, solvates, or amorphous forms were readily generated. The simulated granulation experiment results show that the crystal forms have not changed and are all crystal form A, and no new crystal forms have been found.

Example 6 High-Pressure Property Test

Approximately 10 mg of crystal form A of the five-membered-fused six-membered compound represented by formula I was weighed, placed into a 13 mm diameter hydraulic disc, and subjected to high-pressure property test using a manual hydraulic press with a hydraulic pressure of 10 tons and a compression duration of 5 minutes. The resulting solid was characterized by XRPD and other methods to evaluate its crystal form stability under high-pressure conditions. As can be seen from the results of the high-pressure treatment experiment, the crystal form has not changed and is crystal form A, and no new crystal form has been found.

Example 7 Study on Crystal Form Transformation Relationship

In order to study the transformation relationship between various crystal forms and prepare various crystal forms under repeated conditions, a series of suspension competition experiments were carried out on crystal forms A, C, D, E, and G in different solvent systems. The specific experimental steps are as follows:

20 mg of each of crystal forms A, C, D, E, and G were weighed into 5 mL glass vials, and solvents ($EtOH/H_2O$=1/1 (v/v) or DMSO (dimethyl sulfoxide)/EtOH=1/8 (v/v)) were added to form suspensions. The vials were then transferred to 25° C. and stirred for 72 hours. At various time points, the filter cakes were tested by XRPD.

$EtOH/H_2O$ 1/1 Solvent System

TABLE 1

Suspension Competition in $EtOH/H_2O$ 1/1 Solvent System

| Starting Material (20 mg) | Solvent | T(° C.) | Phenomenon | Time | XRPD |
|---|---|---|---|---|---|
| Crystal Form A | $EtOH/H_2O$ | RT | Suspension | 24 hours | Crystal Form C |
| Crystal Form C | 1/1 (v/v) | | | | |
| Crystal Form D | (Saturated | | | 48 hours | Crystal Form C |
| Crystal Form E | Solution) | | | 72 hours | Crystal Form C |
| Crystal Form G | 15 V | | | | |

From the suspension experiment of $EtOH/H_2O$ 1/1 solvent system, it can be seen that after 24 hours of suspension, the solid sample is crystal form C.

DMSO/EtOH 1/8 Solvent System

TABLE 2

Suspension Competition in DMSO/EtOH 1/8 Solvent System

| Starting Material (20 mg) | Solvent | T(° C.) | Phenomenon | Time | XRPD |
|---|---|---|---|---|---|
| Crystal Form A<br>Crystal Form C<br>Crystal Form D<br>Crystal Form E<br>Crystal Form G | DMSO/EtOH<br>1/8 (v/v)<br>(Saturated Solution)<br>15 V | RT | Suspension | 24 hours<br><br>48 hours<br>72 hours | Crystal Form A<br><br>Crystal Form A<br>Crystal Form A |

From the suspension experiment of DMSO/EtOH 1/8 solvent system, it can be seen that after 24 hours of suspension, the solid sample is crystal form A.

Example 8 Various Crystal Form Product Analysis

The products obtained from the various crystal form screening were subjected to X-ray powder diffraction (XRPD), differential scanning calorimetry (DSC), thermal gravimetric analysis (TGA), high performance liquid chromatography (HPLC) and other tests, and the new crystal forms that emerged were summarized. The relevant spectra are shown in FIGS. 1 to 14.

TABLE 3

Various Crystal Form Characterization Analysis

| Type | Characterization | Purity |
|---|---|---|
| Crystal Form A | TGA: Weight Loss of 0.428% at 200.0° C.;<br>DSC: 231.31° C., 111.30 J/g | 99.70% |
| Crystal Form B | TGA: Weight Loss of 4.741% at 122.68° C.;<br>DSC: 60.85° C., 32.752 J/g<br>151.04° C., 4.135 J/g<br>230.51° C., 113.95 J/g | 99.64% |
| Crystal Form C | TGA: Weight Loss of 3.778% at 73.91° C.;<br>DSC: 63.69° C., 61.396 J/g<br>126.27° C., 42.089 J/g<br>230.61° C., 103.46 J/g | 99.98% |
| Crystal Form D | TGA: Weight Loss of 2.826% at 116.38° C.;<br>DSC: 150.88° C., 15.721 J/g<br>231.13° C., 115.52 J/g | 99.73% |
| Crystal Form E | TGA: Weight Loss of 5.585% at 119.49° C.;<br>DSC: 48.59° C., 5.451 J/g<br>90.07° C., 19.797 J/g<br>225.15° C., 86.445 J/g | 97.43% |

TABLE 3-continued

Various Crystal Form Characterization Analysis

| Type | Characterization | Purity |
|---|---|---|
| Crystal Form F | TGA: Weight Loss of 1.066% at 127.37° C.;<br>DSC: 49.64° C., 3.400 J/g<br>97.99° C., 9.028 J/g<br>225.07° C., 92.201 J/g | 97.10% |
| Crystal Form G | TGA: Weight Loss of 3.405% at 130.90° C.;<br>DSC: 63.20° C., 25.610 J/g<br>150.82° C., 12.882 J/g<br>230.69° C., 111.38 J/g | 98.75% |

From the experimental results, it can be concluded that among the seven crystal forms found, crystal form A has a high melting point and a small weight loss.

Example 9 Solid-State Stability Study—Influencing Factor Test

To evaluate the solid-state stability of crystal form A, it was placed under various conditions to investigate changes in crystal form, purity, and color.

60 mg of crystal form A was weighed and placed in a glass dish or a glass vial. The glass dish or glass vial was then subjected to different environments in a constant temperature and humidity chamber. The conditions include: illumination: 4500±500 Lux; high temperature: 60° C. (sealed); and high humidity: 25° C. with relative humidity RH=90±5% (open). The solid-state stability study results for crystal form A are shown in the following table:

TABLE 4

Solid-State Stability Study

| | | 5 Days | | | 11 Days | | |
|---|---|---|---|---|---|---|---|
| Crystal Form | Environmental Conditions | XRPD | Purity | Color Change | XRPD | Purity | Color Change |
| Crystal Form A 99.70% | Strong Illumination (Open) | No Change | 99.67% | No Change | No Change | 99.44% | No Change |
| | High Temperature (60° C., Sealed) | No Change | 99.26% | No Change | No Change | 99.67% | No Change |
| | High Relative Humidity (RH = 90 ± 5%, Open, 25° C.) | No Change | 99.60% | No Change | No Change | 99.56% | No Change |

The experimental results of solid-state stability evaluation show that crystal form A has good physical and chemical properties under the conditions of high temperature, high humidity, and strong illumination.

Example 10 Hygroscopicity Study

Figure 15:
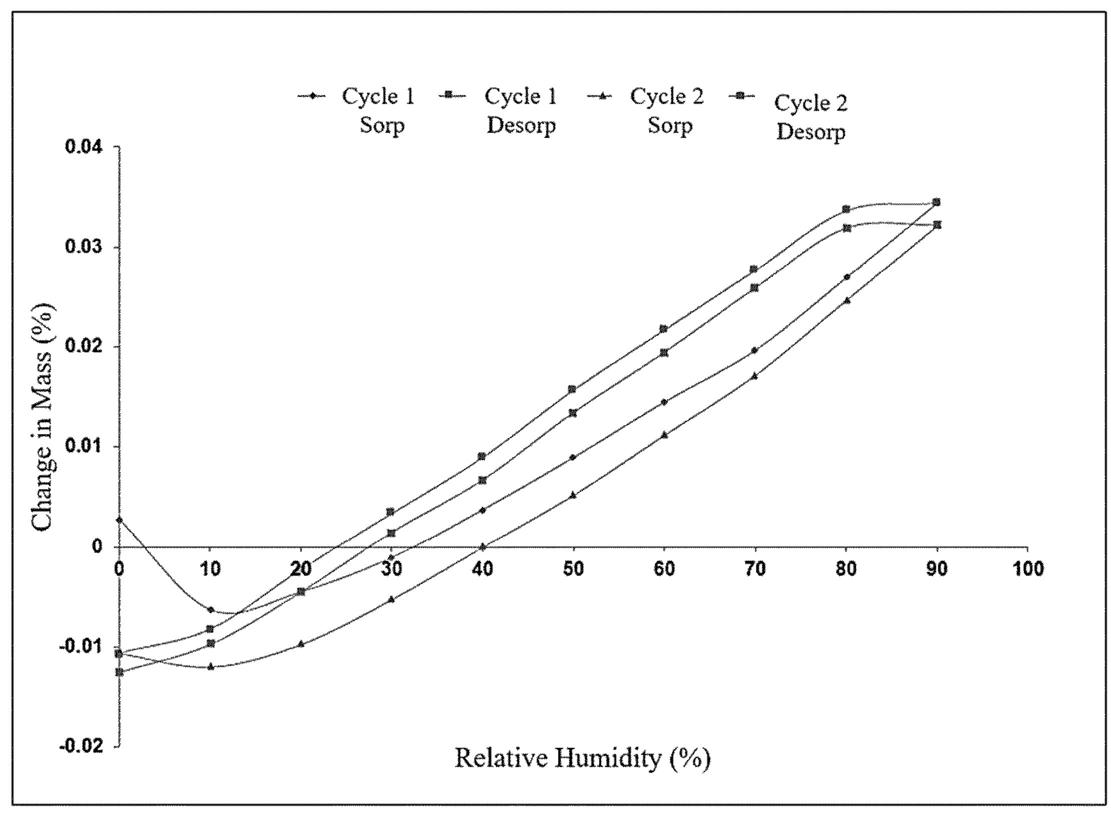
FIG. 15 shows the dynamic vapor sorption (DVS) pattern of crystal form A for hygroscopicity test.
Figure 16:
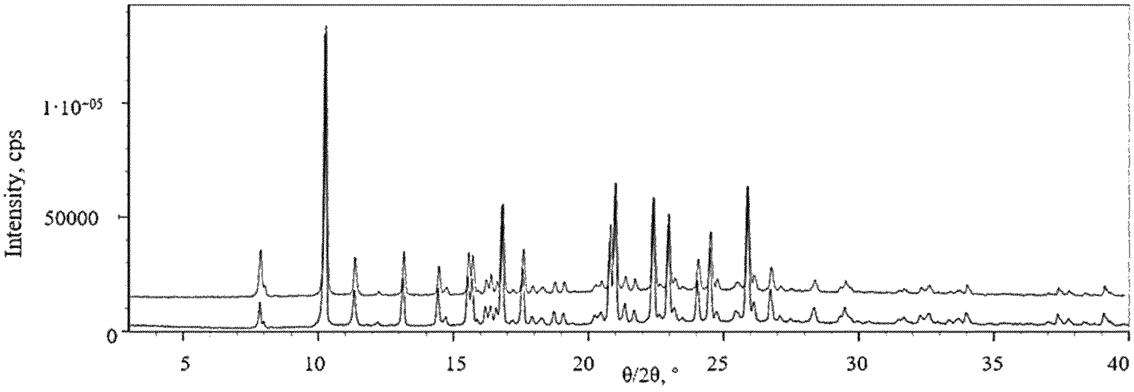
FIG. 16 shows the X-ray powder diffraction patterns of crystal form A before and after hygroscopicity test.

The important hygroscopicity of this compound was tested using a dynamic vapor sorption (DVS) instrument. DVS is a dynamic measurement method, so during the measurement process, the sample will undergo a change in mass. Like other types of research methods, DVS records the change in mass of the sample as the relative humidity changes. The relevant spectra are shown in FIGS. 15-16. From the DVS curve results in FIG. 15, it can be seen that the moisture sorption of the two sorption-desorption curves of the initial sample at 25° C./90° 0 RH (relative humidity) is less than 0.0400, indicating that the sample has low hygroscopicity.

TABLE 5

Hygroscopicity Study

| | Crystal Form A Moisture Sorption of 0.03% at 90% RH | | | |
|---|---|---|---|---|
| | Sorption (%) | Desorption (%) | Sorption (%) | Desorption (%) |
| 0% | 0.00 | −0.01 | −0.01 | −0.01 |
| 10% | −0.01 | 0.00 | −0.01 | −0.01 |
| 20% | 0.00 | 0.00 | −0.01 | 0.00 |
| 30% | 0.00 | 0.00 | −0.01 | 0.00 |
| 40% | 0.00 | 0.01 | 0.00 | 0.01 |
| 50% | 0.01 | 0.02 | 0.01 | 0.01 |
| 60% | 0.01 | 0.02 | 0.01 | 0.02 |
| 70% | 0.02 | 0.03 | 0.02 | 0.03 |
| 80% | 0.03 | 0.03 | 0.02 | 0.03 |
| 90% | 0.03 | 0.03 | 0.03 | 0.03 |

Conclusion: The samples before and after DVS testing were subjected to XRPD test. As shown in FIG. 16, no change in crystal form is observed.

Example 11 Preparation of Salt Form

The free base contains multiple basic sites, and inorganic/organic acids and free bases commonly used in drug research were selected for salt formation studies. During the research process, 9 salt forms such as hydrochloride salt, sulfate salt, and phosphate salt were prepared. The experimental process of salt formation research is summarized as follows:

(1) API (i.e., five-membered-fused six-membered compound of formula I prepared in Example 1) (30 mg) and solvent (0.3 mL) were put into a reaction vial. The reaction system was stirred at room temperature (approximately 25° C.) to obtain a clear solution or suspension system.

(2) The counterion reagent (1.1 eq or 3.0 eq) and solvent (0.3 mL) were first added to the reaction vial, and a clear solution or suspension system was obtained under stirring at room temperature. This system was then slowly added to the clear solution or suspension system in (1) under stirring.

(3) The reaction system was heated to 50° C. and stirred at 50° C. for 2 hours.

(4) The reaction system was cooled to 25° C. at a rate of 10° C./hour and maintained for 15 hours.

(5) The suspended reaction system was centrifuged, and the filter cake was vacuum-dried at room temperature for 15 hours. For reaction systems without solid precipitation, nitrogen purging was performed at 25° C., and the solvent was volatilized to obtain solid samples. The results are as follows:

| | Solvent | | | | | |
|---|---|---|---|---|---|---|
| Counterion | Ethanol | Ethyl Acetate | Acetone | Tetrahydrofuran | Acetonitrile | Ethanol/Water = 95/5(v/v) |
| Hydrochloric Acid | Unsalted | HC-Crystal Form A | HC-Crystal Form A | HC-Crystal Form A | HC-Crystal Form A | Unsalted |
| Sulfuric Acid (98%) | Unsalted | SF-Crystal Form A | SF-Crystal Form A | SF-Crystal Form B | SF-Crystal Form A | Unsalted |
| Phosphoric Acid | Unsalted | PH-Crystal Form A | Unsalted | PH-Crystal Form B | PH-Crystal Form A | Unsalted |
| Fumaric Acid | | | | Unsalted | | |
| L-Tartaric Acid | | | | Unsalted | | |
| Maleic Acid | | | | Unsalted | | |
| Citric Acid | | | | Unsalted | | |
| Hippuric Acid | | | | Unsalted | | |
| L-Glutamic Acid | | | | Unsalted | | |
| L-Aspartic Acid | | | | Unsalted | | |
| Hydrochloric Acid (3.0 eq) | // | HC-Crystal Form A | HC-Crystal Form A | HC-Crystal Form A | HC-Crystal Form B | Unsalted |
| Sulfuric Acid (98%) (3.0 eq) | // | // | SF-Crystal Form A | Amorphous | SF-Crystal Form C | // |
| Phosphoric Acid (3.0 eq) | Unsalted | PH-Crystal Form A | Unsalted | PH-Crystal Form B | PH-Crystal Form A | Unsalted |
| 10% Sodium Hydroxide (Aqueous Solution) (1.1 eq) | Unsalted | Unsalted | NA-Crystal Form A* | NA-Crystal Form A* | Unsalted | NA-Crystal Form A |

-continued

| Counterion | Solvent | | | | | |
|---|---|---|---|---|---|---|
| | Ethanol | Ethyl Acetate | Acetone | Tetrahydrofuran | Acetonitrile | Ethanol/Water = 95/5(v/v) |
| 10% Potassium Hydroxide (Aqueous Solution) (1.1 eq) | Unsalted | Unsalted | KA-Crystal Form A* | KA-Crystal Form A* | Unsalted | Unsalted |
| L-Arginine (1.1 eq) | Unsalted | | | | | |
| Galactonic Acid | Unsalted | | | | | |
| D-Gluconic Acid | Unsalted | | | | | |
| L-Malic Acid | Unsalted | | | | | |
| Acetic Acid | Unsalted | | | | | |

Note:

Samples marked with "*" represent solids obtained by volatilization of clear solutions under nitrogen atmosphere, and "//" represents that no volatilization is performed or a small amount of solids is obtained.

In the table, HC represents hydrochloride salt, SF represents sulfate salt, PH represents phosphate salt, NA represents sodium salt, and KA represents potassium salt.

Based on the 9 different salt forms that could be obtained, and according to the XRPD, TGA, and DSC characterization results, and a comprehensive comparison of the crystallinity, melting point, and TGA weight loss of the salts, crystal form A of hydrochloride salt (HC-crystal form A), crystal form A of sulfate salt (SF-crystal form A), and crystal form A of phosphate salt (PH-crystal form A) were selected as the dominant salt forms for subsequent solid-state stability tests and DVS hygroscopicity studies.

Example 12 Detection of Salt Form 5.1 Experimental Purpose:

Determination of the content of chloride ions, sulfate ions, and phosphate ions in crystal form A of hydrochloride salt, crystal form A of sulfate salt, and crystal form A of phosphate salt by ion chromatography 5.2 Instrument and Equipment:

| Instrument Name | Manufacturer | Instrument Model | Instrument Code |
|---|---|---|---|
| Ion Chromatograph | Thermo | ICS-6000 | PA-A-IC-02 |
| Electronic Balance | Mettler | XSE205DU | GD-BL-01 |
| Pure Water Meter | Millipore | IQ7000 + Elix Essential | PA-A-CSY-02 |

5.3 Reagents and Materials:

| Name | Manufacturer | Content/% | Specification |
|---|---|---|---|
| Sulfuric Acid ($H_2SO_4$) | Nanjing Chemical Reagent | 98.0% | Analytically Pure |
| Hydrochloric Acid (HCl) | Nanjing Chemical Reagent | 36.5% | Analytically Pure |
| Phosphoric Acid ($H_3PO_4$) | Aladdin | 90.0% | Chromatographic Grade |
| Ethyl Acetate (EtOAc) | Aladdin | N/A | Chromatographic Grade |
| Methyl tert-Butyl Ether (MTBE) | Aladdin | N/A | Chromatographic Grade |
| Dionex EGC 500 KOH Eluent Generator Cartridge Potassium Hydroxide | Thermo | N/A | N/A |

5.4 Sample Configuration:

| Solution Name | Sample Name | Sample Weight/Volume | Dilution Volume/mL | Diluent | Remarks |
|---|---|---|---|---|---|
| Reference Stock Solution | HCl | 61.68 mg | 5 | $H_2O$ | N/A |
| | $H_2SO_4$ | 65.54 mg | | | |
| | $H_3PO_4$ | 50.89 mg | | | |
| Reference Solution (STD) | Reference Stock Solution | 250 µL | 50 | $H_2O$ | N/A |
| Blank | N/A | N/A | N/A | $H_2O$ | |

SPL-$Cl^-$: Accurately 15.65 mg of crystal form A of hydrochloride salt sample was weighed into a 15 mL plastic centrifuge tube. Accurately 8.0 mL of pure water was added first, followed by 7.0 mL of ethyl acetate. The mixture was sonicated until completely dissolved, and then allowed to stand for phase separation. The upper organic phase was aspirated. Subsequently, 1.0 mL of methyl tert-butyl ether was added to the aqueous phase, thoroughly mixed by shaking, and allowed to stand for phase separation. Accurately 1.0 mL was removed from the aqueous phase into a 5 mL volumetric flask, labeled as SPL-$Cl^-$.

SPL-$SO_4^{2-}$: Accurately 16.70 mg of crystal form A of sulfate salt sample was weighed into a 15 mL plastic centrifuge tube. Accurately 8.0 mL of pure water was added first, followed by 7.0 mL of ethyl acetate. The mixture was sonicated until completely dissolved, and then allowed to stand for phase separation. The upper organic phase was aspirated. Subsequently, 1.0 mL of methyl tert-butyl ether was added to the aqueous phase, thoroughly mixed by shaking, and allowed to stand for phase separation. Accurately 1.0 mL was removed from the aqueous phase into a 5 mL volumetric flask, labeled as SPL-$SO_4^{2-}$ SPL-$PO_4^{3-}$: Accurately 13.81 mg of crystal form A of phosphate salt sample was weighed into a 15 mL plastic centrifuge tube. Accurately 8.0 mL of pure water was added first, followed by 7.0 mL of ethyl acetate. The mixture was sonicated until completely dissolved, and then allowed to stand for phase separation. The upper organic phase was aspirated. Subsequently, 1.0 mL of methyl tert-butyl ether was added to the aqueous phase, thoroughly mixed by shaking, and allowed to stand for phase separation. Accurately 1.0 mL was removed from the aqueous phase into a 5 mL volumetric flask, labeled as SPL-$PO_4^{3-}$.

5.5 Method Parameters:

| | |
|---|---|
| Chromatographic Column | Dionex Ionpac AS11-HC (250 mm * 4 mm) |
| | Dionex IonPac AG11-HC (50 mm * 4 mm) |
| Flow rate | 1.2 mL/min |
| Mobile Phase | KOH |
| Suppression Current | 100 mA |
| Column Temperature | 35° C. |
| Detector Cell Temperature | 35° C. |
| Acquisition Time | 15 min |
| Injection Volume | 25 µL |

| Gradient | Time/min | KOH Concentration/(mmol/L) |
|---|---|---|
| | Initial | 30 |
| | 15 | 30 |

5.6 Experimental Results

| | Name | Weight/ mg | Volume/ mL | Concen-tration/ mg/mL | Peak Area | Response Factor (RF) | Content/ (w/w %) |
|---|---|---|---|---|---|---|---|
| STD | $Cl^-$ | 61.68 | 1000 | 0.06168 | 5.5862 | 90.56744488 | N/A |
| | $SO_4^{2-}$ | 65.548 | 1000 | 0.065548 | 11.1764 | 170.5071093 | |
| | $PO_4^{3-}$ | 50.89 | 1000 | 0.05089 | 3.3102 | 65.04617803 | |
| SPL | SPL-$Cl^-$ | 15.65 | 40 | 0.39125 | 5.7719 | 14.75246006 | 5.95 |
| | SPL-$SO_4^{2-}$ | 16.70 | 40 | 0.4175 | 11.381 | 27.25988024 | 15.67 |
| | SPL-$PO_4^{3-}$ | 13.81 | 40 | 0.34525 | 3.7381 | 10.82722665 | 14.98 |

Calculation:

The molar ratio of chloride ion to free base in hydrochloride salt=(5.95/35.5)/(100/(517.5+36.5))=0.93:1

The molar ratio of sulfate ion to free base in sulfate salt=(15.67/96)/(100/(517.5+98))=1:1

The molar ratio of phosphate ion to free base in the phosphate salt=(14.98/95)/(100/(517.5+98))=0.97:1

Conclusion: It has been verified that the acid-base ratio in the salts obtained above is 1:1.

Example 13 Crystal Form Characterization

The solid-state substances of the screened salt forms were characterized by differential scanning calorimetry (DSC), thermal gravimetric analysis (TGA), X-ray powder diffraction (XRPD), and other methods. The crystallinity, TGA weight loss, melting point, HPLC purity, and other results of the salt form screened were comprehensively considered, and the dominant salt form was selected for scaled-up preparation.

The solid-state properties of the screened salt forms were characterized by differential scanning calorimetry (DSC), thermal gravimetric analysis (TGA), X-ray powder diffraction (XRPD), and other methods. The relevant spectra are shown in FIGS. 17 to 34. Experimental results are as follows:

| Salt | | TGA | DSC (° C.) | PLM | HPLC |
|---|---|---|---|---|---|
| Hydrochloride Salt | Crystal Form A | Weight Loss of 2.1% at 125.0° C. | 184.0° C. | Fine Granular | 99.68% |
| | Crystal Form B | Weight Loss of 10.1% at 96.4° C. | 66.5° C. 101.1° C. 132.4° C. 173.5° C. | Fine Granular | 99.79% |
| Sulfate Salt | Crystal Form A | Weight Loss of 3.9% at 118.5° C. | 67.6° C. 149.9° C. | Fine Granular | 99.47% |
| | Crystal Form B | Weight Loss of 6.9% at 92.0° C. | 30.0° C. 126.3° C. | Fine Granular | 98.64% |
| | Crystal Form C | Weight Loss of 10.5% at 102.2° C. | 50.5° C. 117.3° C. 139.5° C. 167.2° C. | Fine Granular | 94.58% |
| Phosphate Salt | Crystal Form A | Weight Loss of 0.8% at 142.9° C. | 179.8° C. | Fine Granular | 99.77% |
| | Crystal Form B | Weight Loss of 1.1% at 74.5° C. | 31.5° C. 90.8° C. 128.0° C. 160.0° C. | Fine Granular | 99.83% |
| Sodium Salt | Crystal Form A | Weight Loss of 6.3% at 116.9° C. | 126.6° C. 228.6° C. | Fine Granular | 99.19% |
| Potassium Salt | Crystal Form A | Weight Loss of 8.4% at 184.0° C. | 65.2° C. 217.8° C. | Fine Granular | 96.58% |

Example 14 Solid-State Stability Test 60 mg each of crystal form A of hydrochloride salt, crystal form A of sulfate salt, and crystal form A of phosphate salt were weighed and placed in glass dishes or glass vials. The glass dishes or glass vials were then placed in different environments of the constant temperature and humidity chamber, with conditions including: illumination: 4500±500 Lux (open); high temperature: 60° C. (sealed), high humidity: 25° C. with RH=90±5% (open).

The solid-state stability study results for the phosphate salt, hydrochloride salt, and sulfate salt are shown below:

| | Salt Type | Purity | Color Change |
|---|---|---|---|
| Initial State | | | |
| | Crystal Form A of Phosphate Salt | 99.18% | White |
| | Crystal Form A of Hydrochloride Salt | 98.53% | White |
| | Crystal Form A of Sulfate Salt | 99.12% | White |
| Crystal Form A of Phosphate Salt, 5 Days | | | |
| Strong Illumination (Open) | No Change | 99.67% | No Change |
| High Temperature (60° C., Sealed) | No Change | 99.49% | Turn Yellow |
| High Relative Humidity (RH = 90 ± 5%, Open, 25° C.) | No Change | 99.66% | No Change |

-continued

| | Salt Type | Purity | Color Change |
|---|---|---|---|
| Crystal Form A of Hydrochloride Salt, 5 Days | | | |
| Strong Illumination (Open) | No Change | 99.68% | No Change |
| High Temperature (60° C., Sealed) | No Change | 99.64% | No Change |
| High Relative Humidity (RH = 90 ± 5%, Open, 25° C.) | No Change | 99.65% | No Change |
| Crystal Form A of Sulfate Salt, 5 Days | | | |
| Strong Illumination (Open) | No Change | 99.35% | No Change |
| High Temperature (60° C., Sealed) | No Change | 99.74% | Turn Yellow |
| High Relative Humidity (RH = 90 ± 5%, Open, 25° C.) | No Change | 99.08% | Turn Yellow |
| Crystal Form A of Phosphate Salt, 11 Days | | | |
| Strong Illumination (Open) | No Change | 99.01% | No Change |
| High Temperature (60° C., Sealed) | No Change | 99.49% | Turn Yellow |
| High Relative Humidity (RH = 90 ± 5%, Open, 25° C.) | No Change | 99.33% | No Change |
| Crystal Form A of Hydrochloride Salt, 11 Days | | | |
| Strong Illumination (Open) | No Change | 99.56% | No Change |
| High Temperature (60° C., Sealed) | No Change | 99.48% | No Change |
| High Relative Humidity (RH = 90 ± 5%, Open, 25° C.) | No Change | 99.79% | No Change |
| Crystal Form A of Sulfate Salt, 11 Days | | | |
| Strong Illumination (Open) | No Change | 99.26% | No Change |
| High Temperature (60° C., Sealed) | No Change | 98.39% | Turn Yellow |
| High Relative Humidity (RH = 90 ± 5%, Open, 25° C.) | No Change | 99.14% | Turn Yellow |

The results of the solid-state stability evaluation test show that the crystal form A of hydrochloride salt exhibits good physical and chemical stability under strong illumination, high temperature, and high humidity conditions.

Example 15 Solubility Test

The solubility of dominant salts in different pH buffers, water, and physiological solutions was determined. The specific steps for solubility determination are as follows:

15 mg of crystal form A of hydrochloride salt sample was accurately weighed and transferred to a 20 mL threaded vial; 3 mL of solution (water, pH buffer, SGF, FaSSIF, FeSSIF) was added to each vial respectively. The vials were sealed, transferred to a magnetic stirrer, and maintained at 25° C. with a stirring rate of 500 rpm for 24 hours. The dissolution status in sample vials was recorded during the test. After 24 hours, approximately 1 mL of the suspension was filtered, and the filtrate was collected for solubility test via HPLC analysis. The pH value of the filtrate sample was measured using a pH meter. Crystal form A of phosphate salt and crystal form A of sulfate salt were determined following the above operation.

The experimental results are summarized as shown in the table below:

| | Solubility at 25° C. | | |
|---|---|---|---|
| Buffer | Crystal Form A of Phosphate Salt | Crystal Form A of Hydrochloride Salt | Crystal Form A of Sulfate Salt |
| pH = 1.0 | 0.16 μg/mg | 172.73 μg/mL | 179.03 μg/mL |
| pH = 6.8 | <LOD | <LOD | <LOD |
| FeSSIF (pH = 5.0) | <LOD | 7.86 μg/mL | 19.45 μg/mL |
| FaSSIF (pH = 6.5) | <LOD | 2.09 μg/ml | <LOD |
| SGF (pH = 1.2) | <LOD | 2.20 μg/mL | 2.88 μg/mL |
| Water | <LOD | <LOD | 1.34 μg/mL |

The results show that all the crystal forms have good solubility in the buffer with pH=1.

Example 16 DVS Test

Experimental Method

Figure 35:
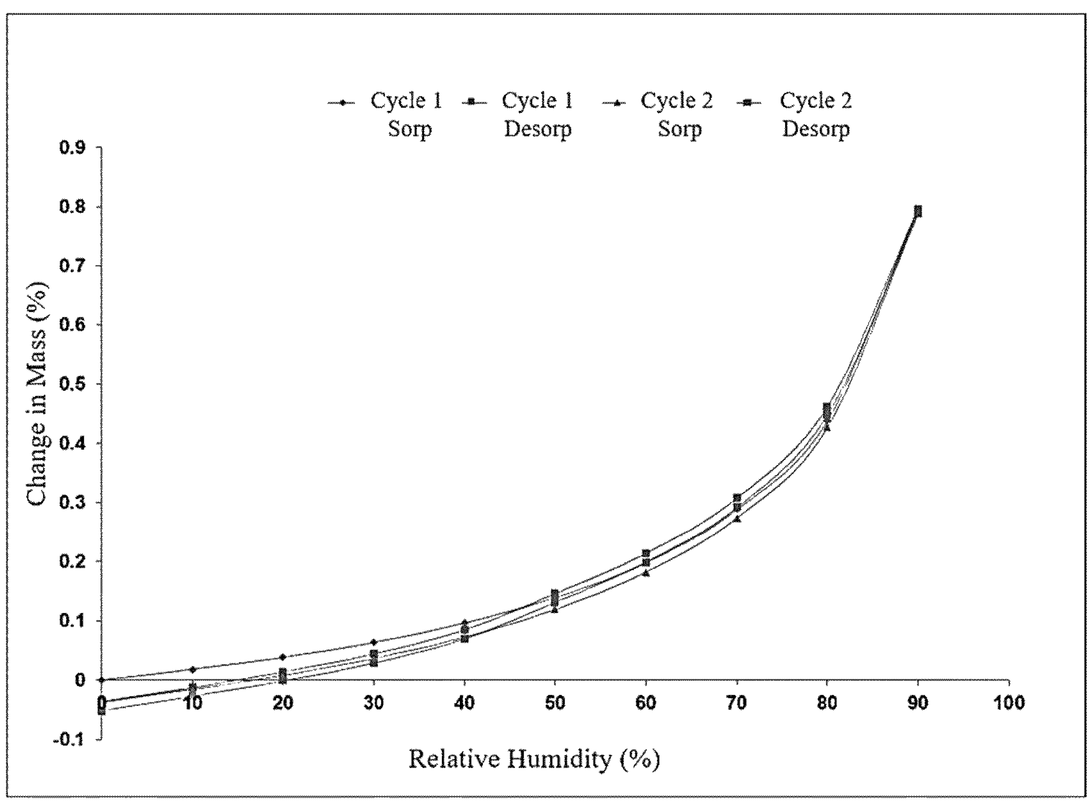
FIG. 35 shows the dynamic vapor sorption (DVS) pattern of the phosphate salt.
Figure 36:
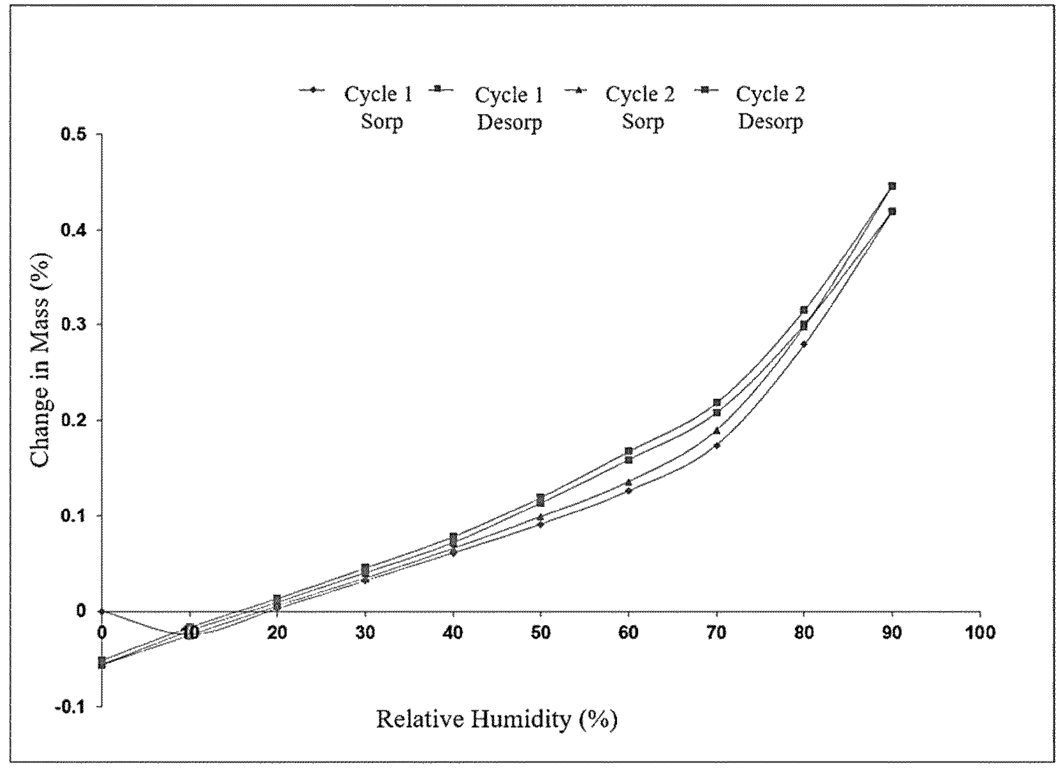
FIG. 36 shows the dynamic vapor sorption (DVS) pattern of the hydrochloride salt.

1. The instrument sample pan was first tared and balanced.
2. 30 mg of each sample (crystal form A of phosphate salt and crystal form A of hydrochloride salt) was weighed and placed on the sample pan respectively.
3. The program was run: starting from 0% humidity as the initial point, slowly increasing to 90%, then returning to 0% to complete the cycle 1; rising again to 90% and decreasing back to 0% to conclude, completing the cycle 2 (as shown in FIGS. 35-36).

The DVS data results are as follows:

| | Crystal Form A of Hydrochloride Salt 0.42% Water Sorption at 90% Relative Humidity | | | | Crystal Form A of Phosphate Salt 0.80% Water Sorption at 90% Relative Humidity | | | |
|---|---|---|---|---|---|---|---|---|
| | Sorption (%) | Desorption (%) | Sorption (%) | Desorption (%) | Sorption (%) | Desorption (%) | Sorption (%) | Desorption (%) |
| 0% | 0.00 | −0.06 | −0.06 | −0.05 | 0.00 | −0.04 | −0.04 | −0.05 |
| 10% | −0.02 | −0.02 | −0.03 | −0.02 | 0.02 | −0.01 | −0.02 | −0.03 |
| 20% | 0.00 | 0.01 | 0.01 | 0.01 | 0.04 | 0.01 | 0.01 | 0.00 |
| 30% | 0.03 | 0.04 | 0.03 | 0.05 | 0.06 | 0.04 | 0.04 | 0.03 |
| 40% | 0.06 | 0.07 | 0.07 | 0.08 | 0.10 | 0.09 | 0.07 | 0.07 |
| 50% | 0.09 | 0.11 | 0.10 | 0.12 | 0.14 | 0.15 | 0.12 | 0.13 |
| 60% | 0.13 | 0.16 | 0.14 | 0.17 | 0.20 | 0.21 | 0.18 | 0.20 |
| 70% | 0.17 | 0.21 | 0.19 | 0.22 | 0.29 | 0.31 | 0.27 | 0.29 |
| 80% | 0.28 | 0.30 | 0.30 | 0.32 | 0.44 | 0.46 | 0.43 | 0.45 |
| 90% | 0.42 | 0.42 | 0.45 | 0.45 | 0.80 | 0.80 | 0.79 | 0.79 |

The test results show that both crystal form A of hydrochloride salt and crystal form A of phosphate salt have low hygroscopicity, and no changes are observed in the samples before and after the DVS test.

Example 17 Pharmacokinetic Test 10.1 Vehicle Information and Preparation of Administration Preparation for Test Sample Vehicle Information:

| Name | Grade | Batch Number | Source |
|---|---|---|---|
| DMSO | NA | SHBP7906 | Sigma-Aldrich |
| Tween 80 | AR | 20190220 | Sinopharm Chemical Reagent Co., Ltd. |
| Polyethylene Glycol 15-Hydroxystearate (Kolliphor HS15) | NA | NA | Provided by Hangzhou Polymed Biopharmaceuticals, Inc. |
| Saline | NA | 21030501 | Zhejiang Kancheer Pharmaceutical Co., Ltd. |

5% DMSO + 10% Tween 80 + 5% Kolliphor HS 15 + 80% Saline, where % represents volume ratio.

For hydrochloride salt: The preparation process of the 4 mg/mL administration preparation (5% DMSO+10% Tween 80+5% Kolliphor HS15+85% Saline) was as follows: Accurately 41.97 mg of hydrochloride salt was weighed into a 15 mL centrifuge tube, followed by the addition of 488 μL of DMSO and vortexing for 30 seconds to ensure complete dissolution of the compound. Subsequently, 976 μL of Tween 80 was added and vortexed for 30 seconds, followed by the addition of 488 μL of Kolliphor HS15 (Kolliphor HS15 was used after heating and melting at 50° C.) and vortexed for 30 seconds. Finally, 7808 L of saline was added and vortexed for 30 seconds, followed by ultrasonication for 10 seconds to remove bubbles. The resulting administration preparation was a suspension.

For free base: The preparation process of the 4 mg/mL administration preparation (5% DMSO+10% Tween 80+5% Kolliphor HS15+85% Saline) was as follows: Accurately 41.35 mg of the five-membered-fused six-membered compound of formula I (prepared in Example 1) was weighed into a 15 mL centrifuge tube, followed by the addition of 517 μL of DMSO and vortexing for 30 seconds to ensure complete dissolution of the compound. Subsequently, 1034 μL of Tween 80 was added and vortexed for 30 seconds, followed by the addition of 517 μL of Kolliphor HS15 (Kolliphor HS15 was used after heating and melting at 50° C.) and vortexed for 30 seconds. Finally, 8270 μL of saline was added and vortexed for 30 seconds, followed by ultrasonication for 10 seconds to remove bubbles. The resulting administration preparation was a suspension.

10.2 Experimental System 10.2.1 Experimental Animals

Species and Strain: Sprague-Dawley rats (SD rats) (Zhejiang Vital River Laboratory Animal Technology Co., Ltd.)

Animal Grade: SPF level

Planned initial body weight for administration: Male 200-250 g. Actual animal weights will be listed in the raw records.

Number and Gender of Animals: 3 (3 per group), male 10.2.2 Housing

The animals were housed in a barrier environment animal room and were given free access to food and water. Environmental conditions were maintained at room temperature 20° C.-26° C., relative humidity 40%-70%, with a 12-hour light/dark cycle. The animals were housed in polycarbonate plastic boxes with the dimensions of length×width×height=466 mm×314 mm×200 mm, and no more than 5 animals were housed in each cage.

10.2.3 Drinking Water

Animals were provided with free access to water.

10.2.4 Marking

Individual animal marking: The rats were marked with serial numbers written on their tails using a mark pen, with each animal having a unique marking, and each group being housed in one cage.

10.3 Experimental Design 10.3.1 Animal Grouping and Administration Dosage

Based on measured body weights, animals with similar weights were divided into groups of 3 animals each. The grouping and administration dosage are as shown in the table below. Blank group animals were used for the collection of blank biological matrices.

| | Group | Administration Dosage (mg/kg) | Administration Volume (mL/kg) | Administration Concentration (mg/mL) | Animal Number Male |
|---|---|---|---|---|---|
| 1 | Hydrochloride Salt or Free Base | 40 | 10 | 4 | HPB-M20221013-07 to HPB-M20221013-09 |

10.3.2 Administration

Administration route: Oral gavage

Administration volume: 10 mL/kg

Administration frequency: Single dose

Administration method: The test sample was administered orally via gavage using an appropriate syringe and gavage tube. When using a 2 mL or 5 mL syringe, the administration volume was recorded to one decimal place. When the minimum graduation value of the syringe was 0.2 mL and the administration volume was between two graduation marks, the higher volume was selected for administration.

Reason for choosing administration dosage: conventional dosage in pharmacokinetic studies.

10.3.3 Sample Collection and Processing

Sample collection: Approximately 0.30 mL of whole blood was collected from the orbital vein of Group 1 animals at each time point.

The experimental animals were fasted for 12 hours before administration, with free access to water. Blood samples were collected from Group 1 animals (oral gavage group) at 5 min, 15 min, 30 min, 1 h, 2 h, 4 h, 6 h, 8 h, and 24 h after administration.

Sample processing: The collected venous blood was immediately transferred to EDTA-$Na_2$-coated EP tubes (stored in a refrigerator or in an ice box with crushed ice at 2-8° C. prior to use), inverted at least 5 times for thorough mixing, and temporarily stored in an ice box with crushed ice. The collected whole blood was centrifuged at 2000 g for 10 min under 2-8° C. conditions within 2 h to separate plasma, which was then placed in newly labeled centrifuge tubes and stored at −20° C.

Sample labeling: The collected whole blood/plasma samples were labeled as R-HPB-M20221013-07-09-WB/P-Po-5 min/15 min/30 min/1 h/2 h/4 h/6 h/8 h/24 h; where "R" represents rat, "HPB" represents the project number; "M20221013" represents animal gender (male) and experimental date; "07-09" represents abbreviated animal numbers; "WB" represents whole blood; and "P" represents plasma.

10.4 Data Collection and Statistical Analysis

The pharmacokinetics group of the Department of Pharmacology and Toxicology conducted the analysis and measurement of all samples, followed by data summarization. Plasma concentration data were analyzed using the pharmacokinetic data analysis software WinNonlin. Non-compartmental analysis (NCA) was employed to calculate pharmacokinetic parameters such as $t_{1/2}$, $C_{max}$, $T_{max}$, $V_d$, CL, $AUC_{0-24}$, and F. The detailed results are shown in the following table:

| Test Sample (PO, 40 mpk) | Cmax (ng/mL) | $AUC_{0-24}$ (hr*ng/mL) |
|---|---|---|
| Free Base | 934.37 | 4879.95 |
| Hydrochloride Salt | 5117.67 | 27508.69 |

Conclusion: Compared with the free base, the hydrochloride salt can significantly increase the plasma concentration and exposure of the compound in rats.

Although specific embodiments of the present disclosure have been described above, it should be understood by those skilled in the art that these are merely illustrative examples, and various changes or modifications may be made to these embodiments without departing from the principles and essence of the present disclosure. Therefore, the scope of protection of the present disclosure shall be defined by the appended claims.

What is claimed is:

1. A crystal form of a five-membered-fused six-membered compound represented by formula I, and the crystal form is crystal form A, crystal form B, crystal form C, crystal form D, crystal form E, crystal form F, or crystal form G, wherein the crystal form A satisfies condition 1 or condition 2:

condition 1: the crystal form A has an X-ray powder diffraction pattern expressed by 2θ angles comprising characteristic peaks at 7.84±0.20°, 10.25±0.20°, 20.96±0.20°, 22.36±0.20°, and 25.85±0.20°;

condition 2: the crystal form A has an X-ray powder diffraction pattern expressed by 2θ angles comprising characteristic peaks at 13.12±0.20°, 19.05±0.20°, 25.85±0.20°, and 26.73±0.20°;

the crystal form C satisfies condition 1 or condition 2:

condition 1: the crystal form C has an X-ray powder diffraction pattern expressed by 2θ angles comprising characteristic peaks at 7.02±0.20°, 9.78±0.20°, 11.05±0.20°, 14.21±0.20°, 18.83±0.20°, and 20.44±0.20°;

condition 2: the crystal form C has an X-ray powder diffraction pattern expressed by 2θ angles comprising characteristic peaks at 11.05±0.20°, 14.21±0.20°, 18.83±0.20°, and 28.80±0.20°;

the crystal form B has an X-ray powder diffraction pattern expressed by 2θ angles comprising characteristic peaks at 9.94±0.20°, 11.81±0.20°, 16.26±0.20°, and 18.47±0.20°;

the crystal form D has an X-ray powder diffraction pattern expressed by 2θ angles comprising characteristic peaks at 9.51±0.20°, 15.35±0.20°, 19.27±0.20°, and 24.20±0.20°;

the crystal form E has an X-ray powder diffraction pattern expressed by 2θ angles comprising characteristic peaks at 9.21±0.20°, 10.61±0.20°, 13.93±0.20°, 18.66±0.20°, and 23.43±0.20°;

the crystal form F has an X-ray powder diffraction pattern expressed by 2θ angles comprising characteristic peaks at 5.53±0.20°, 5.93±0.20°, 10.38±0.20°, and 22.37±0.20°;

the crystal form G satisfies condition 1 or condition 2:

condition 1: the crystal form G has an X-ray powder diffraction pattern expressed by 2θ angles comprising characteristic peaks at 9.74±0.20°, 13.56±0.20°, 16.39±0.20°, and 24.51±0.20°;

condition 2: the crystal form G has an X-ray powder diffraction pattern expressed by 2θ angles comprising characteristic peaks at 9.74±0.20°, 13.56±0.20°, 16.39±0.20°, and 24.51±0.20°;

I

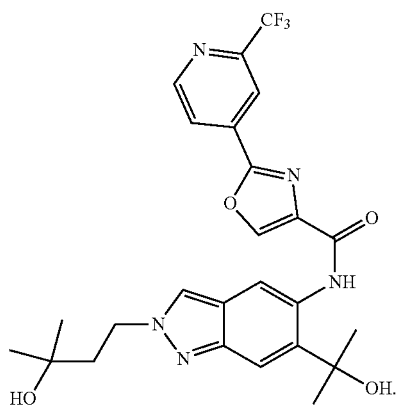

2. The crystal form according to claim 1, wherein:

In condition 1 of the crystal form A, the crystal form A has an X-ray powder diffraction pattern expressed by 2θ angles further comprising characteristic peaks at one or more of 11.33±0.20°, 13.12±0.20°, 14.43±0.20°, 15.52±0.20°, 16.78±0.20°, 17.55±0.20°, 20.77±0.20°, 22.92±0.20°, and 24.46±0.20°;

In condition 2 of the crystal form A, the crystal form A has an X-ray powder diffraction pattern expressed by 2θ angles further comprising characteristic peaks at one or more of 7.84±0.20°, 10.25±0.20°, 20.96±0.20°, and 24.46±0.20°;

In condition 1 of the crystal form C, the crystal form C has an X-ray powder diffraction pattern expressed by 2θ angles further comprising characteristic peaks at one or more of 11.59±0.20°, 18.19±0.20°, 21.17±0.20°, 22.87±0.20°, 23.98±0.20°, 24.19±0.20°, 25.71±0.20°, and 28.80±0.20°;

In condition 2 of the crystal form C, the crystal form C has an X-ray powder diffraction pattern expressed by 2θ angles further comprising characteristic peaks at one or more of 7.02±0.20°, 9.78±0.20°, 20.44±0.20°, and 23.98±0.20°;

the crystal form B has an X-ray powder diffraction pattern expressed by 2θ angles further comprising characteristic peaks at one or more of 11.41±0.20°, 14.41±0.20°, 20.73±0.20°, and 23.39±0.20°;

the crystal form D has an X-ray powder diffraction pattern expressed by 2θ angles further comprising characteristic peaks at one or more of 9.90±0.20°, 20.01±0.20°, 20.75±0.20°, and 29.18±0.20°;

the crystal form E has an X-ray powder diffraction pattern expressed by 2θ angles further comprising characteristic peaks at one or more of 20.06±0.20°, 21.85±0.20°, and 28.25±0.20°;

the crystal form F has an X-ray powder diffraction pattern expressed by 2θ angles further comprising characteristic peaks at one or more of 10.21±0.20°, 11.11±0.20°, 16.72±0.20°, and 25.78±0.20°;

in condition 1 of the crystal form G, the crystal form G has an X-ray powder diffraction pattern expressed by 2θ angles further comprising characteristic peaks at one or more of 7.09±0.20°, 14.28±0.20°, 15.61±0.20°, 18.5±0.20°, 20.36±0.20°, and 24.51±0.20°;

in condition 2 of the crystal form G, the crystal form G has an X-ray powder diffraction pattern expressed by 2θ angles further comprising characteristic peaks at one or more of 7.09±0.20°, 18.50±0.20°, 20.94±0.20°, and 23.36±0.20°.

3. The crystal form according to claim 1, wherein

In condition 2 of the crystal form A, the crystal form A has an X-ray powder diffraction pattern expressed by 2θ angles comprising characteristic peaks at 7.84±0.20°, 10.25±0.20°, 13.12±0.20°, 19.05±0.20°, 20.96±0.20°, 24.46±0.20°, 25.85±0.20°, and 26.73±0.20°;

In condition 2 of the crystal form C, the crystal form C has an X-ray powder diffraction pattern expressed by 2θ angles comprising characteristic peaks at 7.02±0.20°, 9.78±0.20°, 11.05±0.20°, 14.21±0.20°, 18.83±0.20°, 20.44±0.20°, 23.98±0.20°, and 28.80±0.20°;

In condition 2 of the crystal form G, the crystal form G has an X-ray powder diffraction pattern expressed by 2θ angles comprising characteristic peaks at 7.09±0.20°, 9.74±0.20°, 13.56±0.20°, 16.39±0.20°, 18.50±0.20°, 20.94±0.20°, 23.36±0.20°, and 24.51±0.20°;

the crystal form B has an X-ray powder diffraction pattern expressed by 2θ angles comprising characteristic peaks at 9.94±0.20°, 11.41±0.20°, 11.81±0.20°, 14.41±0.20°, 16.26±0.20°, 18.47±0.20°, 20.73±0.20°, and 23.39±0.20°;

the crystal form D has an X-ray powder diffraction pattern expressed by 2θ angles comprising characteristic peaks at 9.51±0.20°, 9.90±0.20°, 15.35±0.20°, 19.27±0.20°, 20.01±0.20°, 20.75±0.20°, 24.20±0.20°, and 29.18±0.20°;

the crystal form E has an X-ray powder diffraction pattern expressed by 2θ angles comprising characteristic peaks at 9.21±0.20°, 10.61±0.20°, 13.93±0.20°, 18.66±0.20°, 20.06±0.20°, 21.85±0.20°, 23.43±0.20°, and 28.25±0.20°;

the crystal form F has an X-ray powder diffraction pattern expressed by 2θ angles comprising characteristic peaks at 5.53±0.20°, 5.93±0.20°, 10.21±0.20°, 10.38±0.20°, 11.11±0.20°, 16.72±0.20°, 22.37±0.20°, and 25.78±0.20°.

4. The crystal form according to claim 1, wherein the crystal form A has an X-ray powder diffraction pattern expressed by 2θ angles comprising diffraction peaks at the diffraction angles shown in the following table:

| Number | 2θ Angle/° |
|---|---|
| 1 | 7.84 |
| 2 | 7.99 |
| 3 | 10.25 |
| 4 | 11.33 |
| 5 | 12.21 |
| 6 | 13.12 |
| 7 | 14.43 |
| 8 | 14.71 |
| 9 | 15.52 |

-continued

| Number | 2θ Angle/° |
|---|---|
| 10 | 15.67 |
| 11 | 16.18 |
| 12 | 16.36 |
| 13 | 16.57 |
| 14 | 16.78 |
| 15 | 17.19 |
| 16 | 17.55 |
| 17 | 17.90 |
| 18 | 18.25 |
| 19 | 18.70 |
| 20 | 19.05 |
| 21 | 20.21 |
| 22 | 20.44 |
| 23 | 20.77 |
| 24 | 20.96 |
| 25 | 21.32 |
| 26 | 21.66 |
| 27 | 22.36 |
| 28 | 22.60 |
| 29 | 22.92 |
| 30 | 23.15 |
| 31 | 23.44 |
| 32 | 24.01 |
| 33 | 24.46 |
| 34 | 24.71 |
| 35 | 25.45 |
| 36 | 25.85 |
| 37 | 26.08 |
| 38 | 26.73 |
| 39 | 26.92 |
| 40 | 27.08 |
| 41 | 27.47 |
| 42 | 28.33 |
| 43 | 29.29 |
| 44 | 29.46 |
| 45 | 29.64 |
| 46 | 31.45 |
| 47 | 31.64 |
| 48 | 32.28 |
| 49 | 32.54 |
| 50 | 33.31 |
| 51 | 33.64 |
| 52 | 33.96 |
| 53 | 36.97 |
| 54 | 37.35 |
| 55 | 37.58 |
| 56 | 37.73 |
| 57 | 38.31 |
| 58 | 38.70 |
| 59 | 39.05 |
| 60 | 39.27 |
| 61 | 39.77; |

the crystal form C has an X-ray powder diffraction pattern expressed by 2θ angles comprising diffraction peaks at the diffraction angles shown in the following table:

| Number | 2θ Angle/° |
|---|---|
| 1 | 7.02 |
| 2 | 9.78 |
| 3 | 10.19 |
| 4 | 11.05 |
| 5 | 11.31 |
| 6 | 11.59 |
| 7 | 12.53 |
| 8 | 13.85 |
| 9 | 14.21 |
| 10 | 14.41 |
| 11 | 15.20 |
| 12 | 15.37 |
| 13 | 15.75 |
| 14 | 16.17 |
| 15 | 16.60 |
| 16 | 17.97 |

-continued

| Number | 2θ Angle/° |
|---|---|
| 17 | 18.19 |
| 18 | 18.83 |
| 19 | 19.79 |
| 20 | 20.00 |
| 21 | 20.44 |
| 22 | 21.17 |
| 23 | 22.13 |
| 24 | 22.37 |
| 25 | 22.87 |
| 26 | 23.43 |
| 27 | 23.66 |
| 28 | 23.98 |
| 29 | 24.19 |
| 30 | 25.47 |
| 31 | 25.71 |
| 32 | 25.87 |
| 33 | 26.77 |
| 34 | 27.00 |
| 35 | 27.44 |
| 36 | 27.78 |
| 37 | 28.06 |
| 38 | 28.80 |
| 39 | 29.19 |
| 40 | 29.39 |
| 41 | 30.84 |
| 42 | 31.60 |
| 43 | 32.85 |
| 44 | 33.40 |
| 45 | 33.99 |
| 46 | 34.43 |
| 47 | 35.89 |
| 48 | 36.64 |
| 49 | 36.99 |
| 50 | 37.41 |
| 51 | 38.41 |
| 52 | 38.57; |

the crystal form B has an X-ray powder diffraction pattern expressed by 2θ angles comprising diffraction peaks at the diffraction angles shown in the following table:

| Number | 2θ Angle/° |
|---|---|
| 1 | 7.12 |
| 2 | 9.94 |
| 3 | 10.24 |
| 4 | 11.20 |
| 5 | 11.41 |
| 6 | 11.81 |
| 7 | 12.36 |
| 8 | 14.42 |
| 9 | 15.89 |
| 10 | 16.26 |
| 11 | 17.01 |
| 12 | 18.18 |
| 13 | 18.47 |
| 14 | 19.25 |
| 15 | 20.12 |
| 16 | 20.31 |
| 17 | 20.73 |
| 18 | 22.45 |
| 19 | 23.15 |
| 20 | 23.39 |
| 21 | 24.85 |
| 22 | 25.26 |
| 23 | 26.52 |
| 24 | 27.38 |
| 25 | 27.89 |
| 26 | 28.21 |
| 27 | 28.48 |
| 28 | 30.33 |
| 29 | 30.91 |
| 30 | 31.37 |
| 31 | 32.97 |
| 32 | 33.23 |

-continued

| Number | 2θ Angle/° |
|---|---|
| 33 | 34.44 |
| 34 | 34.74 |
| 35 | 35.08 |
| 36 | 37.79; |

the crystal form D has an X-ray powder diffraction pattern expressed by 2θ angles comprising diffraction peaks at the diffraction angles shown in the following table:

| Number | 2θ Angle/° |
|---|---|
| 1 | 7.73 |
| 2 | 9.51 |
| 3 | 9.90 |
| 4 | 10.16 |
| 5 | 10.87 |
| 6 | 11.18 |
| 7 | 12.86 |
| 8 | 13.34 |
| 9 | 14.40 |
| 10 | 15.35 |
| 11 | 15.86 |
| 12 | 16.79 |
| 13 | 19.27 |
| 14 | 20.01 |
| 15 | 20.57 |
| 16 | 20.75 |
| 17 | 22.36 |
| 18 | 23.34 |
| 19 | 24.20 |
| 20 | 24.78 |
| 21 | 25.20 |
| 22 | 25.88 |
| 23 | 26.49 |
| 24 | 27.32 |
| 25 | 29.18 |
| 26 | 29.69 |
| 27 | 30.87 |
| 28 | 33.29 |
| 29 | 34.20 |
| 30 | 34.65; |

the crystal form E has an X-ray powder diffraction pattern expressed by 2θ angles comprising diffraction peaks at the diffraction angles shown in the following table:

| Number | 2θ Angle/° |
|---|---|
| 1 | 9.23 |
| 2 | 9.77 |
| 3 | 10.61 |
| 4 | 12.71 |
| 5 | 13.15 |
| 6 | 13.94 |
| 7 | 14.51 |
| 8 | 14.88 |
| 9 | 15.75 |
| 10 | 17.09 |
| 11 | 18.15 |
| 12 | 18.67 |
| 13 | 19.43 |
| 14 | 20.06 |
| 15 | 20.90 |
| 16 | 21.85 |
| 17 | 23.42 |
| 18 | 27.97 |
| 19 | 28.25 |
| 20 | 33.50; |

the crystal form F has an X-ray powder diffraction pattern expressed by 2θ angles comprising diffraction peaks at the diffraction angles shown in the following table:

| Number | 2θ Angle/° |
|---|---|
| 1 | 5.53 |
| 2 | 5.93 |
| 3 | 6.12 |
| 4 | 7.95 |
| 5 | 9.85 |
| 6 | 10.21 |
| 7 | 10.38 |
| 8 | 10.55 |
| 9 | 11.11 |
| 10 | 11.47 |
| 11 | 12.35 |
| 12 | 13.25 |
| 13 | 14.55 |
| 14 | 14.87 |
| 15 | 15.86 |
| 16 | 16.72 |
| 17 | 16.91 |
| 18 | 17.70 |
| 19 | 17.94 |
| 20 | 19.83 |
| 21 | 21.15 |
| 22 | 21.83 |
| 23 | 22.37 |
| 24 | 23.06 |
| 25 | 23.37 |
| 26 | 24.14 |
| 27 | 24.59 |
| 28 | 24.84 |
| 29 | 25.78 |
| 30 | 25.98 |
| 31 | 26.22 |
| 32 | 26.88 |
| 33 | 27.43 |
| 34 | 28.09 |
| 35 | 31.42 |
| 36 | 33.85 |
| 37 | 34.09 |
| 38 | 35.57; |

the crystal form G has an X-ray powder diffraction pattern expressed by 2θ angles comprising diffraction peaks at the diffraction angles shown in the following table:

| Number | 2θ Angle/° |
|---|---|
| 1 | 4.86 |
| 2 | 7.09 |
| 3 | 9.74 |
| 4 | 10.35 |
| 5 | 11.07 |
| 6 | 11.45 |
| 7 | 13.56 |
| 8 | 14.28 |
| 9 | 15.42 |
| 10 | 15.61 |
| 11 | 15.87 |
| 12 | 16.39 |
| 13 | 18.07 |
| 14 | 18.50 |
| 15 | 19.27 |
| 16 | 19.66 |
| 17 | 19.94 |
| 18 | 20.13 |
| 19 | 20.36 |
| 20 | 20.94 |
| 21 | 21.52 |
| 22 | 22.49 |
| 23 | 23.22 |
| 24 | 23.36 |
| 25 | 24.13 |
| 26 | 24.51 |
| 27 | 26.89 |
| 28 | 27.52 |
| 29 | 28.25 |
| 30 | 28.91 |
| 31 | 29.38 |

-continued

| Number | 2θ Angle/° |
|---|---|
| 32 | 30.18 |
| 33 | 31.69 |
| 34 | 33.35 |
| 35 | 34.88 |
| 36 | 39.18. |

5. The crystal form according to claim 1, wherein the crystal form A satisfies one or more of the following conditions:

(1) diffraction peaks, d-spacing values, and relative intensities of the X-ray powder diffraction pattern of the crystal form A expressed by 2θ angles are shown in the following table:

| Number | 2θ Angle/° | d-Spacing/Å | Relative Intensity/% |
|---|---|---|---|
| 1 | 7.84 | 11.26 | 7.65 |
| 2 | 7.99 | 11.05 | 1.77 |
| 3 | 10.25 | 8.62 | 100 |
| 4 | 11.33 | 7.81 | 16.8 |
| 5 | 12.21 | 7.25 | 2.33 |
| 6 | 13.12 | 6.74 | 16.23 |
| 7 | 14.43 | 6.13 | 12.33 |
| 8 | 14.71 | 6.02 | 2.99 |
| 9 | 15.52 | 5.71 | 20.12 |
| 10 | 15.67 | 5.65 | 12.49 |
| 11 | 16.18 | 5.47 | 5.78 |
| 12 | 16.36 | 5.41) | 6.35 |
| 13 | 16.57 | 5.35 | 5.12 |
| 14 | 16.78 | 5.28 | 40.76 |
| 15 | 17.19 | 5.17 | 1.32 |
| 16 | 17.55 | 5.05 | 20.29 |
| 17 | 17.90 | 4.95 | 3.05 |
| 18 | 18.25 | 4.86 | 4.03 |
| 19 | 18.70 | 4.74 | 4.79 |
| 20 | 19.05 | 4.66 | 4.17 |
| 21 | 20.21 | 4.39 | 3 |
| 22 | 20.44 | 4.34 | 6.18 |
| 23 | 20.77 | 4.27 | 28.56 |
| 24 | 20.96 | 4.24 | 43.1 |
| 25 | 21.32 | 4.16 | 7.24 |
| 26 | 21.66 | 4.10 | 3.96 |
| 27 | 22.36 | 3.97 | 41.38 |
| 28 | 22.60 | 3.93 | 3.14 |
| 29 | 22.92 | 3.88 | 33.80 |
| 30 | 23.15 | 3.84 | 6.25 |
| 31 | 23.44 | 3.79 | 1.38 |
| 32 | 24.01 | 3.70 | 13.70 |
| 33 | 24.46 | 3.63 | 25.66 |
| 34 | 24.71 | 3.60 | 3.71 |
| 35 | 25.45 | 3.50 | 5.37 |
| 36 | 25.85 | 3.44 | 49.49 |
| 37 | 26.08 | 3.41 | 7.69 |
| 38 | 26.73 | 3.33 | 11.86 |
| 39 | 26.92 | 3.31 | 1.04 |
| 40 | 27.08 | 3.29 | 1.92 |
| 41 | 27.47 | 3.24 | 1.07 |
| 42 | 28.33 | 3.15 | 7.54 |
| 43 | 29.29 | 3.05 | 3.02 |
| 44 | 29.46 | 3.03 | 5.97 |
| 45 | 29.64 | 3.01 | 2.03 |
| 46 | 31.45 | 2.84 | 1.99 |
| 47 | 31.64 | 2.83 | 2.59 |
| 48 | 32.28 | 2.77 | 3.79 |
| 49 | 32.54 | 2.75 | 5.94 |
| 50 | 33.31 | 2.69 | 1.44 |
| 51 | 33.64 | 2.66 | 3.15 |
| 52 | 33.96 | 2.64 | 4.50 |
| 53 | 36.97 | 2.43 | 1.35 |
| 54 | 37.35 | 2.41 | 3.94 |
| 55 | 37.58 | 2.39 | 0.61 |
| 56 | 37.73 | 2.38 | 2.33 |
| 57 | 38.31 | 2.35 | 1.34 |

-continued

| Number | 2θ Angle/° | d-Spacing/Å | Relative Intensity/% |
|---|---|---|---|
| 58 | 38.70 | 2.33 | 0.4 |
| 59 | 39.05 | 2.30 | 4.73 |
| 60 | 39.27 | 2.29 | 1.37 |
| 61 | 39.77 | 2.26 | 0.20; |

(2) the crystal form A has a differential scanning calorimetry analysis pattern showing an onset of an endothermic peak at 231.31±2° C., and reaches a peak value of the endothermic peak at 232.04±2° C.; and has an enthalpy value of 111.300 J/g;

(3) the crystal form A has a differential scanning calorimetry analysis pattern showing an onset of an endothermic peak at 237.74±2° C., and reaches a peak value of the endothermic peak at 244.16±2° C.; and has an enthalpy value of 69.104 J/g;

(4) the crystal form A has a thermal gravimetric analysis pattern showing a weight loss of 0.428% at 200° C.; wherein "%" represents mass percentage;

the crystal form C satisfies one or more of the following conditions:

(1) diffraction peaks, d-spacing values, and relative intensities of the X-ray powder diffraction pattern of the crystal form C expressed by 2θ angles are shown in the following table:

| Number | 2θ Angle/° | d-Spacing/Å | Relative Intensity/% |
|---|---|---|---|
| 1 | 7.02 | 12.58 | 64.32 |
| 2 | 9.78 | 9.03 | 73.15 |
| 3 | 10.19 | 8.67 | 9.94 |
| 4 | 11.05 | 8.00 | 100.00 |
| 5 | 11.31 | 7.82 | 4.23 |
| 6 | 11.59 | 7.63 | 22.75 |
| 7 | 12.53 | 7.06 | 2.07 |
| 8 | 13.85 | 6.39 | 2.37 |
| 9 | 14.21 | 6.23 | 62.08 |
| 10 | 14.41 | 6.14 | 9.66 |
| 11 | 15.20 | 5.82 | 5.14 |
| 12 | 15.37 | 5.76 | 3.46 |
| 13 | 15.75 | 5.62 | 5.39 |
| 14 | 16.17 | 5.48 | 3.06 |
| 15 | 16.60 | 5.34 | 12.13 |
| 16 | 17.97 | 4.93 | 16.96 |
| 17 | 18.19 | 4.87 | 44.30 |
| 18 | 18.83 | 4.71 | 96.60 |
| 19 | 19.79 | 4.48 | 3.93 |
| 20 | 20.00 | 4.44 | 16.90 |
| 21 | 20.44 | 4.34 | 78.81 |
| 22 | 21.17 | 4.19 | 20.65 |
| 23 | 22.13 | 4.01 | 8.72 |
| 24 | 22.37 | 3.97 | 12.57 |
| 25 | 22.87 | 3.88 | 20.69 |
| 26 | 23.43 | 3.79 | 3.29 |
| 27 | 23.66 | 3.76 | 8.82 |
| 28 | 23.98 | 3.71 | 34.12 |
| 29 | 24.19 | 3.68 | 23.56 |
| 30 | 25.47 | 3.49 | 13.34 |
| 31 | 25.71 | 3.46 | 41.53 |
| 32 | 25.87 | 3.44 | 5.23 |
| 33 | 26.77 | 3.33 | 9.59 |
| 34 | 27.00 | 3.30 | 15.36 |
| 35 | 27.44 | 3.25 | 2.73 |
| 36 | 27.78 | 3.21 | 2.25 |
| 37 | 28.06 | 3.18 | 12.60 |
| 38 | 28.80 | 3.10 | 33.97 |
| 39 | 29.19 | 3.06 | 3.30 |
| 40 | 29.39 | 3.04 | 2.64 |
| 41 | 30.84 | 2.90 | 2.14 |

-continued

| Number | 2θ Angle/° | d-Spacing/Å | Relative Intensity/% |
|---|---|---|---|
| 42 | 31.60 | 2.83 | 1.63 |
| 43 | 32.85 | 2.73 | 9.80 |
| 44 | 33.40 | 2.68 | 1.73 |
| 45 | 33.99 | 2.64 | 2.62 |
| 46 | 34.43 | 2.60 | 2.87 |
| 47 | 35.89 | 2.50 | 1.58 |
| 48 | 36.64 | 2.45 | 11.29 |
| 49 | 36.99 | 2.43 | 7.51 |
| 50 | 37.41 | 2.40 | 1.77 |
| 51 | 38.41 | 2.34 | 10.89 |
| 52 | 38.57 | 2.33 | 10.28; |

(2) the crystal form C has a differential scanning calorimetry analysis pattern showing an onset of an endothermic peak at 63.692° C., and reaches a peak value of the endothermic peak at 82.10±2° C.; and has an enthalpy value of 61.396 J/g;

(3) the crystal form C has a differential scanning calorimetry analysis pattern showing an onset of an endothermic peak at 126.27±2° C., and reaches a peak value of the endothermic peak at 134.20±2° C.; and has an enthalpy value of 442.089 J/g;

(4) the crystal form C has a differential scanning calorimetry analysis pattern showing an onset of an endothermic peak at 230.61±2° C., and reaches a peak value of the endothermic peak at 231.73±2° C.; and has an enthalpy value of 103.46 J/g;

(5) the crystal form C has a thermal gravimetric analysis pattern showing a weight loss of 3.778% at 73.91° C.; the "%" represents mass percentage;

the crystal form B satisfies one or more of the following conditions:

(1) diffraction peaks, d-spacing values, and relative intensities of the X-ray powder diffraction pattern of the crystal form B expressed by 2θ angles are shown in the following table:

| Number | 2θ Angle/° | d-Spacing/Å | Relative Intensity/% |
|---|---|---|---|
| 1 | 7.12 | 12.40 | 16.52 |
| 2 | 9.94 | 8.89 | 74.06 |
| 3 | 10.24 | 8.63 | 10.16 |
| 4 | 11.20 | 7.89 | 31.34 |
| 5 | 11.41 | 7.75 | 42.69 |
| 6 | 11.81 | 7.49 | 12.75 |
| 7 | 12.36 | 7.16 | 2.61 |
| 8 | 14.42 | 6.14 | 55.24 |
| 9 | 15.89 | 5.57 | 36.43 |
| 10 | 16.26 | 5.45 | 25.97 |
| 11 | 17.01 | 5.21 | 4.16 |
| 12 | 18.18 | 4.88 | 14.48 |
| 13 | 18.47 | 4.80 | 27.34 |
| 14 | 19.25 | 4.61 | 28.04 |
| 15 | 20.12 | 4.41 | 12.85 |
| 16 | 20.31 | 4.37 | 15.69 |
| 17 | 20.73 | 4.28 | 100.00 |
| 18 | 22.45 | 3.96 | 6.45 |
| 19 | 23.15 | 3.84 | 13.45 |
| 20 | 23.39 | 3.80 | 85.19 |
| 21 | 24.85 | 3.58 | 10.82 |
| 22 | 25.26 | 3.52 | 14.37 |
| 23 | 26.52 | 3.36 | 5.76 |
| 24 | 27.38 | 3.26 | 17.04 |
| 25 | 27.89 | 3.20 | 17.16 |
| 26 | 28.21 | 3.16 | 22.03 |
| 27 | 28.48 | 3.13 | 6.27 |
| 28 | 30.33 | 2.94 | 8.00 |

-continued

| Number | 2θ Angle/° | d-Spacing/Å | Relative Intensity/% |
|---|---|---|---|
| 29 | 30.91 | 2.89 | 1.94 |
| 30 | 31.37 | 2.85 | 6.16 |
| 31 | 32.97 | 2.71 | 5.78 |
| 32 | 33.23 | 2.69 | 11.97 |
| 33 | 34.44 | 2.60 | 5.97 |
| 34 | 34.74 | 2.58 | 1.19 |
| 35 | 35.08 | 2.56 | 6.45 |
| 36 | 37.79 | 2.38 | 6.74; |

(2) the crystal form B has a differential scanning calorimetry analysis pattern showing an onset of an endothermic peak at 60.85±2° C., and reaches a peak value of the endothermic peak at 72.84±2° C.; and has an enthalpy value of 32.752 J/g;

(3) the crystal form B has a differential scanning calorimetry analysis pattern showing an onset of an endothermic peak at 151.04±2° C., and reaches a peak value of the endothermic peak at 153.19±2° C.; and has an enthalpy value of 4.135 J/g;

(4) the crystal form B has a differential scanning calorimetry analysis pattern showing an onset of an endothermic peak at 230.51±2° C., and reaches a peak value of the endothermic peak at 231.37±2° C.; and has an enthalpy value of 113.950 J/g;

(5) the crystal form B has a thermal gravimetric analysis pattern showing a weight loss of 4.741% at 122.68° C.; the "%" represents mass percentage;

the crystal form D satisfies one or more of the following conditions:

(1) diffraction peaks, d-spacing values, and relative intensities of the X-ray powder diffraction pattern of the crystal form D expressed by 2θ angles are shown in the following table:

| Number | 2θ Angle/° | d-Spacing/Å | Relative Intensity/% |
|---|---|---|---|
| 1 | 7.73 | 11.43 | 2.13 |
| 2 | 9.51 | 9.29 | 100.00 |
| 3 | 9.90 | 8.93 | 22.69 |
| 4 | 10.16 | 8.70 | 3.27 |
| 5 | 10.87 | 8.13 | 1.81 |
| 6 | 11.18 | 7.91 | 5.16 |
| 7 | 12.86 | 6.88 | 3.51 |
| 8 | 13.34 | 6.63 | 0.46 |
| 9 | 14.40 | 6.15 | 4.94 |
| 10 | 15.35 | 5.77 | 5.65 |
| 11 | 15.86 | 5.58 | 5.09 |
| 12 | 16.79 | 5.28 | 0.35 |
| 13 | 19.27 | 4.60 | 31.92 |
| 14 | 20.01 | 4.43 | 19.00 |
| 15 | 20.57 | 4.31 | 3.92 |
| 16 | 20.75 | 4.28 | 8.66 |
| 17 | 22.36 | 3.97 | 0.99 |
| 18 | 23.34 | 3.81 | 1.46 |
| 19 | 24.20 | 3.68 | 26.23 |
| 20 | 24.78 | 3.59 | 1.33 |
| 21 | 25.20 | 3.53 | 3.79 |
| 22 | 25.88 | 3.44 | 0.89 |
| 23 | 26.49 | 3.36 | 0.77 |
| 24 | 27.32 | 3.26 | 1.18 |
| 25 | 29.18 | 3.06 | 4.82 |
| 26 | 29.69 | 3.01 | 4.53 |
| 27 | 30.87 | 2.89 | 0.93 |
| 28 | 33.29 | 2.69 | 0.63 |
| 29 | 34.20 | 2.62 | 6.19 |
| 30 | 34.65 | 2.59 | 2.26; |

(2) the crystal form D has a differential scanning calorimetry analysis pattern showing an onset of an endothermic peak at 231.13±2° C., and reaches a peak value of the endothermic peak at 232.25±2° C.; and has an enthalpy value of 115.520 J/g;

(3) the crystal form D has a thermal gravimetric analysis pattern showing a weight loss of 2.826% at 116.38° C.; the "%" represents mass percentage;

the crystal form E satisfies one or more of the following conditions:

(1) diffraction peaks, d-spacing values, and relative intensities of the X-ray powder diffraction pattern of the crystal form E expressed by 2θ angles are shown in the following table:

| Number | 2θ Angle/° | d-Spacing/Å | Relative Intensity/% |
|---|---|---|---|
| 1 | 9.23 | 9.57 | 100.00 |
| 2 | 9.77 | 9.04 | 9.50 |
| 3 | 10.61 | 8.33 | 5.54 |
| 4 | 12.71 | 6.96 | 10.31 |
| 5 | 13.15 | 6.73 | 1.61 |
| 6 | 13.94 | 6.35 | 2.08 |
| 7 | 14.51 | 6.10 | 1.06 |
| 8 | 14.88 | 5.95 | 1.39 |
| 9 | 15.75 | 5.63 | 2.39 |
| 10 | 17.09 | 5.18 | 4.94 |
| 11 | 18.15 | 4.88 | 0.44 |
| 12 | 18.67 | 4.75 | 41.44 |
| 13 | 19.43 | 4.57 | 4.85 |
| 14 | 20.06 | 4.42 | 8.06 |
| 15 | 20.90 | 4.25 | 2.38 |
| 16 | 21.85 | 4.07 | 6.93 |
| 17 | 23.42 | 3.80 | 23.02 |
| 18 | 27.97 | 3.19 | 4.30 |
| 19 | 28.25 | 3.16 | 3.48 |
| 20 | 33.50 | 2.67 | 4.56; |

(2) the crystal form E has a differential scanning calorimetry analysis pattern showing an onset of an endothermic peak at 48.59±2° C., and reaches a peak value of the endothermic peak at 51.08±2° C.; and has an enthalpy value of 5.451 J/g;

(3) the crystal form E has a differential scanning calorimetry analysis pattern showing an onset of an endothermic peak at 90.07±2° C., and reaches a peak value of the endothermic peak at 95.66±2° C.; and has an enthalpy value of 19.797 J/g;

(4) the crystal form E has a differential scanning calorimetry analysis pattern showing an onset of an endothermic peak at 225.15±2° C., and reaches a peak value of the endothermic peak at 228.25±2° C.; and has an enthalpy value of 86.445 J/g;

(5) the crystal form E has a thermal gravimetric analysis pattern showing a weight loss of 5.5850% at 119.49° C.; the "%" represents mass percentage;

the crystal form F satisfies one or more of the following conditions:

(1) diffraction peaks, d-spacing values, and relative intensities of the X-ray powder diffraction pattern of the crystal form F expressed by 2θ angles are shown in the following table:

-continued

| Number | 2θ Angle/° | d-Spacing/Å | Relative Intensity/% |
|---|---|---|---|
| 1 | 5.53 | 15.96 | 26.20 |
| 2 | 5.93 | 14.89 | 13.26 |
| 3 | 6.12 | 14.43 | 34.33 |
| 4 | 7.95 | 11.11 | 33.35 |
| 5 | 9.85 | 8.97 | 2.34 |
| 6 | 10.21 | 8.66 | 28.81 |
| 7 | 10.38 | 8.52 | 82.19 |
| 8 | 10.55 | 8.38 | 13.78 |
| 9 | 11.11 | 7.96 | 96.68 |
| 10 | 11.47 | 7.71 | 7.48 |
| 11 | 12.35 | 7.16 | 18.98 |
| 12 | 13.25 | 6.68 | 2.69 |
| 13 | 14.55 | 6.08 | 2.97 |
| 14 | 14.87 | 5.96 | 6.52 |
| 15 | 15.86 | 5.59 | 44.50 |
| 16 | 16.72 | 5.30 | 33.17 |
| 17 | 16.91 | 5.24 | 23.83 |
| 18 | 17.70 | 5.01 | 4.35 |
| 19 | 17.94 | 4.94 | 3.33 |
| 20 | 19.83 | 4.47 | 4.64 |
| 21 | 21.15 | 4.20 | 43.26 |
| 22 | 21.83 | 4.07 | 37.17 |
| 23 | 22.37 | 3.97 | 100.00 |
| 24 | 23.06 | 3.85 | 7.85 |
| 25 | 23.37 | 3.80 | 29.30 |
| 26 | 24.14 | 3.68 | 3.89 |
| 27 | 24.59 | 3.62 | 8.33 |
| 28 | 24.84 | 3.58 | 10.99 |
| 29 | 25.78 | 3.45 | 23.92 |
| 30 | 25.98 | 3.43 | 13.74 |
| 31 | 26.22 | 3.40 | 3.24 |
| 32 | 26.88 | 3.31 | 9.38 |
| 33 | 27.43 | 3.25 | 15.36 |
| 34 | 28.09 | 3.17 | 13.63 |
| 35 | 31.42 | 2.85 | 20.13 |
| 36 | 33.85 | 2.65 | 15.91 |
| 37 | 34.09 | 2.63 | 2.69 |
| 38 | 35.57 | 2.52 | 4.70; |

(2) the crystal form F has a differential scanning calorimetry analysis pattern showing an onset of an endothermic peak at 49.64±2° C., and reaches a peak value of the endothermic peak at 52.43±2° C.; and has an enthalpy value of 3.400 J/g;

(3) the crystal form F has a differential scanning calorimetry analysis pattern showing an onset of an endothermic peak at 97.99±2° C., and reaches a peak value of the endothermic peak at 103.02±2° C.; and has an enthalpy value of 9.028 J/g;

(4) the crystal form F has a differential scanning calorimetry analysis pattern showing an onset of an endothermic peak at 225.07±2° C., and reaches a peak value of the endothermic peak at 226.71±2° C.; and has an enthalpy value of 92.201 J/g;

(5) the crystal form F has a thermal gravimetric analysis pattern showing a weight loss of 1.066% at 127.37° C.; the "%" represents mass percentage;

the crystal form G satisfies one or more of the following conditions:

(1) diffraction peaks, d-spacing values, and relative intensities of the X-ray powder diffraction pattern of the crystal form G expressed by 2θ angles are shown in the following table:

| Number | 2θ Angle/° | d-Spacing/Å | Relative Intensity/% |
|---|---|---|---|
| 1 | 4.86 | 18.17 | 1.49 |
| 2 | 7.09 | 12.46 | 19.43 |
| 3 | 9.74 | 9.07 | 100.00 |

-continued

| Number | 2θ Angle/° | d-Spacing/Å | Relative Intensity/% |
|---|---|---|---|
| 4 | 10.35 | 8.54 | 5.18 |
| 5 | 11.07 | 7.99 | 43.14 |
| 6 | 11.45 | 7.72 | 50.03 |
| 7 | 13.56 | 6.52 | 81.21 |
| 8 | 14.28 | 6.20 | 24.70 |
| 9 | 15.42 | 5.74 | 1.10 |
| 10 | 15.61 | 5.67 | 29.98 |
| 11 | 15.87 | 5.58 | 7.21 |
| 12 | 16.39 | 5.40 | 39.10 |
| 13 | 18.07 | 4.91 | 5.95 |
| 14 | 18.50 | 4.79 | 30.59 |
| 15 | 19.27 | 4.60 | 13.00 |
| 16 | 19.66 | 4.51 | 29.62 |
| 17 | 19.94 | 4.45 | 15.93 |
| 18 | 20.13 | 4.41 | 28.57 |
| 19 | 20.36 | 4.36 | 38.61 |
| 20 | 20.94 | 4.24 | 72.47 |
| 21 | 21.52 | 4.13 | 5.95 |
| 22 | 22.49 | 3.95 | 7.89 |
| 23 | 23.22 | 3.83 | 29.88 |
| 24 | 23.36 | 3.81 | 70.43 |
| 25 | 24.13 | 3.68 | 4.12 |
| 26 | 24.51 | 3.63 | 48.21 |
| 27 | 26.89 | 3.31 | 16.42 |
| 28 | 27.52 | 3.24 | 2.70 |
| 29 | 28.25 | 3.16 | 38.13 |
| 30 | 28.91 | 3.09 | 3.95 |
| 31 | 29.38 | 3.04 | 8.70 |
| 32 | 30.18 | 2.96 | 7.62 |
| 33 | 31.69 | 2.82 | 3.66 |
| 34 | 33.35 | 2.68 | 13.63 |
| 35 | 34.88 | 2.57 | 5.89 |
| 36 | 39.18 | 2.30 | 1.42; |

(2) the crystal form G has a differential scanning calorimetry analysis pattern showing an onset of an endothermic peak at 63.20±2° C., and reaches a peak value of the endothermic peak at 76.01±2° C.; and has an enthalpy value of 25.610 J/g;

(3) the crystal form G has a differential scanning calorimetry analysis pattern showing an onset of an endothermic peak at 150.82±2° C., and reaches a peak value of the endothermic peak at 153.33±2° C.; and has an enthalpy value of 12.882 J/g;

(4) the crystal form G has a differential scanning calorimetry analysis pattern showing an onset of an endothermic peak at 230.69±2° C., and reaches a peak value of the endothermic peak at 231.37±2° C.; and has an enthalpy value of 111.380 J/g;

(5) the crystal form G has a thermal gravimetric analysis pattern showing a weight loss of 3.405% at 130.90° C.; the "%" represents mass percentage.

Figure 2:
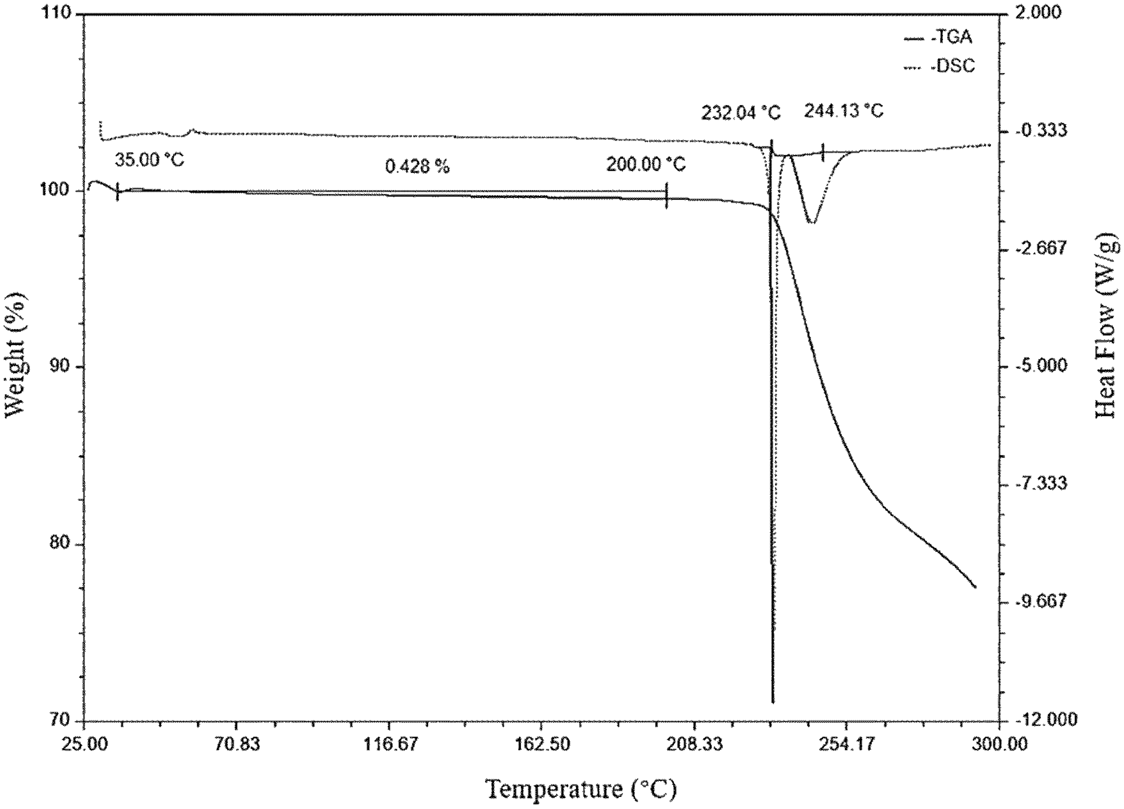
FIG. 2 shows the differential scanning calorimetry and thermal gravimetric analysis pattern of crystal form A.
Figure 3:
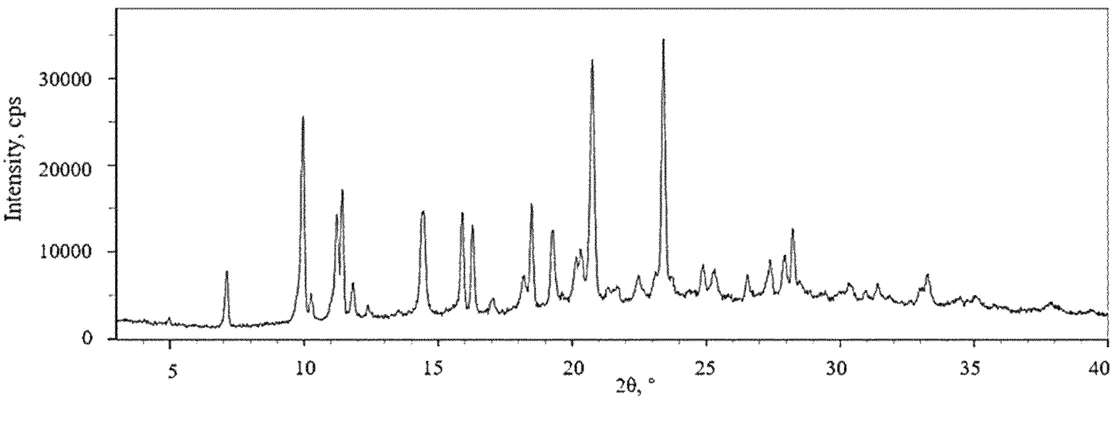
FIG. 3 shows the X-ray powder diffraction pattern of crystal form B.
Figure 4:
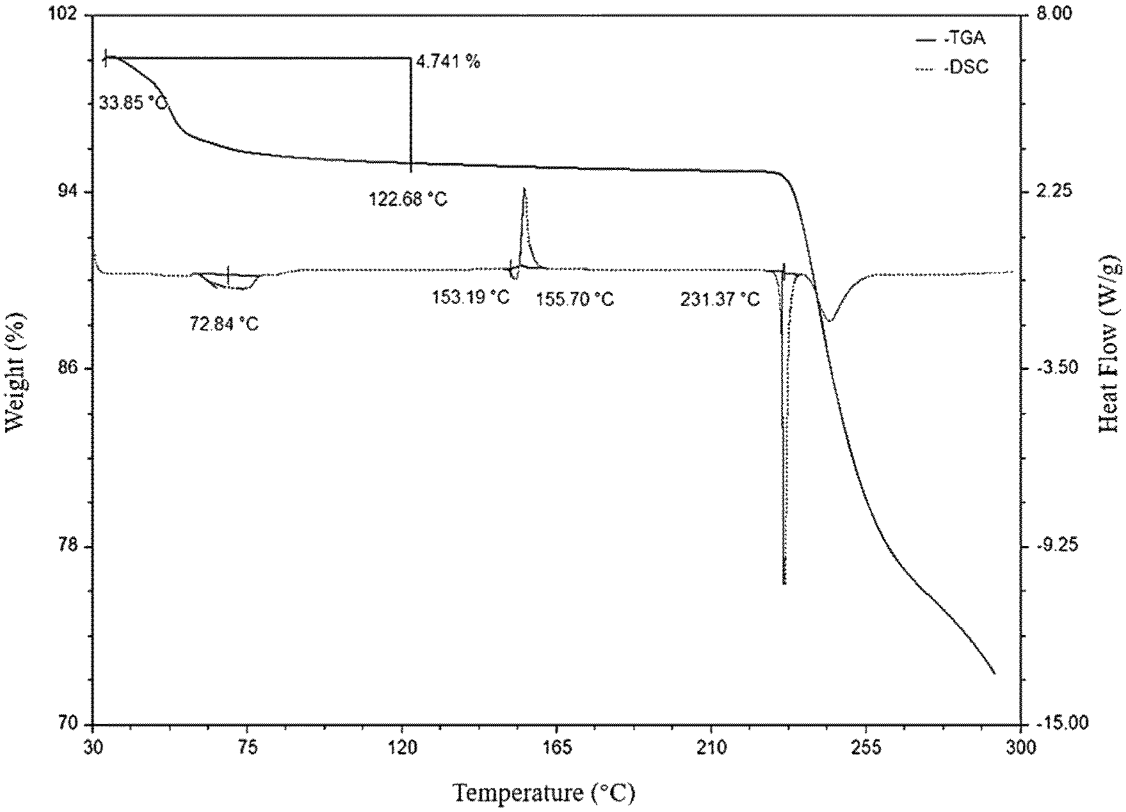
FIG. 4 shows the differential scanning calorimetry and thermal gravimetric analysis pattern of crystal form B.
Figure 5:
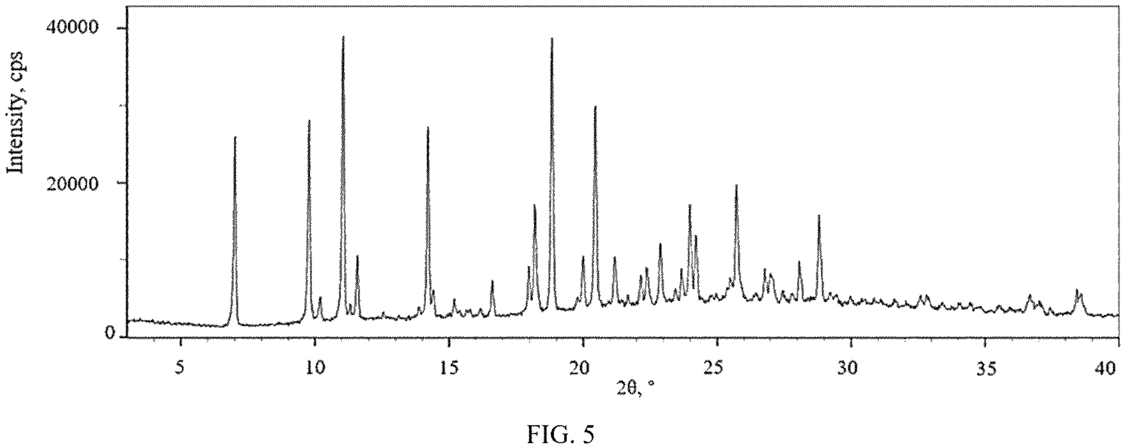
FIG. 5 shows the X-ray powder diffraction pattern of crystal form C.
Figure 6:
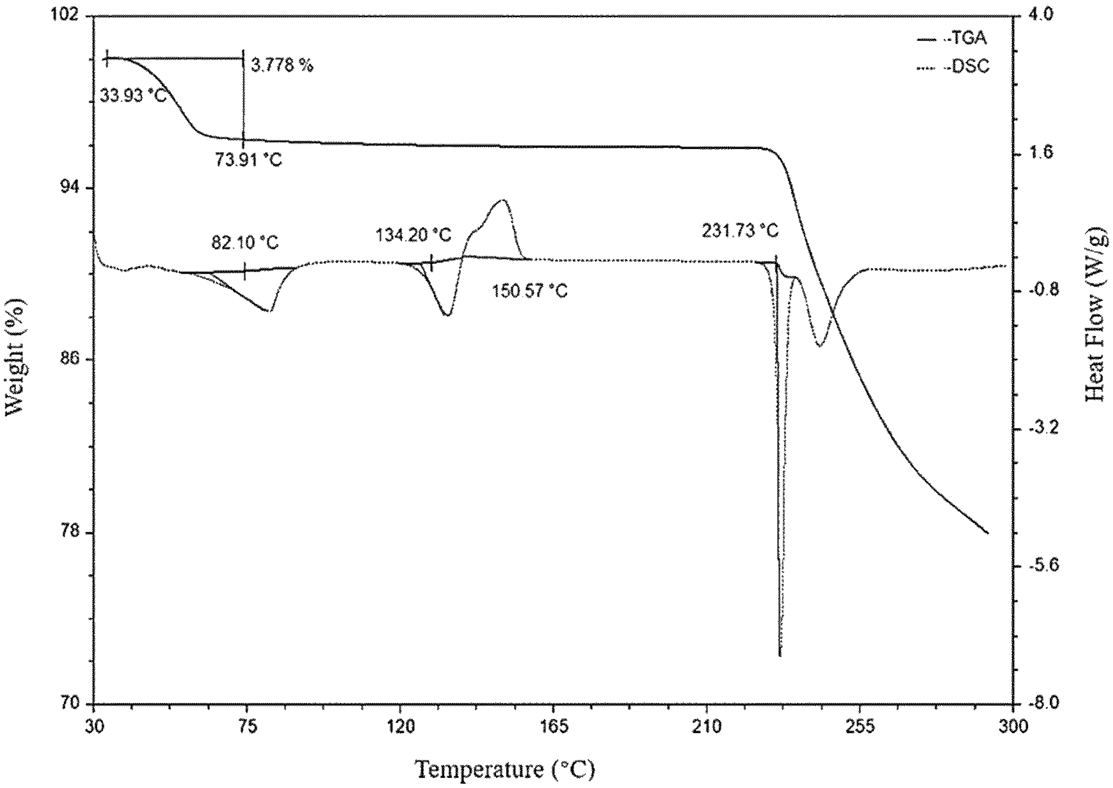
FIG. 6 shows the differential scanning calorimetry and thermal gravimetric analysis pattern of crystal form C.
Figure 7:
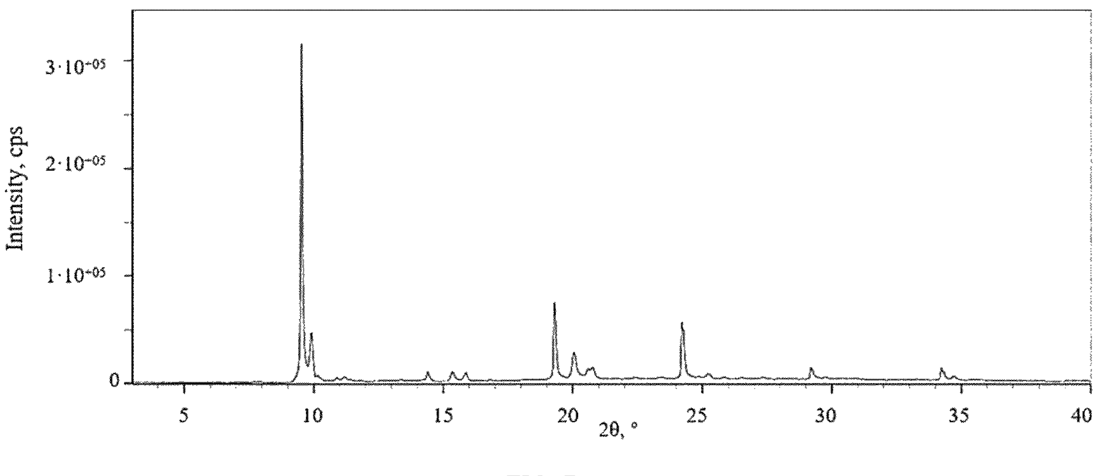
FIG. 7 shows the X-ray powder diffraction pattern of crystal form D.
Figure 8:
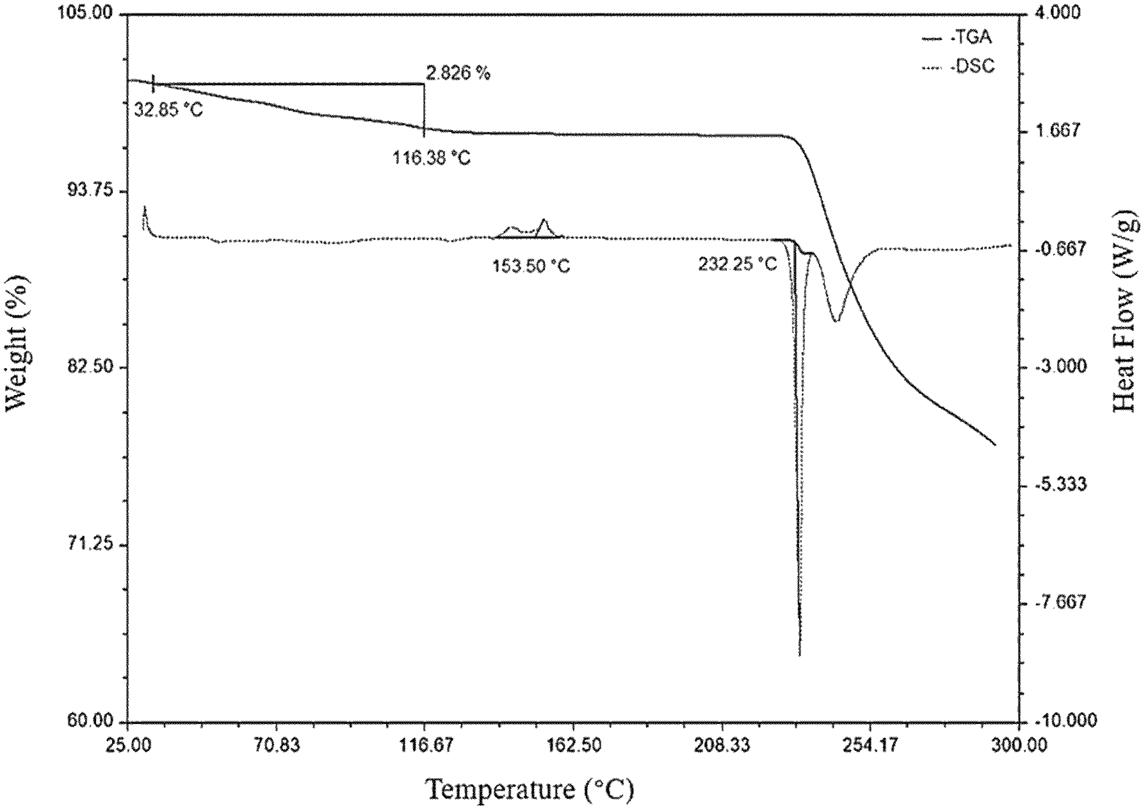
FIG. 8 shows the differential scanning calorimetry and thermal gravimetric analysis pattern of crystal form D.
Figure 9:
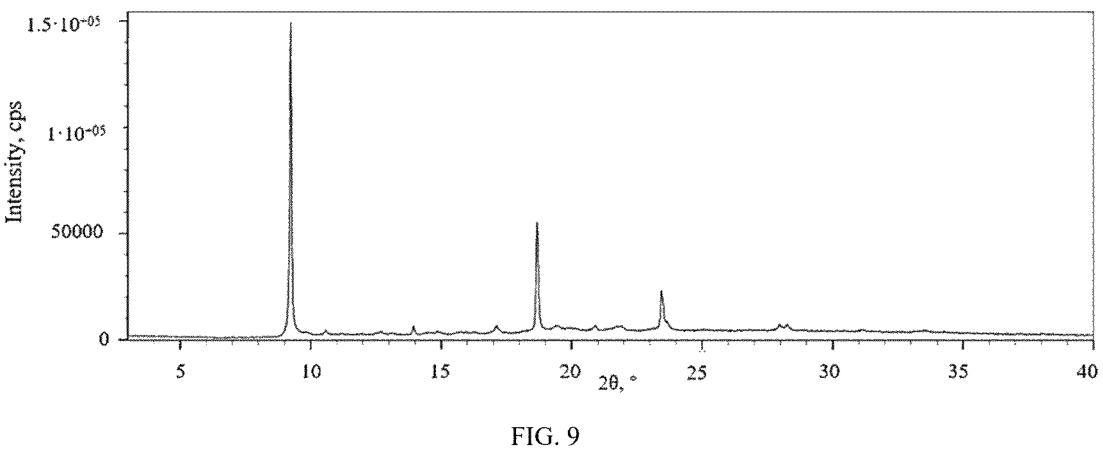
FIG. 9 shows the X-ray powder diffraction pattern of crystal form E.
Figure 10:
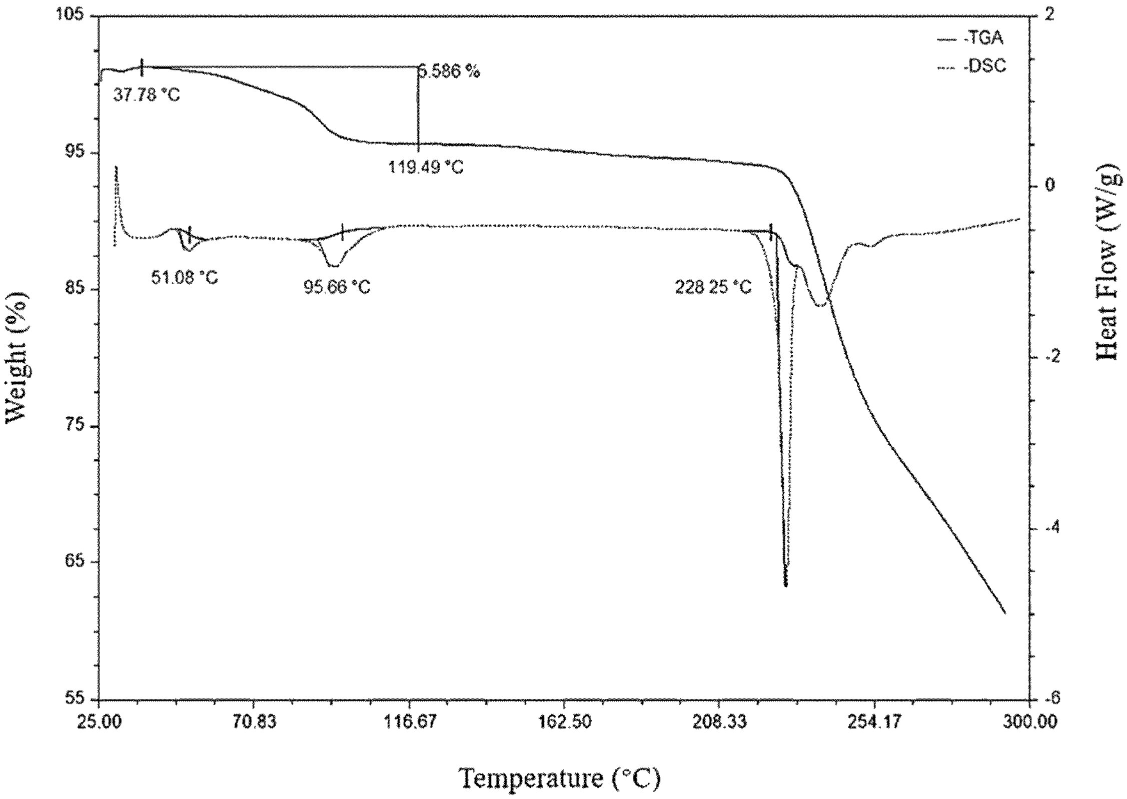
FIG. 10 shows the differential scanning calorimetry and thermal gravimetric analysis pattern of crystal form E.
Figure 11:
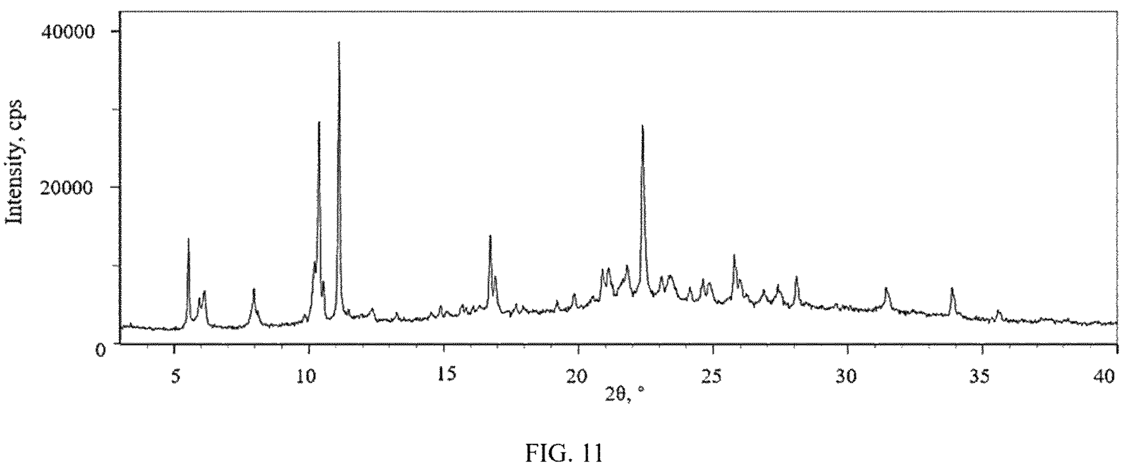
FIG. 11 shows the X-ray powder diffraction pattern of crystal form F.
Figure 12:
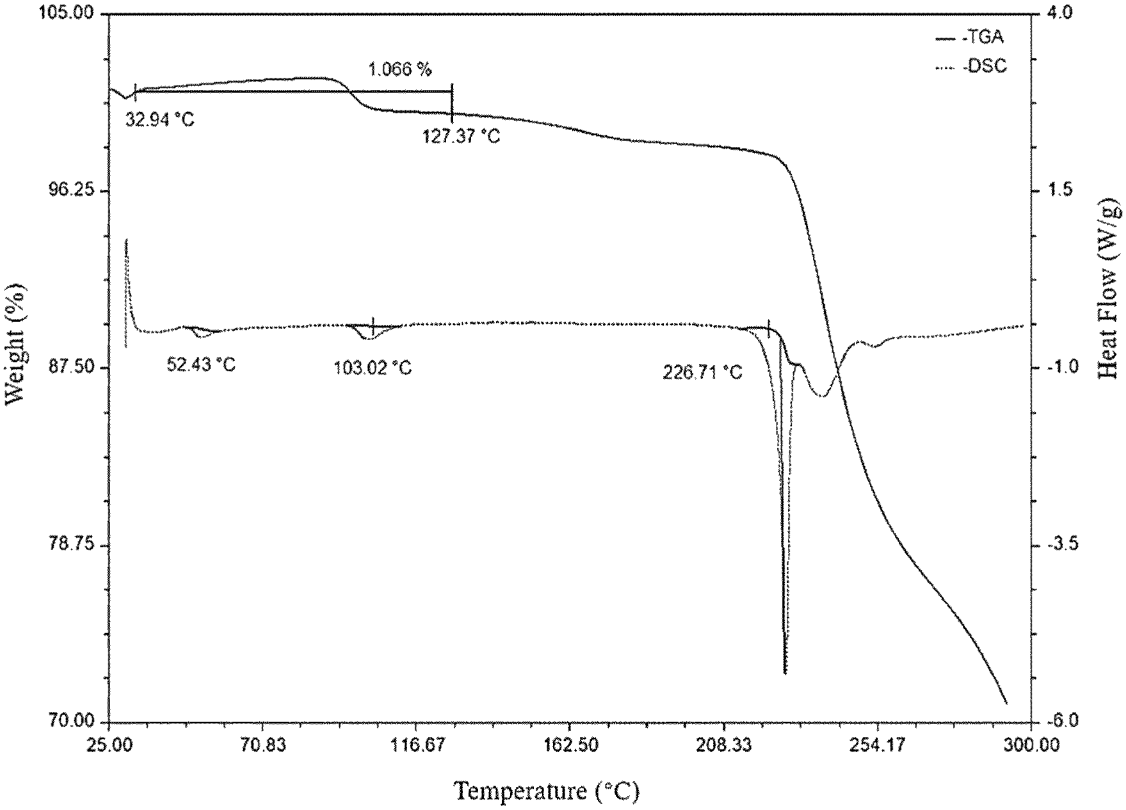
FIG. 12 shows the differential scanning calorimetry and thermal gravimetric analysis pattern of crystal form F.
Figure 13:
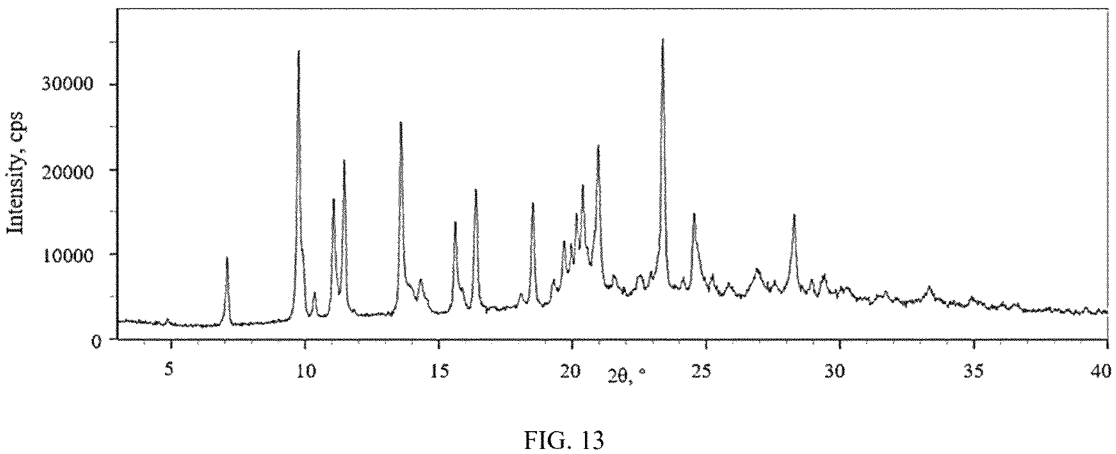
FIG. 13 shows the X-ray powder diffraction pattern of crystal form G.
Figure 14:
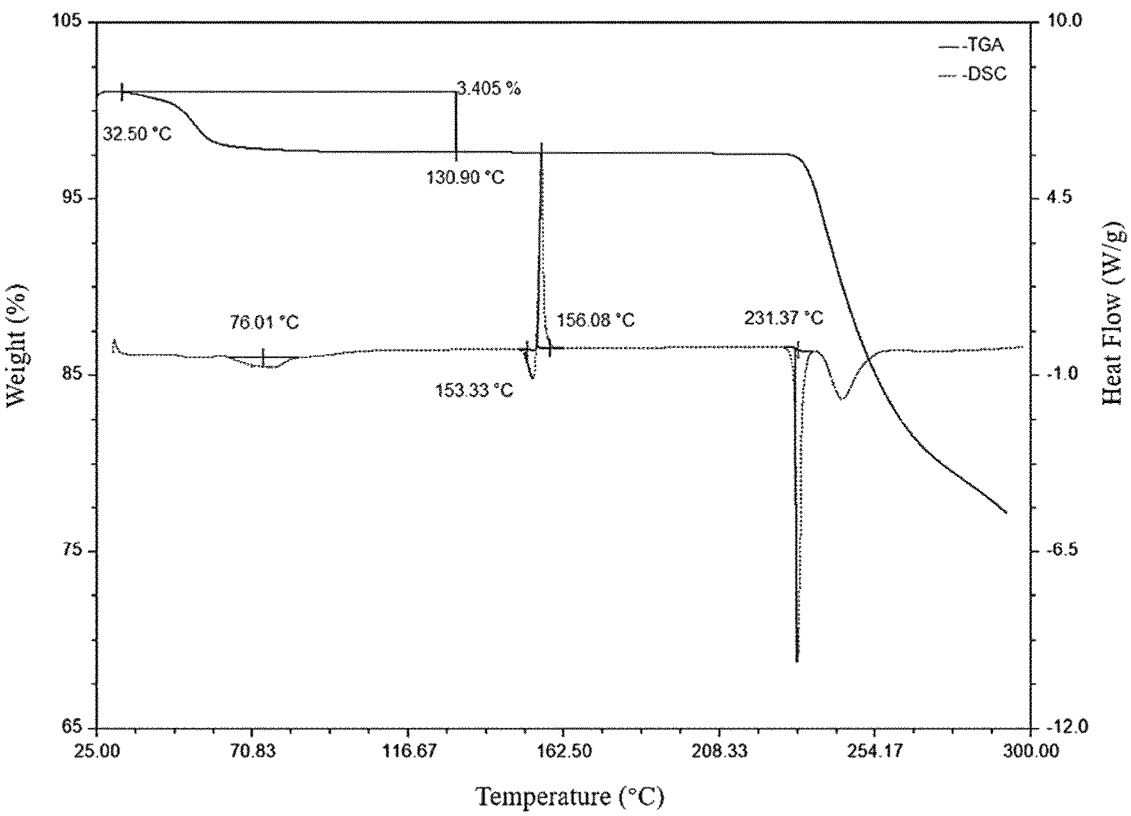
FIG. 14 shows the differential scanning calorimetry and thermal gravimetric analysis pattern of crystal form G.

6. The crystal form according to claim 1, wherein the crystal form A satisfies one or more of the following conditions:

(1) the X-ray powder diffraction pattern of the crystal form A is substantially as shown in FIG. 1;

(2) the differential scanning calorimetry analysis pattern of the crystal form A is substantially as shown in FIG. 2;

(3) the thermal gravimetric analysis pattern of the crystal form A is substantially as shown in FIG. 2;

the crystal form C satisfies one or more of the following conditions:

(1) the X-ray powder diffraction pattern of the crystal form C is substantially as shown in FIG. 5;

(2) the differential scanning calorimetry analysis pattern of the crystal form C is substantially as shown in FIG. 6;

(3) the thermal gravimetric analysis pattern of the crystal form C is substantially as shown in FIG. 6;

the crystal form B satisfies one or more of the following conditions:

(1) the X-ray powder diffraction pattern of the crystal form B is substantially as shown in FIG. 3;

(2) the differential scanning calorimetry analysis pattern of the crystal form B is substantially as shown in FIG. 4;

(3) the thermal gravimetric analysis pattern of the crystal form B is substantially as shown in FIG. 4;

the crystal form D satisfies one or more of the following conditions:

(1) the X-ray powder diffraction pattern of the crystal form D is substantially as shown in FIG. 7;

(2) the differential scanning calorimetry analysis pattern of the crystal form D is substantially as shown in FIG. 8;

(3) the thermal gravimetric analysis pattern of the crystal form D is substantially as shown in FIG. 8;

the crystal form E satisfies one or more of the following conditions:

(1) the X-ray powder diffraction pattern of the crystal form E is substantially as shown in FIG. 9;

(2) the differential scanning calorimetry analysis pattern of the crystal form E is substantially as shown in FIG. 10;

(3) the thermal gravimetric analysis pattern of the crystal form E is substantially as shown in FIG. 10;

the crystal form F satisfies one or more of the following conditions:

(1) the X-ray powder diffraction pattern of the crystal form F is substantially as shown in FIG. 11;

(2) the differential scanning calorimetry analysis pattern of the crystal form F is substantially as shown in FIG. 12;

(3) the thermal gravimetric analysis pattern of the crystal form F is substantially as shown in FIG. 12;

the crystal form G satisfies one or more of the following conditions:

(1) the X-ray powder diffraction pattern of the crystal form G is substantially as shown in FIG. 13;

(2) the differential scanning calorimetry analysis pattern of the crystal form G is substantially as shown in FIG. 14;

(3) and/or, the thermal gravimetric analysis pattern of the crystal form G is substantially as shown in FIG. 14.

7. A salt of a five-membered-fused six-membered compound represented by formula I, wherein the salt is a hydrochloride salt, a sulfate salt, a phosphate salt, a sodium salt, or a potassium salt;

I

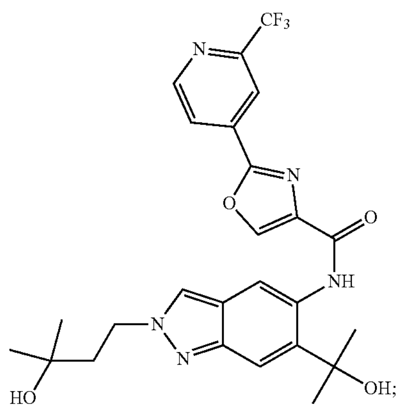

the salt satisfies the following conditions:

(1) the hydrochloride salt is a monohydrochloride salt;

(2) the sulfate salt is a monosulfate salt;

(3) the phosphate salt is a monophosphate salt;

(4) the sodium salt is a monosodium salt; and (5) the potassium salt is a monopotassium salt.

8. A crystal form of the salt of a five-membered-fused six-membered compound represented by formula I as defined in claim 7, and the crystal form is crystal form A of the hydrochloride salt, crystal form B of the hydrochloride salt, crystal form A of the sulfate salt, crystal form B of the sulfate salt, crystal form C of the sulfate salt, crystal form A of the phosphate salt, crystal form B of the phosphate salt, crystal form A of the sodium salt or crystal form A of the potassium salt, wherein:

the crystal form A of the hydrochloride salt has an X-ray powder diffraction pattern expressed by 2θ angles using Cu—Kα radiation and comprising characteristic peaks at 10.81±0.20°, 20.20±0.20°, 22.70±0.20°, 23.74±0.20°, 29.89±0.20°, and 39.32±0.20°;

the crystal form B of the hydrochloride salt has an X-ray powder diffraction pattern expressed by 2θ angles using Cu—Kα radiation and comprising characteristic peaks at 8.2±0.20°, 13.28±0.20°, 18.87±0.20°, 25.07±0.20°, 34.76±0.20°, and 35.21±0.20°;

the crystal form A of the sulfate salt has an X-ray powder diffraction pattern expressed by 2θ angles using Cu—Kα radiation and comprising characteristic peaks at 19.62±0.20°, 27.19±0.20°, 28.70±0.20°, 32.36±0.20°, 33.43±0.20°, and 34.15±0.20°;

the crystal form B of the sulfate salt has an X-ray powder diffraction pattern expressed by 2θ angles using Cu—Kα radiation and comprising characteristic peaks at 15.86±0.20°, 16.53±0.20°, 20.05±0.20°, 28.46±0.20°, and 30.59±0.20°;

the crystal form C of the sulfate salt has an X-ray powder diffraction pattern expressed by 2θ angles using Cu—Kα radiation and comprising characteristic peaks at 7.70±0.20°, 12.87±0.20°, 19.87±0.20°, 21.55±0.20°, and 25.94±0.20°;

the crystal form A of the phosphate salt has an X-ray powder diffraction pattern expressed by 2θ angles using Cu—Kα radiation and comprising characteristic peaks at 10.04±0.20°, 14.10±0.20°, 18.10±0.20°, 22.80±0.20°, 24.57±0.20°, 28.44±0.20°, and 30.82±0.20°;

the crystal form B of the phosphate salt has an X-ray powder diffraction pattern expressed by 2θ angles using Cu—Kα radiation and comprising characteristic peaks at 17.96±0.20°, 21.10±0.20°, 21.41±0.20°, 23.38±0.20°, 26.91±0.20°, and 28.9±0.20°;

the crystal form A of the sodium salt has an X-ray powder diffraction pattern expressed by 2θ angles using Cu—Kα radiation and comprising characteristic peaks at 7.04±0.20°, 11.05±0.20°, 11.55±0.20°, 15.18±0.20°, 17.98±0.20°, 22.09±0.20°, 25.65±0.20°, and 28.76±0.20°; and the crystal form A of the potassium salt has an X-ray powder diffraction pattern expressed by 2θ angles using Cu—Kα radiation and comprising characteristic peaks at 7.04±0.20°, 9.75±0.20°, 11.05±0.20°, 11.49±0.20°, 14.20±0.20°, 15.06±0.20°, 18.06±0.20°, 25.58±0.20°, and 30.93±0.20°.

9. The salt according to claim 8, wherein:

in the crystal form A of the hydrochloride salt, the X-ray powder diffraction pattern thereof expressed by 2θ angles further comprises characteristic peaks at one or more of 11.72±0.20°, 21.88±0.20°, 28.61±0.20°, and 31.26±0.20°;

in the crystal form B of the hydrochloride salt, the X-ray powder diffraction pattern thereof expressed by 2θ angles further comprises characteristic peaks at one or more of 13.93±0.20°, 15.28±0.20°, 27.18±0.20°, and 28.99±0.20°;

in the crystal form A of the sulfate salt, the X-ray powder diffraction pattern thereof expressed by 2θ angles further comprises characteristic peaks at one or more of 14.94±0.20°, 17.42±0.20°, 22.76±0.20°, and 26.46±0.20°;

in the crystal form B of the sulfate salt, the X-ray powder diffraction pattern thereof expressed by 2θ angles further comprises characteristic peaks at one or more of 9.00±0.20°, 12.52±0.20°, 21.21±0.20°, and 22.36±0.20°;

in the crystal form C of the sulfate salt, the X-ray powder diffraction pattern thereof expressed by 2θ angles further comprises characteristic peaks at one or more of 8.74±0.20°, 10.67±0.20°, 18.64±0.20°, and 19.05±0.20°;

in the crystal form A of the phosphate salt, the X-ray powder diffraction pattern thereof expressed by 2θ angles further comprises characteristic peaks at one or more of 6.57±0.20°, 18.53±0.20°, 19.97±0.20°, 22.43±0.20°, and 27.18±0.20°;

in the crystal form B of the phosphate salt, the X-ray powder diffraction pattern thereof expressed by 2θ angles further comprises characteristic peaks at one or more of 7.40±0.20°, 17.61±0.20°, 19.69±0.20°, and 24.93±0.20°;

in the crystal form A of the sodium salt, the X-ray powder diffraction pattern thereof expressed by 2θ angles further comprises characteristic peaks at one or more of 9.78±0.20°, 14.20±0.20°, 18.81±0.20°, 19.97±0.20°, and 24.13±0.20°;

in the crystal form A of the potassium salt, the X-ray powder diffraction pattern thereof expressed by 2θ angles further comprises characteristic peaks at one or more of 19.46±0.20°, 19.96±0.20°, 23.54±0.20°, and 27.92±0.20°.

10. The salt according to claim 8, wherein in the crystal form A of the hydrochloride salt, the X-ray powder diffraction pattern thereof expressed by 2θ angles comprises characteristic peaks at 10.81±0.20°, 11.72±0.20°, 20.20±0.20°, 21.88±0.20°, 22.70±0.20°, 23.74±0.20°, 28.61±0.20°, 29.89±0.20°, 31.26±0.20°, and 39.32±0.20°;

in the crystal form B of the hydrochloride salt, the X-ray powder diffraction pattern thereof expressed by 2θ angles comprises characteristic peaks at 8.2±0.20°, 13.28±0.20°, 13.93±0.20°, 15.28±0.20°, 18.87±0.20°, 25.07±0.20°, 27.18±0.20°, 28.99±0.20°, 34.76±0.20°, and 35.21±0.20°;

in the crystal form A of the sulfate salt, the X-ray powder diffraction pattern thereof expressed by 2θ angles comprises characteristic peaks at 14.94±0.20°, 17.42±0.20°, 19.62±0.20°, 22.76±0.20°, 26.46±0.20°, 27.19±0.20°, 28.70±0.20°, 32.36±0.20°, 33.43±0.20°, and 34.15±0.20°;

in the crystal form B of the sulfate salt, the X-ray powder diffraction pattern thereof expressed by 2θ angles comprises characteristic peaks at 9.00±0.20°, 12.52±0.20°, 15.86±0.20°, 16.53±0.20°, 20.05±0.20°, 21.21±0.20°, 22.36±0.20°, 28.46±0.20°, and 30.59±0.20°;

in the crystal form C of the sulfate salt, the X-ray powder diffraction pattern thereof expressed by 2θ angles comprises characteristic peaks at 7.70±0.20°, 8.74±0.20°, 10.67±0.20°, 12.87±0.20°, 18.64±0.20°, 19.05±0.20°, 19.87±0.20°, 21.55±0.20°, and 25.94±0.20°;

in the crystal form A of the phosphate salt, the X-ray powder diffraction pattern thereof expressed by 2θ angles comprises characteristic peaks at 6.57±0.20°, 10.04±0.20°, 14.10±0.20°, 18.10±0.20°, 18.53±0.20°, 19.97±0.20°, 22.43±0.20°, 22.80±0.20°, 24.57±0.20°, 27.18±0.20°, 28.44±0.20°, and 30.82±0.20°;

in the crystal form B of the phosphate salt, the X-ray powder diffraction pattern thereof expressed by 2θ angles comprises characteristic peaks at 7.40±0.20°, 17.61±0.20°, 17.96±0.20°, 19.69±0.20°, 21.10±0.20°, 21.41±0.20°, 23.38±0.20°, 24.93±0.20°, 26.91±0.20°, and 28.9±0.20°;

in the crystal form A of the sodium salt, the X-ray powder diffraction pattern thereof expressed by 2θ angles comprises characteristic peaks at 7.04±0.20°, 9.78±0.20°, 11.05±0.20°, 11.55±0.20°, 14.20±0.20°, 15.18±0.20°, 17.98±0.20°, 18.81±0.20°, 19.97±0.20°, 22.09±0.20°, 24.13±0.20°, 25.65±0.20°, and 28.76±0.20°;

in the crystal form A of the potassium salt, the X-ray powder diffraction pattern thereof expressed by 2θ angles comprises characteristic peaks at 7.04±0.20°, 9.75±0.20°, 11.05±0.20°, 11.49±0.20°, 14.20±0.20°, 15.06±0.20°, 18.06±0.20°, 19.46±0.20°, 19.96±0.20°, 23.54±0.20°, 25.58±0.20°, 27.92±0.20°, and 30.93±0.20°.

11. The salt according to claim 8 wherein:

in the crystal form A of the hydrochloride salt, diffraction peaks in the X-ray powder diffraction pattern of the crystal form A expressed by 2θ angles are shown in the following table:

| Number | 2θ Angle/° |
|---|---|
| 1 | 7.37 |
| 2 | 9.06 |
| 3 | 10.81 |
| 4 | 11.24 |
| 5 | 11.72 |
| 6 | 12.60 |
| 7 | 13.67 |
| 8 | 14.91 |
| 9 | 15.20 |
| 10 | 16.26 |
| 11 | 16.76 |
| 12 | 17.10 |
| 13 | 18.12 |
| 14 | 18.45 |
| 15 | 18.79 |
| 16 | 19.26 |
| 17 | 19.68 |
| 18 | 19.97 |
| 19 | 20.20 |
| 20 | 20.46 |
| 21 | 21.01 |
| 22 | 21.16 |
| 23 | 21.32 |
| 24 | 21.88 |
| 25 | 22.50 |
| 26 | 22.70 |
| 27 | 23.00 |
| 28 | 23.74 |
| 29 | 24.18 |
| 30 | 24.51 |
| 31 | 24.96 |
| 32 | 25.32 |
| 33 | 25.53 |
| 34 | 25.68 |
| 35 | 26.02 |
| 36 | 26.34 |
| 37 | 26.64 |
| 38 | 26.89 |
| 39 | 27.70 |
| 40 | 28.04 |
| 41 | 28.39 |
| 42 | 28.61 |
| 43 | 28.84 |
| 44 | 29.24 |
| 45 | 29.89 |
| 46 | 30.18 |
| 47 | 31.00 |
| 48 | 31.27 |
| 49 | 32.58 |
| 50 | 32.99 |
| 51 | 33.55 |
| 52 | 33.91 |
| 53 | 35.80 |
| 54 | 36.28 |
| 55 | 36.90 |
| 56 | 37.23 |
| 57 | 37.38 |
| 58 | 38.28 |
| 59 | 38.57 |
| 60 | 39.32 |
| 61 | 39.54; |

in the crystal form B of the hydrochloride salt, diffraction peaks in the X-ray powder diffraction pattern of the crystal form B expressed by 2θ angles are shown in the following table:

| Number | 2θ Angle/° |
|---|---|
| 1 | 7.37 |
| 2 | 7.70 |
| 3 | 8.20 |
| 4 | 13.02 |
| 5 | 13.28 |
| 6 | 13.93 |
| 7 | 14.78 |
| 8 | 14.89 |
| 9 | 15.28 |
| 10 | 15.58 |
| 11 | 16.85 |
| 12 | 18.07 |
| 13 | 18.18 |
| 14 | 18.54 |

-continued

| Number | 2θ Angle/° |
|---|---|
| 15 | 18.87 |
| 16 | 19.51 |
| 17 | 20.18 |
| 18 | 21.08 |
| 19 | 21.43 |
| 20 | 21.62 |
| 21 | 22.51 |
| 22 | 24.21 |
| 23 | 24.45 |
| 24 | 24.69 |
| 25 | 25.07 |
| 26 | 25.88 |
| 27 | 26.40 |
| 28 | 26.61 |
| 29 | 26.90 |
| 30 | 27.18 |
| 31 | 28.99 |
| 32 | 29.99 |
| 33 | 31.68 |
| 34 | 31.89 |
| 35 | 32.28 |
| 36 | 32.58 |
| 37 | 33.53 |
| 38 | 33.89 |
| 39 | 34.36 |
| 40 | 34.58 |
| 41 | 34.76 |
| 42 | 35.21 |
| 43 | 35.72 |
| 44 | 37.54 |
| 45 | 37.75 |
| 46 | 38.45 |
| 47 | 39.01; |

in the crystal form A of the sulfate salt, diffraction peaks in the X-ray powder diffraction pattern of the crystal form A expressed by 2θ angles are shown in the following table:

| Number | 2θ Angle/° |
|---|---|
| 1 | 6.70 |
| 2 | 8.70 |
| 3 | 10.12 |
| 4 | 13.53 |
| 5 | 14.14 |
| 6 | 14.29 |
| 7 | 14.94 |
| 8 | 16.11 |
| 9 | 16.78 |
| 10 | 17.25 |
| 11 | 17.42 |
| 12 | 18.45 |
| 13 | 18.97 |
| 14 | 19.48 |
| 15 | 19.62 |
| 16 | 20.46 |
| 17 | 20.87 |
| 18 | 21.06 |
| 19 | 22.40 |
| 20 | 22.53 |
| 21 | 22.77 |
| 22 | 23.07 |
| 23 | 23.50 |
| 24 | 24.18 |
| 25 | 24.49 |
| 26 | 24.78 |
| 27 | 25.01 |
| 28 | 25.80 |
| 29 | 26.14 |
| 30 | 26.46 |
| 31 | 26.67 |
| 32 | 27.19 |
| 33 | 27.46 |

-continued

| Number | 2θ Angle/° |
|---|---|
| 34 | 28.71 |
| 35 | 28.95 |
| 36 | 32.36 |
| 37 | 33.43 |
| 38 | 34.15 |
| 39 | 37.89 |
| 40 | 38.89 |
| 41 | 39.49; |

in the crystal form B of the sulfate salt, diffraction peaks in the X-ray powder diffraction pattern of the crystal form B expressed by 2θ angles are shown in the following table:

| Number | 2θ Angle/° |
|---|---|
| 1 | 9.00 |
| 2 | 10.48 |
| 3 | 12.52 |
| 4 | 15.86 |
| 5 | 16.53 |
| 6 | 17.44 |
| 7 | 17.93 |
| 8 | 19.03 |
| 9 | 20.50 |
| 10 | 21.21 |
| 11 | 22.36 |
| 12 | 23.25 |
| 13 | 24.24 |
| 14 | 25.94 |
| 15 | 27.61 |
| 16 | 28.46 |
| 17 | 29.04 |
| 18 | 30.59; |

in the crystal form C of the sulfate salt, diffraction peaks in the X-ray powder diffraction pattern of the crystal form C expressed by 2θ angles are shown in the following table:

| Number | 2θ Angle/° |
|---|---|
| 1 | 6.72 |
| 2 | 7.70 |
| 3 | 8.53 |
| 4 | 8.74 |
| 5 | 10.67 |
| 6 | 12.87 |
| 7 | 13.57 |
| 8 | 14.38 |
| 9 | 14.78 |
| 10 | 15.53 |
| 11 | 17.42 |
| 12 | 18.34 |
| 13 | 18.64 |
| 14 | 19.05 |
| 15 | 19.87 |
| 16 | 20.50 |
| 17 | 21.29 |
| 18 | 21.55 |
| 19 | 22.41 |
| 20 | 23.03 |
| 21 | 23.35 |
| 22 | 24.22 |
| 23 | 24.55 |
| 24 | 24.85 |
| 25 | 25.94 |
| 26 | 26.74 |
| 27 | 27.55 |
| 28 | 28.40; |

in the crystal form A of the phosphate salt, diffraction peaks in the X-ray powder diffraction pattern of the crystal form A expressed by 2θ angles are shown in the following table:

| Number | 2θ Angle/° |
|---|---|
| 1 | 6.57 |
| 2 | 8.74 |
| 3 | 10.04 |
| 4 | 13.23 |
| 5 | 14.10 |
| 6 | 14.24 |
| 7 | 14.64 |
| 8 | 14.78 |
| 9 | 15.52 |
| 10 | 16.54 |
| 11 | 17.12 |
| 12 | 17.79 |
| 13 | 18.10 |
| 14 | 18.33 |
| 15 | 18.53 |
| 16 | 18.75 |
| 17 | 19.97 |
| 18 | 20.30 |
| 19 | 20.67 |
| 20 | 21.43 |
| 21 | 21.80 |
| 22 | 22.15 |
| 23 | 22.43 |
| 24 | 22.79 |
| 25 | 23.15 |
| 26 | 24.03 |
| 27 | 24.34 |
| 28 | 24.59 |
| 29 | 25.40 |
| 30 | 26.11 |
| 31 | 26.80 |
| 32 | 27.18 |
| 33 | 28.44 |
| 34 | 28.65 |
| 35 | 30.01 |
| 36 | 30.15 |
| 37 | 30.48 |
| 38 | 30.82 |
| 39 | 31.52 |
| 40 | 32.13 |
| 41 | 33.16 |
| 42 | 33.57 |
| 43 | 37.00 |
| 44 | 37.38 |
| 45 | 37.78 |
| 46 | 39.00 |
| 47 | 39.29; |

in the crystal form B of the phosphate salt, diffraction peaks in the X-ray powder diffraction pattern of the crystal form B expressed by 2θ angles are shown in the following table:

| Number | 2θ Angle/° |
|---|---|
| 1 | 7.40 |
| 2 | 8.27 |
| 3 | 8.60 |
| 4 | 11.48 |
| 5 | 12.57 |
| 6 | 14.27 |
| 7 | 16.12 |
| 8 | 16.58 |
| 9 | 17.00 |
| 10 | 17.37 |
| 11 | 17.60 |
| 12 | 17.96 |
| 13 | 19.69 |
| 14 | 19.99 |
| 15 | 20.55 |

-continued

| Number | 2θ Angle/° |
|---|---|
| 16 | 21.10 |
| 17 | 21.41 |
| 18 | 21.81 |
| 19 | 22.21 |
| 20 | 22.43 |
| 21 | 23.38 |
| 22 | 24.32 |
| 23 | 24.93 |
| 24 | 26.26 |
| 25 | 26.69 |
| 26 | 26.91 |
| 27 | 28.93 |
| 28 | 29.17 |
| 29 | 30.10 |
| 30 | 33.34 |
| 31 | 34.00; |

in the crystal form A of the sodium salt, diffraction peaks in the X-ray powder diffraction pattern of the crystal form A expressed by 2θ angles are shown in the following table:

| Number | 2θ Angle/° |
|---|---|
| 1 | 7.04 |
| 2 | 9.78 |
| 3 | 10.23 |
| 4 | 11.05 |
| 5 | 11.36 |
| 6 | 11.55 |
| 7 | 11.69 |
| 8 | 12.52 |
| 9 | 13.86 |
| 10 | 14.20 |
| 11 | 14.37 |
| 12 | 15.19 |
| 13 | 15.45 |
| 14 | 15.80 |
| 15 | 16.22 |
| 16 | 16.60 |
| 17 | 17.98 |
| 18 | 18.15 |
| 19 | 18.36 |
| 20 | 18.81 |
| 21 | 19.71 |
| 22 | 19.97 |
| 23 | 20.43 |
| 24 | 21.13 |
| 25 | 21.27 |
| 26 | 21.47 |
| 27 | 21.71 |
| 28 | 22.10 |
| 29 | 22.40 |
| 30 | 22.87 |
| 31 | 23.35 |
| 32 | 23.61 |
| 33 | 23.94 |
| 34 | 24.13 |
| 35 | 25.34 |
| 36 | 25.65 |
| 37 | 25.98 |
| 38 | 26.45 |
| 39 | 26.72 |
| 40 | 26.96 |
| 41 | 27.14 |
| 42 | 27.39 |
| 43 | 27.80 |
| 44 | 28.01 |
| 45 | 28.76 |
| 46 | 29.13 |
| 47 | 30.63 |
| 48 | 32.11 |
| 49 | 32.66 |
| 50 | 32.90 |

-continued

| Number | 2θ Angle/° |
|---|---|
| 51 | 33.36 |
| 52 | 33.99 |
| 53 | 34.39 |
| 54 | 34.82 |
| 55 | 35.48 |
| 56 | 35.88 |
| 57 | 36.26 |
| 58 | 36.69 |
| 59 | 37.05 |
| 60 | 37.38 |
| 61 | 38.15 |
| 62 | 38.34 |
| 63 | 38.54; |

in the crystal form A of the potassium salt, diffraction peaks in the X-ray powder diffraction pattern of the crystal form A expressed by 2θ angles are shown in the following table:

| Number | 2θ Angle/° |
|---|---|
| 1 | 7.04 |
| 2 | 9.76 |
| 3 | 10.28 |
| 4 | 11.05 |
| 5 | 11.48 |
| 6 | 13.77 |
| 7 | 14.21 |
| 8 | 15.06 |
| 9 | 15.49 |
| 10 | 16.23 |
| 11 | 16.56 |
| 12 | 17.85 |
| 13 | 18.06 |
| 14 | 18.66 |
| 15 | 19.46 |
| 16 | 19.96 |
| 17 | 20.35 |
| 18 | 20.72 |
| 19 | 20.97 |
| 20 | 21.30 |
| 21 | 21.58 |
| 22 | 22.50 |
| 23 | 22.88 |
| 24 | 23.54 |
| 25 | 23.88 |
| 26 | 24.07 |
| 27 | 25.58 |
| 28 | 26.03 |
| 29 | 26.75 |
| 30 | 26.97 |
| 31 | 27.38 |
| 32 | 27.92 |
| 33 | 28.76 |
| 34 | 30.56 |
| 35 | 30.93 |
| 36 | 32.58 |
| 37 | 33.01 |
| 38 | 33.69 |
| 39 | 34.44. |

12. The crystal form according to claim 8, wherein the crystal form A of the hydrochloride salt satisfies one or more of the following conditions:

(1) in the crystal form A of the hydrochloride salt, diffraction peaks and relative intensities in the X-ray powder diffraction pattern of the crystal form A expressed by 2θ angles and relative intensities are shown in the following table:

| Number | 2θ Angle/° | Relative Intensity/% |
|---|---|---|
| 1 | 7.37 | 36.01 |
| 2 | 9.06 | 3.59 |
| 3 | 10.81 | 7.77 |
| 4 | 11.24 | 2.66 |
| 5 | 11.72 | 75.99 |
| 6 | 12.60 | 3.84 |
| 7 | 13.67 | 23.57 |
| 8 | 14.91 | 4.83 |
| 9 | 15.20 | 9.70 |
| 10 | 16.26 | 18.08 |
| 11 | 16.76 | 17.45 |
| 12 | 17.10 | 5.33 |
| 13 | 18.12 | 30.64 |
| 14 | 18.45 | 100.00 |
| 15 | 18.79 | 29.90 |
| 16 | 19.26 | 3.08 |
| 17 | 19.68 | 4.03 |
| 18 | 19.97 | 71.79 |
| 19 | 20.20 | 25.35 |
| 20 | 20.46 | 16.12 |
| 21 | 21.01 | 9.74 |
| 22 | 21.16 | 2.32 |
| 23 | 21.32 | 2.27 |
| 24 | 21.88 | 58.88 |
| 25 | 22.50 | 4.04 |
| 26 | 22.70 | 33.39 |
| 27 | 23.00 | 5.40 |
| 28 | 23.74 | 7.95 |
| 29 | 24.18 | 26.66 |
| 30 | 24.51 | 1.87 |
| 31 | 24.96 | 4.32 |
| 32 | 25.32 | 4.69 |
| 33 | 25.53 | 26.11 |
| 34 | 25.68 | 6.57 |
| 35 | 26.02 | 53.73 |
| 36 | 26.34 | 6.08 |
| 37 | 26.64 | 4.71 |
| 38 | 26.89 | 4.40 |
| 39 | 27.70 | 3.30 |
| 40 | 28.04 | 4.87 |
| 41 | 28.39 | 5.80 |
| 42 | 28.61 | 33.77 |
| 43 | 28.84 | 2.44 |
| 44 | 29.24 | 4.23 |
| 45 | 29.89 | 22.55 |
| 46 | 30.18 | 4.77 |
| 47 | 31.00 | 3.91 |
| 48 | 31.27 | 20.50 |
| 49 | 32.58 | 3.16 |
| 50 | 32.99 | 6.18 |
| 51 | 33.55 | 2.49 |
| 52 | 33.91 | 7.17 |
| 53 | 35.80 | 2.64 |
| 54 | 36.28 | 1.61 |
| 55 | 36.90 | 2.07 |
| 56 | 37.23 | 15.53 |
| 57 | 37.38 | 10.29 |
| 58 | 38.28 | 2.79 |
| 59 | 38.57 | 4.30 |
| 60 | 39.32 | 11.50 |
| 61 | 39.54 | 4.26; |

(2) the crystal form A of the hydrochloride salt has a thermal gravimetric analysis pattern showing a weight loss of 2.070% at 125.06° C.; the "%" represents mass percentage;

(3) the crystal form A has a differential scanning calorimetry analysis pattern showing an onset of an endothermic peak at 184.04±2° C., and reaches a peak value of the endothermic peak at 188.62±2° C.; and has an enthalpy value of 344.80 J/g;

the crystal form B of the hydrochloride salt satisfies one or more of the following conditions:

(1) in the crystal form B of the hydrochloride salt, diffraction peaks and relative intensities in the X-ray powder diffraction pattern of the crystal form B expressed by 2θ angles and relative intensities are shown in the following table:

| Number | 2θ Angle/° | Relative Intensity/% |
|---|---|---|
| 1 | 7.37 | 4.70 |
| 2 | 7.70 | 15.07 |
| 3 | 8.20 | 8.58 |
| 4 | 13.02 | 7.88 |
| 5 | 13.28 | 6.95 |
| 6 | 13.93 | 17.06 |
| 7 | 14.78 | 17.67 |
| 8 | 14.89 | 6.60 |
| 9 | 15.28 | 21.74 |
| 10 | 15.58 | 29.78 |
| 11 | 16.85 | 49.54 |
| 12 | 18.07 | 36.85 |
| 13 | 18.18 | 12.64 |
| 14 | 18.54 | 9.66 |
| 15 | 18.87 | 20.22 |
| 16 | 19.51 | 4.71 |
| 17 | 20.18 | 17.14 |
| 18 | 21.08 | 5.60 |
| 19 | 21.43 | 5.65 |
| 20 | 21.62 | 15.34 |
| 21 | 22.51 | 26.94 |
| 22 | 24.21 | 35.79 |
| 23 | 24.45 | 13.47 |
| 24 | 24.69 | 8.62 |
| 25 | 25.07 | 6.87 |
| 26 | 25.88 | 26.18 |
| 27 | 26.40 | 100.00 |
| 28 | 26.61 | 12.46 |
| 29 | 26.90 | 15.65 |
| 30 | 27.18 | 32.10 |
| 31 | 28.99 | 6.89 |
| 32 | 29.99 | 2.75 |
| 33 | 31.68 | 5.43 |
| 34 | 31.89 | 3.26 |
| 35 | 32.28 | 9.17 |
| 36 | 32.58 | 2.64 |
| 37 | 33.53 | 4.05 |
| 38 | 33.89 | 4.61 |
| 39 | 34.36 | 7.05 |
| 40 | 34.58 | 10.26 |
| 41 | 34.76 | 4.78 |
| 42 | 35.21 | 5.49 |
| 43 | 35.72 | 6.06 |
| 44 | 37.54 | 1.35 |
| 45 | 37.75 | 5.80 |
| 46 | 38.45 | 6.20 |
| 47 | 39.01 | 3.80; |

(2) the crystal form B of the hydrochloride salt has a thermal gravimetric analysis pattern showing a weight loss of 7.216% at 96.43° C.; the "%" represents mass percentage;

(3) the crystal form B has a differential scanning calorimetry analysis pattern showing an onset of an endothermic peak at 173.54±2° C., and reaches a peak value of the endothermic peak at 184.54±2° C.; and has an enthalpy value of 259.36 J/g;

the crystal form A of the sulfate salt satisfies one or more of the following conditions:

(1) in the crystal form A of the sulfate salt, diffraction peaks and relative intensities in the X-ray powder diffraction pattern of the crystal form A expressed by 2θ angles and relative intensities are shown in the following table:

| Number | 2θ Angle/° | Relative Intensity/% |
|---|---|---|
| 1 | 6.70 | 11.30 |
| 2 | 8.70 | 89.89 |
| 3 | 10.12 | 20.98 |
| 4 | 13.53 | 18.48 |
| 5 | 14.14 | 11.75 |
| 6 | 14.29 | 33.44 |
| 7 | 14.94 | 21.72 |
| 8 | 16.11 | 33.48 |
| 9 | 16.78 | 32.28 |
| 10 | 17.25 | 3.85 |
| 11 | 17.42 | 19.13 |
| 12 | 18.45 | 11.11 |
| 13 | 18.97 | 21.83 |
| 14 | 19.48 | 3.25 |
| 15 | 19.62 | 7.45 |
| 16 | 20.46 | 100.00 |
| 17 | 20.87 | 26.20 |
| 18 | 21.06 | 11.87 |
| 19 | 22.40 | 3.32 |
| 20 | 22.53 | 7.49 |
| 21 | 22.77 | 31.90 |
| 22 | 23.07 | 2.58 |
| 23 | 23.50 | 10.91 |
| 24 | 24.18 | 22.88 |
| 25 | 24.49 | 57.84 |
| 26 | 24.78 | 37.97 |
| 27 | 25.01 | 7.00 |
| 28 | 25.80 | 3.52 |
| 29 | 26.14 | 6.31 |
| 30 | 26.46 | 13.48 |
| 31 | 26.67 | 20.63 |
| 32 | 27.19 | 12.62 |
| 33 | 27.46 | 14.71 |
| 34 | 28.71 | 6.06 |
| 35 | 28.95 | 6.19 |
| 36 | 32.36 | 5.15 |
| 37 | 33.43 | 6.27 |
| 38 | 34.15 | 7.30 |
| 39 | 37.89 | 7.71 |
| 40 | 38.89 | 5.71 |
| 41 | 39.49 | 3.17; |

(2) the crystal form A of the sulfate salt has a thermal gravimetric analysis pattern showing a weight loss of 3.880% at 118.49° C.; the "%" represents mass percentage;

(3) the crystal form A has a differential scanning calorimetry analysis pattern showing an onset of an endothermic peak at 149.86±2° C., and reaches a peak value of the endothermic peak at 160.23±2° C.; and has an enthalpy value of 229.21 J/g;

the crystal form B of the sulfate salt satisfies one or more of the following conditions:

(1) in the crystal form B of the sulfate salt, diffraction peaks and relative intensities in the X-ray powder diffraction pattern of the crystal form B expressed by 2θ angles and relative intensities are shown in the following table:

| Number | 2θ Angle/° | Relative Intensity/% |
|---|---|---|
| 1 | 9.00 | 48.50 |
| 2 | 10.48 | 9.08 |
| 3 | 12.52 | 50.23 |
| 4 | 15.86 | 9.46 |
| 5 | 16.53 | 10.26 |
| 6 | 17.44 | 5.91 |
| 7 | 17.93 | 4.51 |
| 8 | 19.03 | 10.62 |
| 9 | 20.50 | 30.90 |
| 10 | 21.21 | 100.00 |
| 11 | 22.36 | 76.43 |
| 12 | 23.25 | 22.69 |

-continued

| Number | 2θ Angle/° | Relative Intensity/% |
|---|---|---|
| 13 | 24.24 | 9.68 |
| 14 | 25.94 | 18.77 |
| 15 | 27.61 | 23.48 |
| 16 | 28.46 | 15.18 |
| 17 | 29.04 | 6.60 |
| 18 | 30.59 | 29.81; |

(2) the crystal form B of the sulfate salt has a thermal gravimetric analysis pattern showing a weight loss of 6.895% at 92.04° C.; the "%" represents mass percentage;

(3) the crystal form B has a differential scanning calorimetry analysis pattern showing an onset of an endothermic peak at 126.34±2° C., and reaches a peak value of the endothermic peak at 139.98±2° C.; and has an enthalpy value of 230.50 J/g;

the crystal form C of the sulfate salt satisfies one or more of the following conditions:

(1) in the crystal form C of the sulfate salt, diffraction peaks and relative intensities in the X-ray powder diffraction pattern of the crystal form C expressed by 2θ angles and relative intensities are shown in the following table:

| Number | 2θ Angle/° | Relative Intensity/% |
|---|---|---|
| 1 | 6.72 | 10.88 |
| 2 | 7.70 | 13.86 |
| 3 | 8.53 | 21.83 |
| 4 | 8.74 | 13.91 |
| 5 | 10.67 | 7.39 |
| 6 | 12.87 | 27.52 |
| 7 | 13.57 | 7.10 |
| 8 | 14.38 | 32.55 |
| 9 | 14.78 | 11.30 |
| 10 | 15.53 | 16.49 |
| 11 | 17.42 | 13.53 |
| 12 | 18.34 | 17.52 |
| 13 | 18.64 | 11.56 |
| 14 | 19.05 | 20.18 |
| 15 | 19.87 | 14.35 |
| 16 | 20.50 | 13.78 |
| 17 | 21.29 | 57.72 |
| 18 | 21.55 | 100.00 |
| 19 | 22.41 | 75.28 |
| 20 | 23.03 | 14.56 |
| 21 | 23.35 | 19.69 |
| 22 | 24.22 | 11.28 |
| 23 | 24.55 | 14.26 |
| 24 | 24.85 | 8.50 |
| 25 | 25.94 | 51.32 |
| 26 | 26.74 | 9.46 |
| 27 | 27.55 | 10.67 |
| 28 | 28.40 | 20.19; |

(2) the crystal form C of the sulfate salt has a thermal gravimetric analysis pattern showing a weight loss of 10.471% at 102.19° C.; the "%" represents mass percentage;

(3) the crystal form C has a differential scanning calorimetry analysis pattern showing an onset of an endothermic peak at 117.30±2° C., and reaches a peak value of the endothermic peak at 122.26±2° C.; and has an enthalpy value of 54.426 J/g;

the crystal form A of the phosphate salt satisfies one or more of the following conditions:

(1) in the crystal form A of the phosphate salt, diffraction peaks and relative intensities in the X-ray powder diffraction pattern of the crystal form A expressed by 2θ angles and relative intensities are shown in the following table:

| Number | 2θ Angle/° | Relative Intensity/% |
|---|---|---|
| 1 | 6.57 | 75.66 |
| 2 | 8.74 | 100.00 |
| 3 | 10.04 | 11.10 |
| 4 | 13.23 | 29.20 |
| 5 | 14.10 | 6.52 |
| 6 | 14.24 | 4.71 |
| 7 | 14.64 | 4.03 |
| 8 | 14.78 | 6.29 |
| 9 | 15.52 | 48.30 |
| 10 | 16.54 | 13.08 |
| 11 | 17.12 | 2.96 |
| 12 | 17.79 | 8.17 |
| 13 | 18.10 | 5.62 |
| 14 | 18.33 | 1.24 |
| 15 | 18.53 | 5.68 |
| 16 | 18.75 | 2.09 |
| 17 | 19.97 | 68.80 |
| 18 | 20.30 | 31.67 |
| 19 | 20.67 | 10.76 |
| 20 | 21.43 | 2.89 |
| 21 | 21.80 | 4.42 |
| 22 | 22.15 | 4.98 |
| 23 | 22.43 | 8.59 |
| 24 | 22.79 | 17.34 |
| 25 | 23.15 | 2.86 |
| 26 | 24.03 | 6.25 |
| 27 | 24.34 | 14.16 |
| 28 | 24.59 | 11.80 |
| 29 | 25.40 | 10.69 |
| 30 | 26.11 | 5.04 |
| 31 | 26.80 | 23.50 |
| 32 | 27.18 | 7.35 |
| 33 | 28.44 | 5.05 |
| 34 | 28.65 | 1.63 |
| 35 | 30.01 | 2.19 |
| 36 | 30.15 | 1.57 |
| 37 | 30.48 | 3.17 |
| 38 | 30.82 | 5.31 |
| 39 | 31.52 | 1.21 |
| 40 | 32.13 | 3.31 |
| 41 | 33.16 | 2.37 |
| 42 | 33.57 | 3.95 |
| 43 | 37.00 | 3.20 |
| 44 | 37.38 | 3.89 |
| 45 | 37.78 | 4.99 |
| 46 | 39.00 | 7.81 |
| 47 | 39.29 | 3.96; |

(2) the crystal form A of the phosphate salt has a thermal gravimetric analysis pattern showing a weight loss of 0.776% at 142.87° C.; the "%" represents mass percentage;

(3) the crystal form A has a differential scanning calorimetry analysis pattern showing an onset of an endothermic peak at 179.76±2° C., and reaches a peak value of the endothermic peak at 180.61±2° C.; and has an enthalpy value of 265.82 J/g;

the crystal form B of the phosphate salt satisfies one or more of the following conditions:

(1) in the crystal form B of the phosphate salt, diffraction peaks and relative intensities in the X-ray powder diffraction pattern of the crystal form B expressed by 2θ angles and relative intensities are shown in the following table:

| Number | 2θ Angle/° | Relative Intensity/% |
|---|---|---|
| 1 | 7.40 | 46.75 |
| 2 | 8.27 | 23.62 |
| 3 | 8.60 | 24.03 |
| 4 | 11.48 | 1.21 |
| 5 | 12.57 | 32.13 |
| 6 | 14.27 | 13.47 |
| 7 | 16.12 | 3.26 |
| 8 | 16.58 | 19.21 |
| 9 | 17.00 | 15.96 |
| 10 | 17.37 | 23.05 |
| 11 | 17.60 | 32.63 |
| 12 | 17.96 | 100.00 |
| 13 | 19.69 | 21.01 |
| 14 | 19.99 | 12.91 |
| 15 | 20.55 | 11.19 |
| 16 | 21.10 | 2.53 |
| 17 | 21.41 | 21.86 |
| 18 | 21.81 | 18.04 |
| 19 | 22.21 | 10.66 |
| 20 | 22.43 | 21.14 |
| 21 | 23.38 | 3.83 |
| 22 | 24.32 | 46.26 |
| 23 | 24.93 | 12.48 |
| 24 | 26.26 | 9.46 |
| 25 | 26.69 | 7.28 |
| 26 | 26.91 | 41.15 |
| 27 | 28.93 | 4.10 |
| 28 | 29.17 | 1.50 |
| 29 | 30.10 | 7.53 |
| 30 | 33.34 | 15.02 |
| 31 | 34.00 | 4.71; |

(2) the crystal form B of the phosphate salt has a thermal gravimetric analysis pattern showing a weight loss of 1.071% at 74.52° C.; the "%" represents mass percentage;

(3) the crystal form B has a differential scanning calorimetry analysis pattern showing an onset of an endothermic peak at 159.94±2° C., and reaches a peak value of the endothermic peak at 169.82±2° C.; and has an enthalpy value of 77.238 J/g;

the crystal form A of the sodium salt satisfies one or more of the following conditions:

(1) in the crystal form A of the sodium salt, diffraction peaks and relative intensities in the X-ray powder diffraction pattern of the crystal form A expressed by 2θ angles and relative intensities are shown in the following table:

| Number | 2θ Angle/° | Relative Intensity/% |
|---|---|---|
| 1 | 7.04 | 94.24 |
| 2 | 9.78 | 52.18 |
| 3 | 10.23 | 16.52 |
| 4 | 11.05 | 70.55 |
| 5 | 11.36 | 8.33 |
| 6 | 11.55 | 17.04 |
| 7 | 11.69 | 0.38 |
| 8 | 12.52 | 2.29 |
| 9 | 13.86 | 2.51 |
| 10 | 14.20 | 61.97 |
| 11 | 14.37 | 8.29 |
| 12 | 15.19 | 6.46 |
| 13 | 15.45 | 10.23 |
| 14 | 15.80 | 7.14 |
| 15 | 16.22 | 6.98 |
| 16 | 16.60 | 8.33 |
| 17 | 17.98 | 26.11 |
| 18 | 18.15 | 25.57 |
| 19 | 18.36 | 7.63 |
| 20 | 18.81 | 100.00 |
| 21 | 19.71 | 4.66 |
| 22 | 19.97 | 15.97 |
| 23 | 20.43 | 56.69 |
| 24 | 21.13 | 11.53 |
| 25 | 21.27 | 30.04 |
| 26 | 21.47 | 2.87 |
| 27 | 21.71 | 6.10 |
| 28 | 22.10 | 5.93 |
| 29 | 22.40 | 23.61 |
| 30 | 22.87 | 23.72 |
| 31 | 23.35 | 2.52 |
| 32 | 23.61 | 9.38 |
| 33 | 23.94 | 26.65 |
| 34 | 24.13 | 23.38 |
| 35 | 25.34 | 2.23 |
| 36 | 25.65 | 58.17 |
| 37 | 25.98 | 20.02 |
| 38 | 26.45 | 6.11 |
| 39 | 26.72 | 7.30 |
| 40 | 26.96 | 15.00 |
| 41 | 27.14 | 3.51 |
| 42 | 27.39 | 3.34 |
| 43 | 27.80 | 3.85 |
| 44 | 28.01 | 12.30 |
| 45 | 28.76 | 36.73 |
| 46 | 29.13 | 3.17 |
| 47 | 30.63 | 2.86 |
| 48 | 32.11 | 1.84 |
| 49 | 32.66 | 9.66 |
| 50 | 32.90 | 9.18 |
| 51 | 33.36 | 2.21 |
| 52 | 33.99 | 2.61 |
| 53 | 34.39 | 6.04 |
| 54 | 34.82 | 3.74 |
| 55 | 35.48 | 3.60 |
| 56 | 35.88 | 1.53 |
| 57 | 36.26 | 1.47 |
| 58 | 36.69 | 15.38 |
| 59 | 37.05 | 2.39 |
| 60 | 37.38 | 1.35 |
| 61 | 38.15 | 0.86 |
| 62 | 38.34 | 10.48 |
| 63 | 38.54 | 5.74; |

(2) the crystal form A of the sodium salt has a thermal gravimetric analysis pattern showing a weight loss of 6.279% at 116.94° C.; the "%" represents mass percentage;

(3) the crystal form A has a differential scanning calorimetry analysis pattern showing an onset of an endothermic peak at 228.53±2° C., and reaches a peak value of the endothermic peak at 230.66±2° C.; and has an enthalpy value of 107.61 J/g;

the crystal form A of the potassium salt satisfies one or more of the following conditions:

(1) in the crystal form A of the potassium salt, diffraction peaks and relative intensities in the X-ray powder diffraction pattern of the crystal form A expressed by 2θ angles and relative intensities are shown in the following table:

| Number | 2θ Angle/° | Relative Intensity/% |
|---|---|---|
| 1 | 7.04 | 25.69 |
| 2 | 9.76 | 17.41 |
| 3 | 10.28 | 5.10 |
| 4 | 11.05 | 6.29 |
| 5 | 11.48 | 15.99 |
| 6 | 13.77 | 1.60 |
| 7 | 14.21 | 72.55 |
| 8 | 15.06 | 10.02 |
| 9 | 15.49 | 25.51 |

-continued

| Number | 2θ Angle/° | Relative Intensity/% |
|---|---|---|
| 10 | 16.23 | 2.54 |
| 11 | 16.56 | 5.98 |
| 12 | 17.85 | 21.03 |
| 13 | 18.06 | 11.65 |
| 14 | 18.66 | 53.46 |
| 15 | 19.46 | 17.87 |
| 16 | 19.96 | 19.71 |
| 17 | 20.35 | 6.36 |
| 18 | 20.72 | 5.03 |
| 19 | 20.97 | 19.73 |
| 20 | 21.30 | 15.56 |
| 21 | 21.58 | 2.45 |
| 22 | 22.50 | 23.44 |
| 23 | 22.88 | 13.73 |
| 24 | 23.54 | 32.35 |
| 25 | 23.88 | 6.23 |
| 26 | 24.07 | 57.22 |
| 27 | 25.58 | 100.00 |
| 28 | 26.03 | 20.71 |
| 29 | 26.75 | 11.42 |
| 30 | 26.97 | 16.86 |
| 31 | 27.38 | 8.76 |
| 32 | 27.92 | 23.58 |
| 33 | 28.76 | 51.14 |
| 34 | 30.56 | 2.76 |
| 35 | 30.93 | 7.85 |
| 36 | 32.58 | 5.39 |
| 37 | 33.01 | 6.45 |
| 38 | 33.69 | 3.97 |
| 39 | 34.44 | 2.57; |

(2) the crystal form A of the potassium salt has a thermal gravimetric analysis pattern showing a weight loss of 8.352% at 183.95° C.; the "%" represents mass percentage;

(3) the crystal form A has a differential scanning calorimetry analysis pattern showing an onset of an endothermic peak at 217.76±2° C., and reaches a peak value of the endothermic peak at 222.51±2° C.; and has an enthalpy value of 102.94 J/g.

Figure 17:
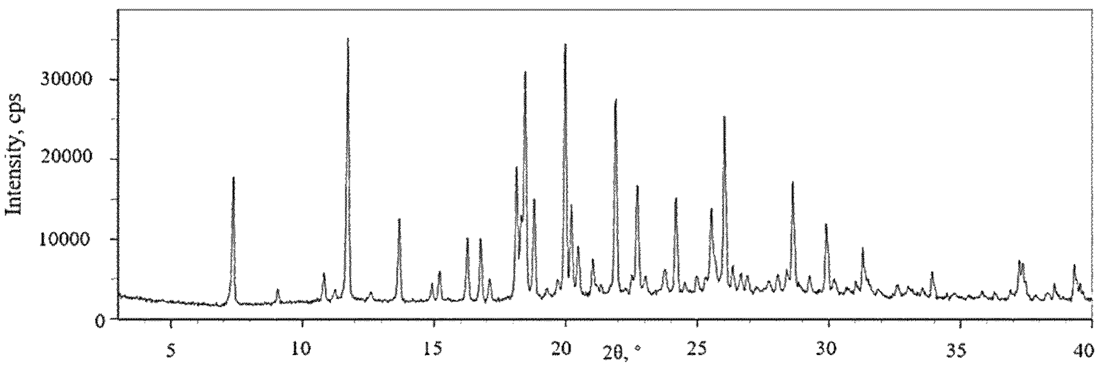
FIG. 17 shows the X-ray powder diffraction pattern of crystal form A of the hydrochloride salt.
Figure 18:
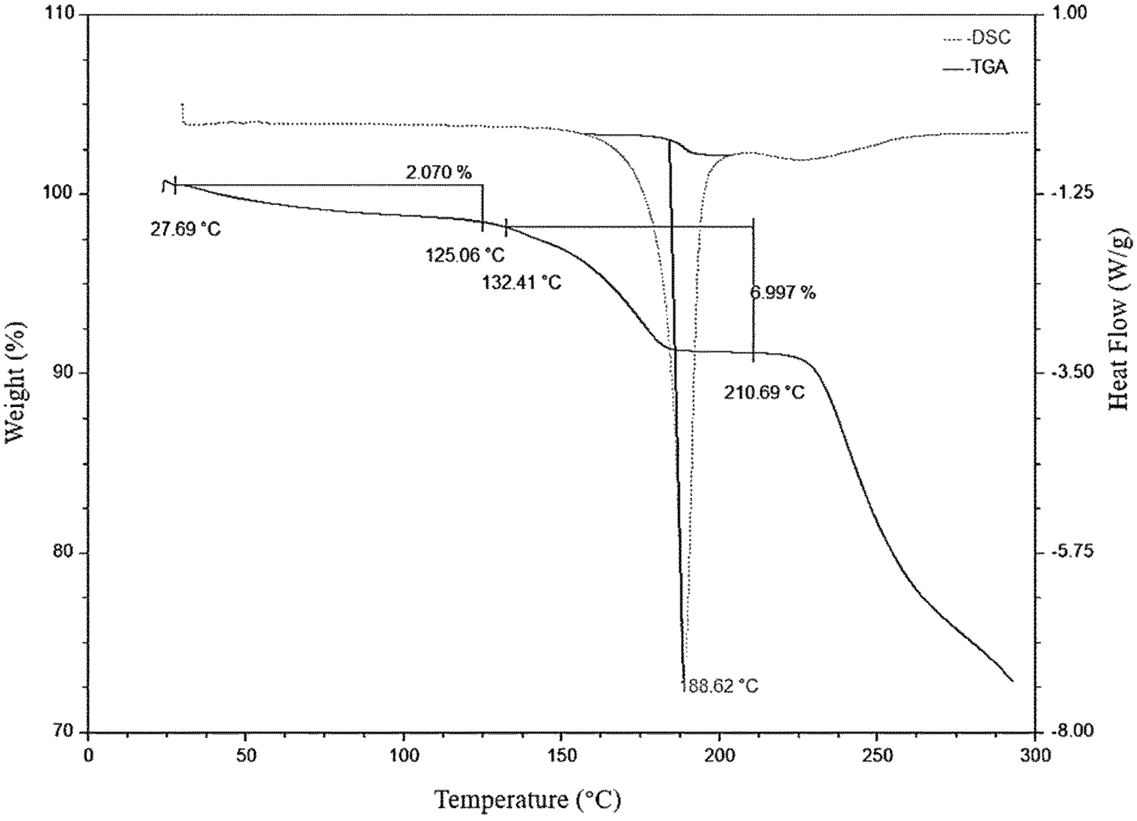
FIG. 18 shows the differential scanning calorimetry and thermal gravimetric analysis pattern of crystal form A of the hydrochloride salt.
Figure 19:
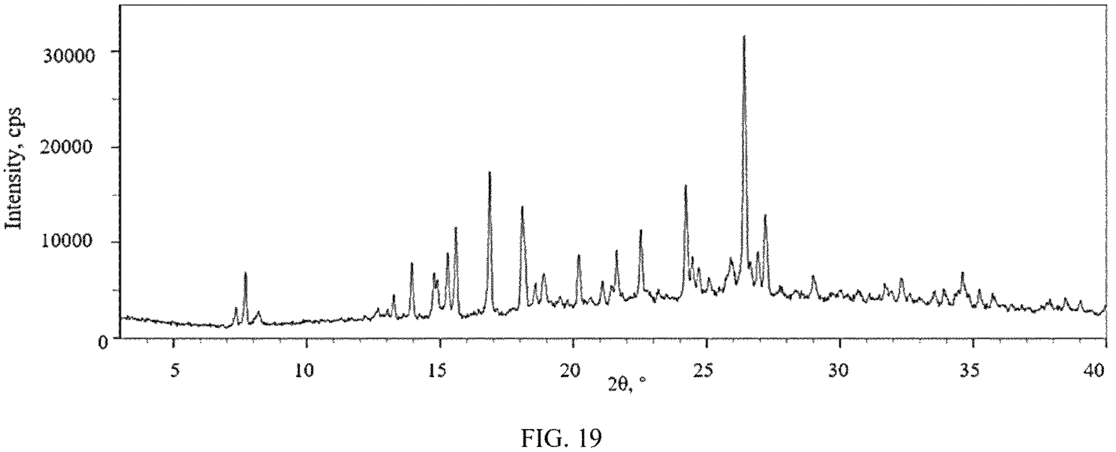
FIG. 19 shows the X-ray powder diffraction pattern of crystal form B of the hydrochloride salt.
Figure 20:
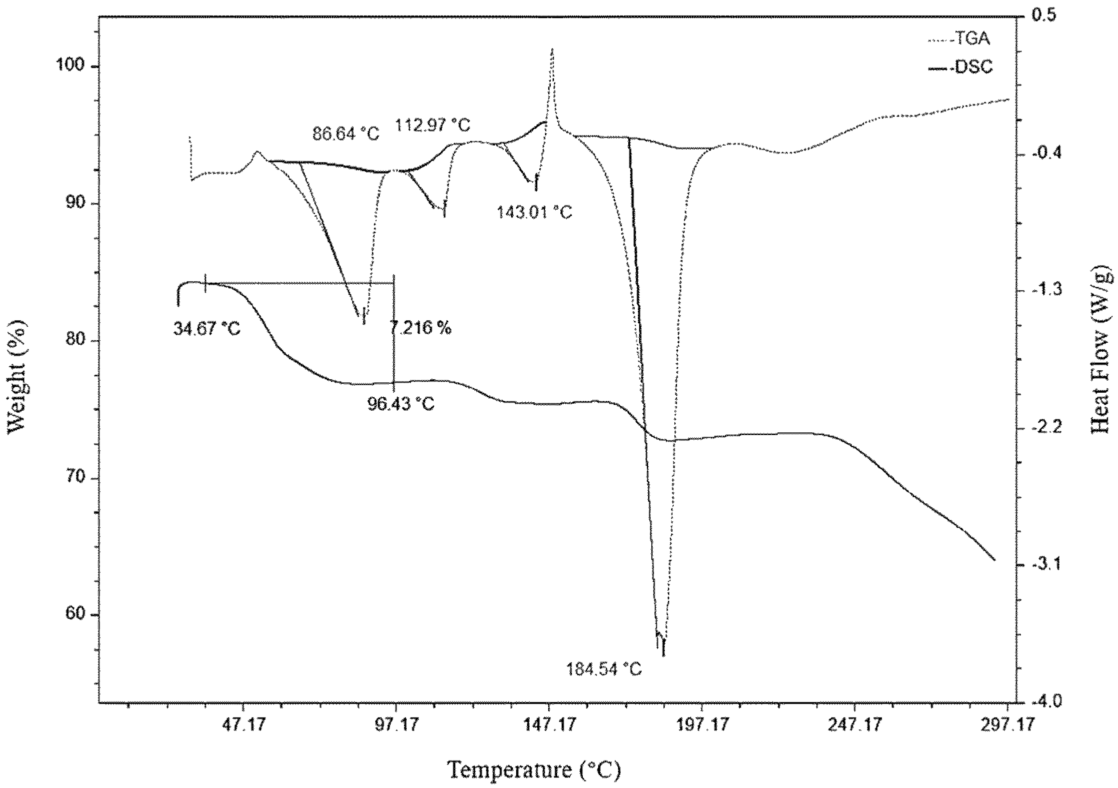
FIG. 20 shows the differential scanning calorimetry and thermal gravimetric analysis pattern of crystal form B of the hydrochloride salt.
Figure 21:
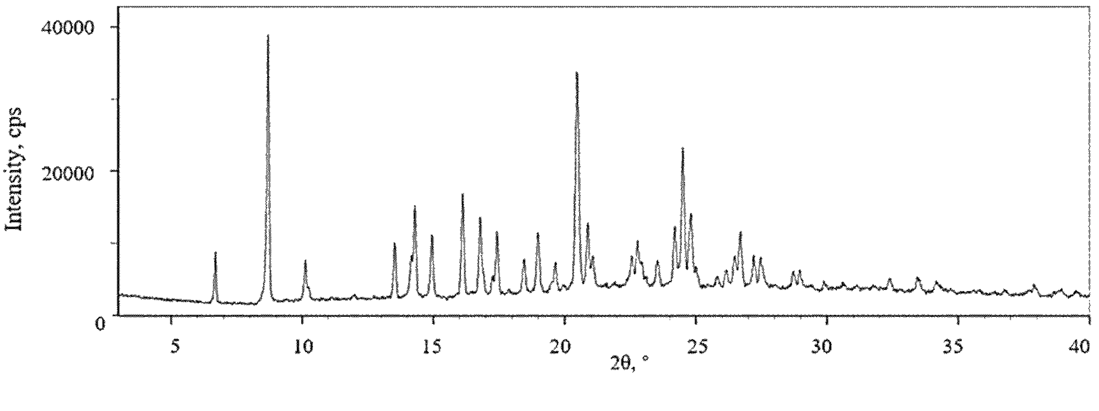
FIG. 21 shows the X-ray powder diffraction pattern of crystal form A of the sulfate salt.
Figure 22:
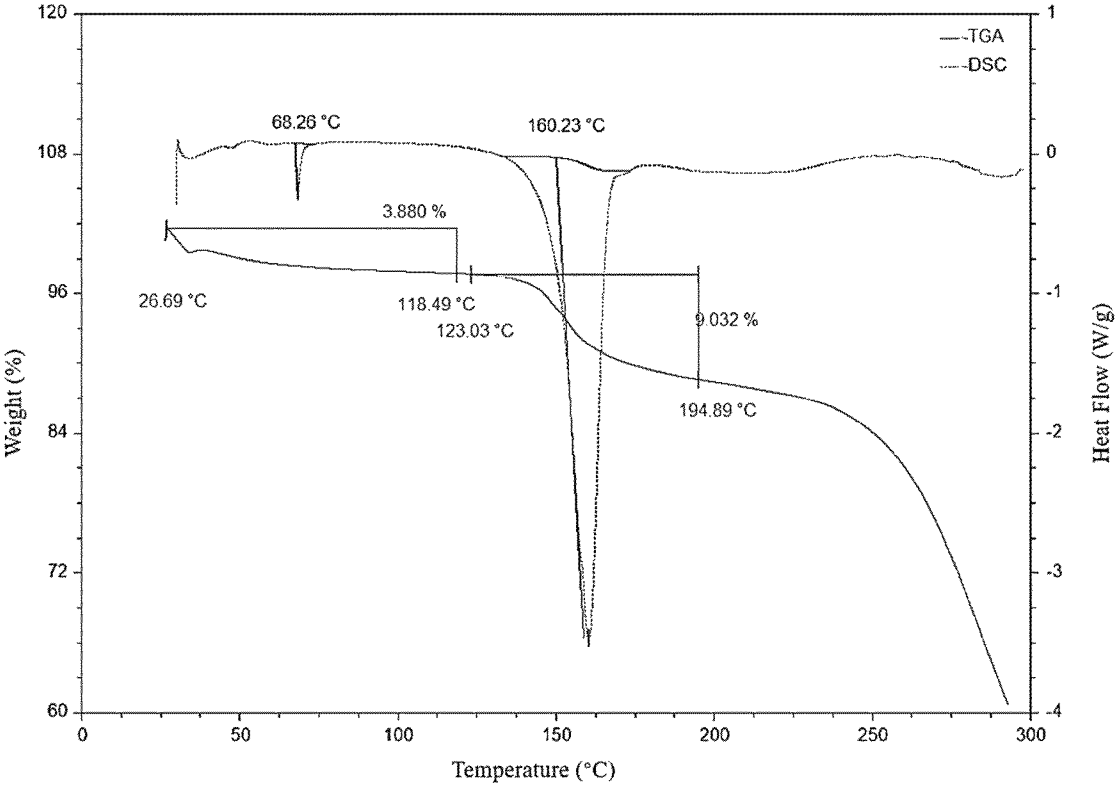
FIG. 22 shows the differential scanning calorimetry and thermal gravimetric analysis pattern of crystal form A of the sulfate salt.
Figure 23:
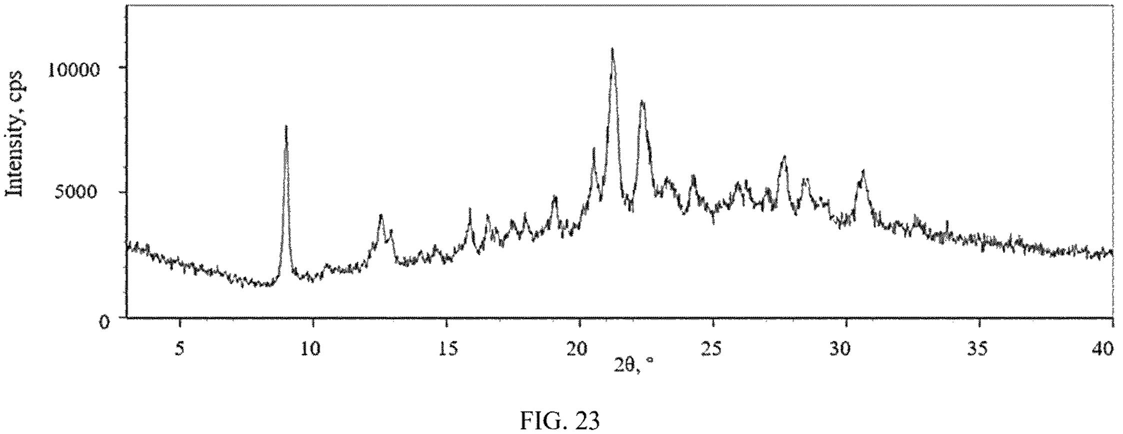
FIG. 23 shows the X-ray powder diffraction pattern of crystal form B of the sulfate salt.
Figure 24:
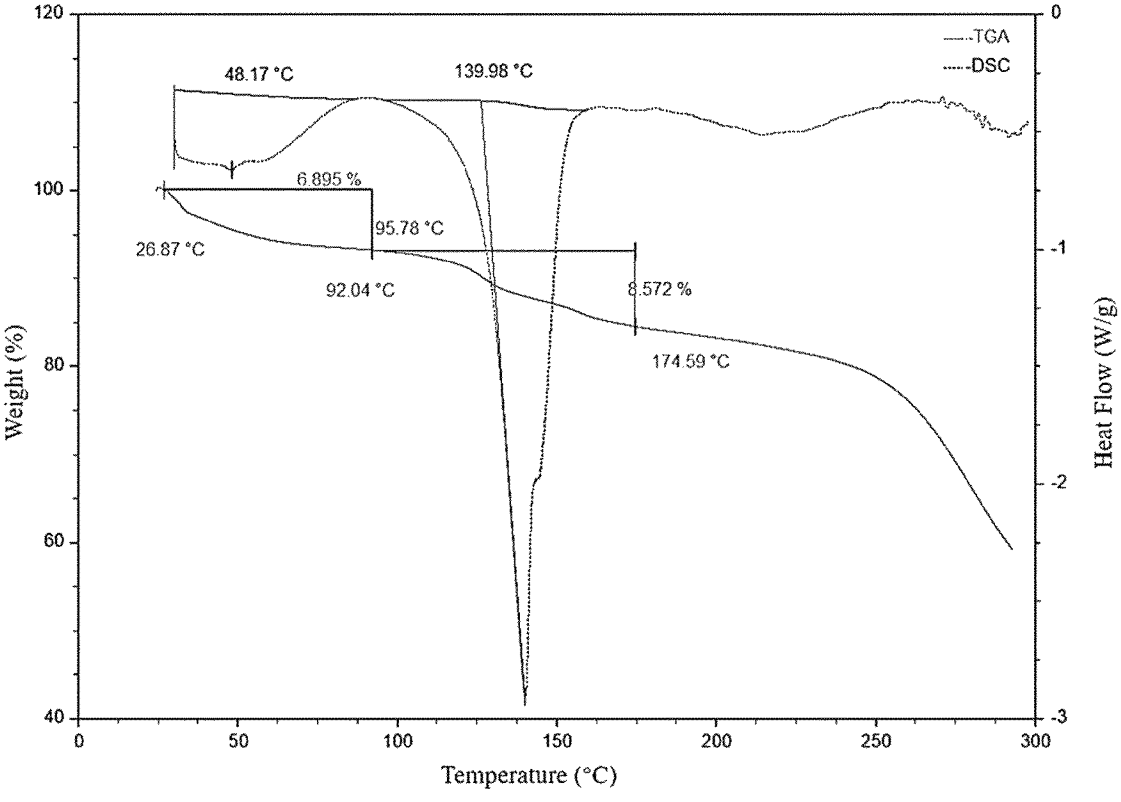
FIG. 24 shows the differential scanning calorimetry and thermal gravimetric analysis pattern of crystal form B of the sulfate salt.
Figure 25:
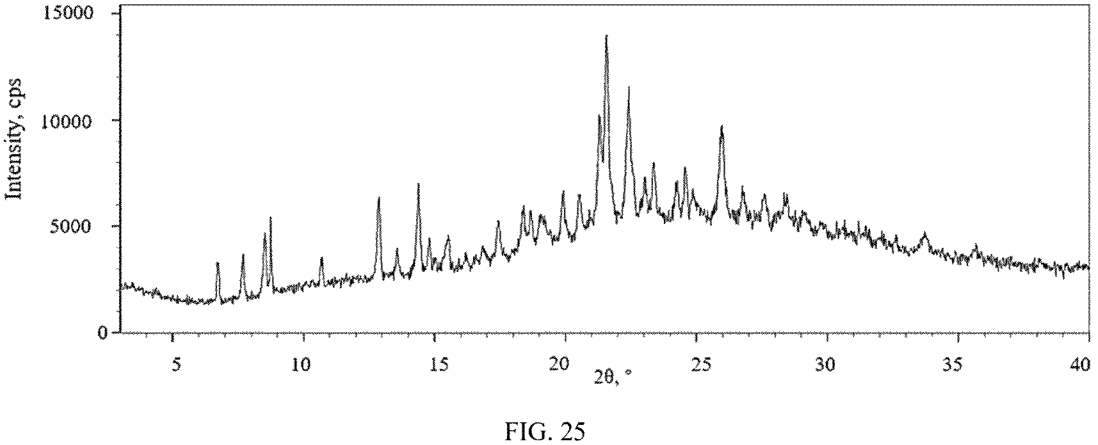
FIG. 25 shows the X-ray powder diffraction pattern of crystal form C of the sulfate salt.
Figure 26:
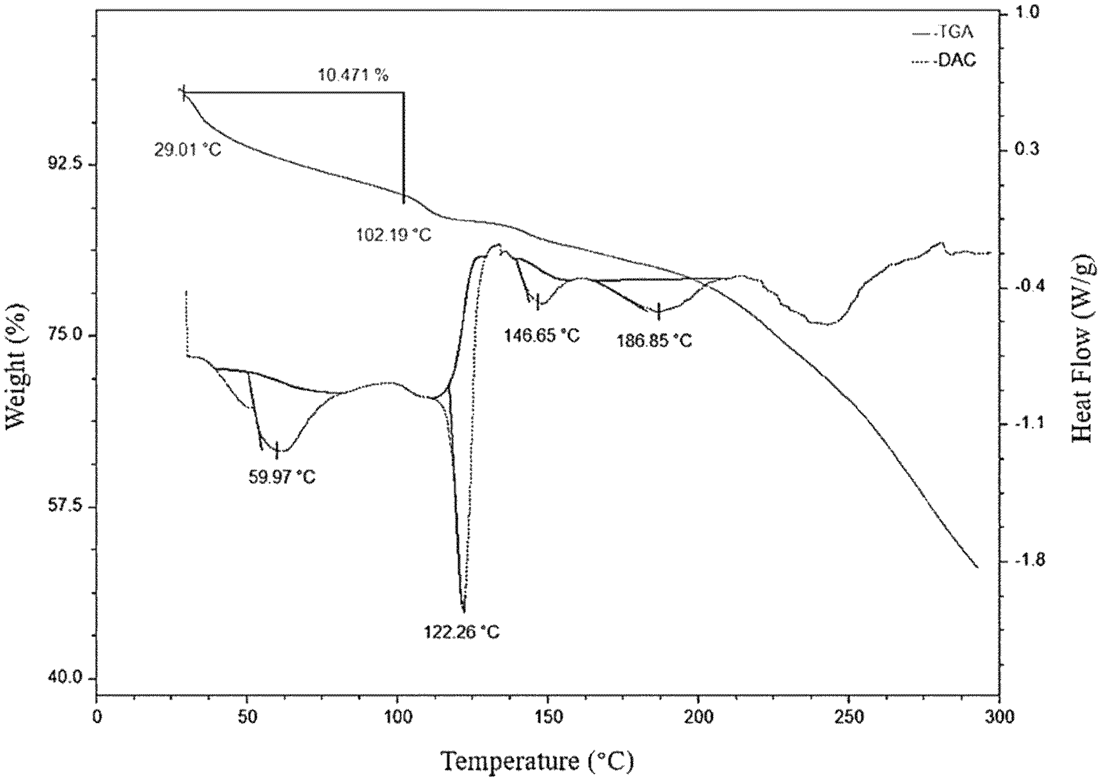
FIG. 26 shows the differential scanning calorimetry and thermal gravimetric analysis pattern of crystal form C of the sulfate salt.
Figure 27:
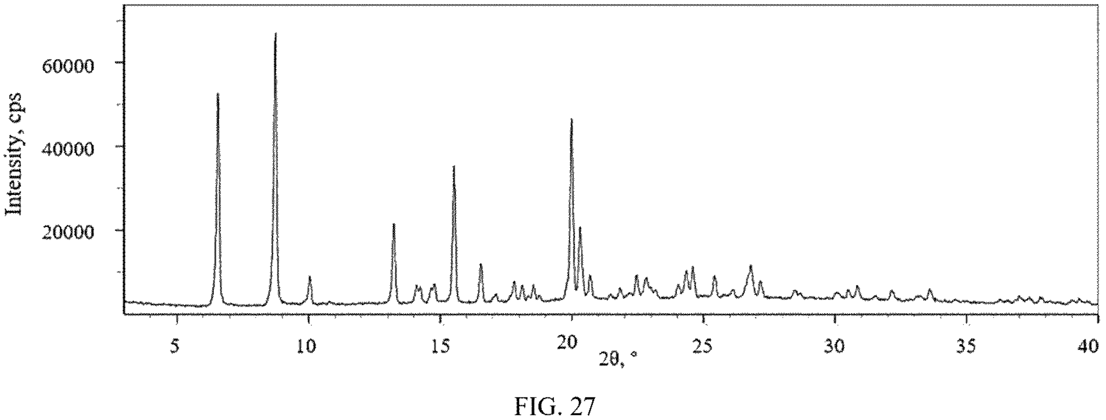
FIG. 27 shows the X-ray powder diffraction pattern of crystal form A of the phosphate salt.
Figure 28:
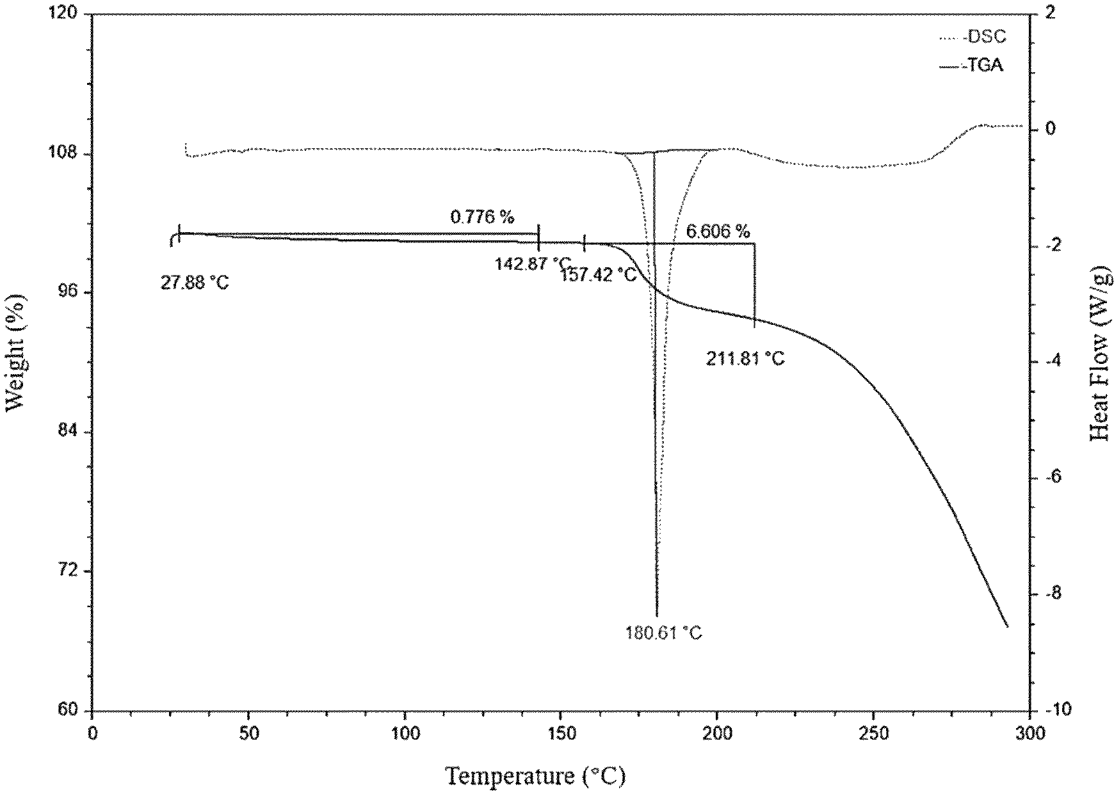
FIG. 28 shows the differential scanning calorimetry and thermal gravimetric analysis pattern of crystal form A of the phosphate salt.
Figure 29:
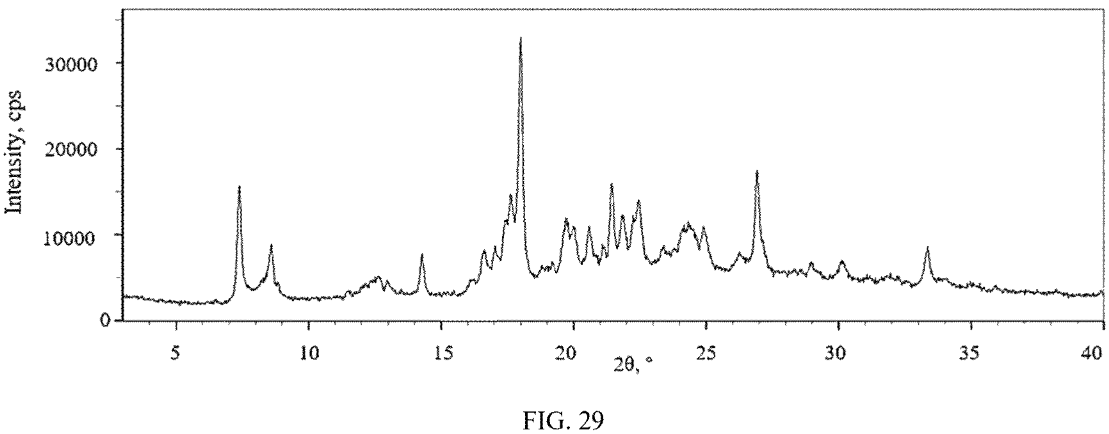
FIG. 29 shows the X-ray powder diffraction pattern of crystal form B of the phosphate salt.
Figure 30:
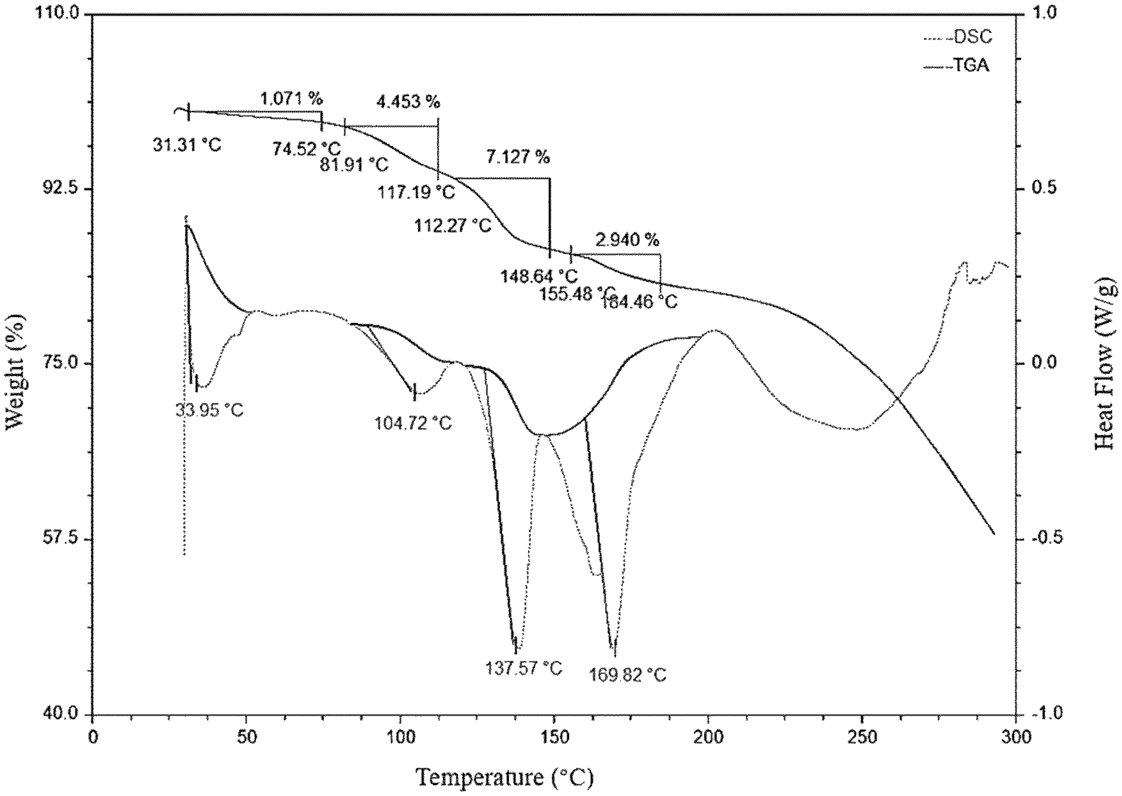
FIG. 30 shows the differential scanning calorimetry and thermal gravimetric analysis pattern of crystal form B of the phosphate salt.
Figure 31:
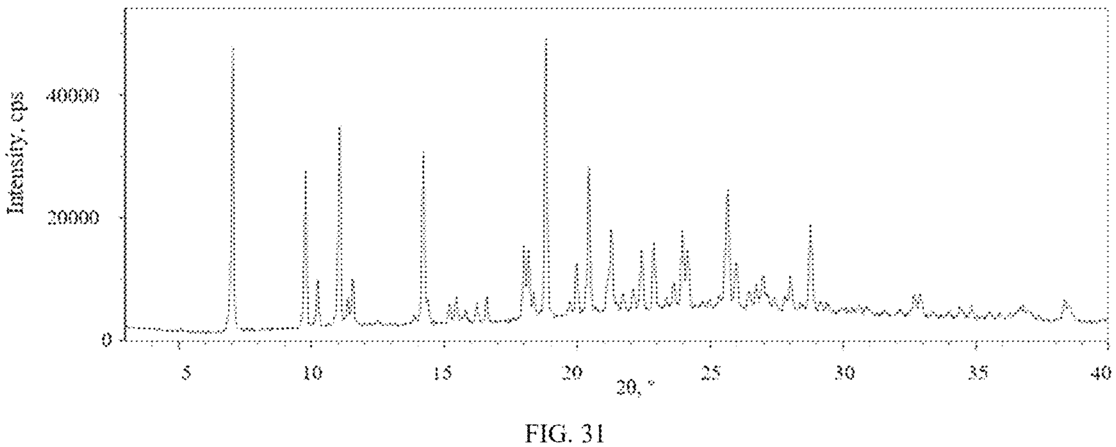
FIG. 31 shows the X-ray powder diffraction pattern of crystal form A of the sodium salt.
Figure 32:
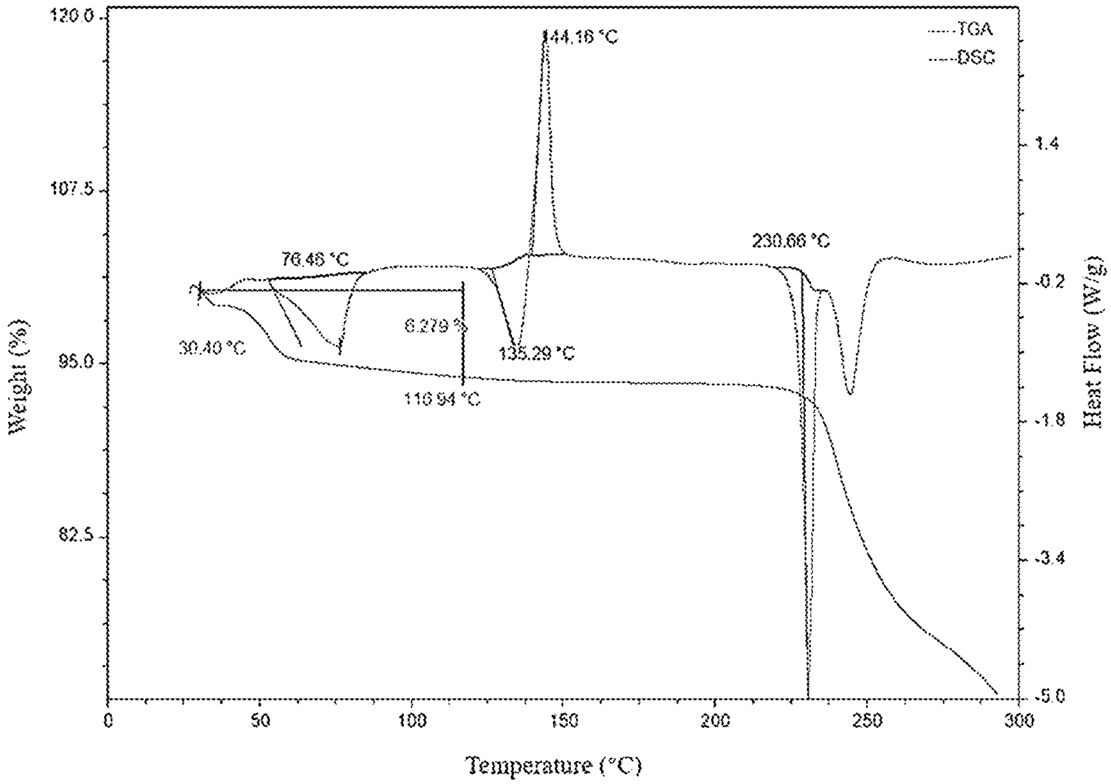
FIG. 32 shows the differential scanning calorimetry and thermal gravimetric analysis pattern of crystal form A of the sodium salt.
Figure 33:
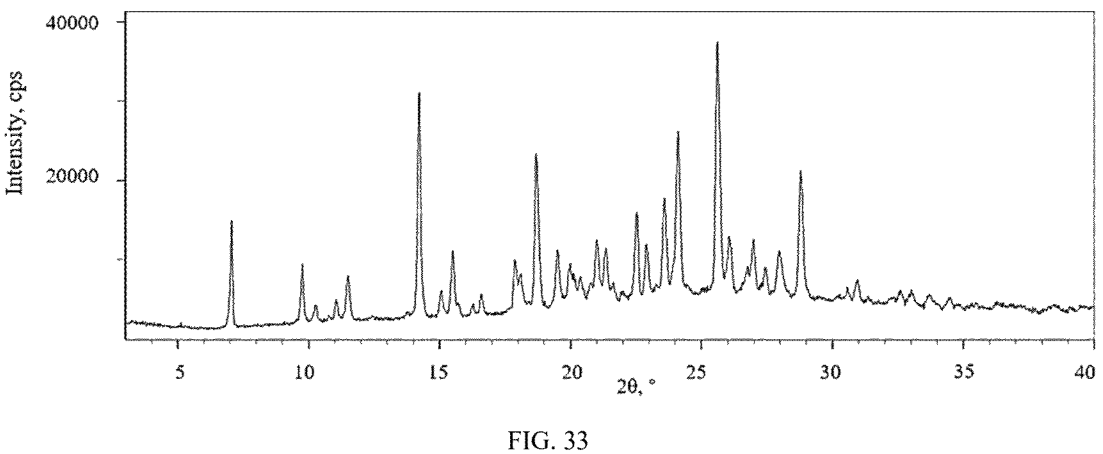
FIG. 33 shows the X-ray powder diffraction pattern of crystal form A of the potassium salt.
Figure 34:
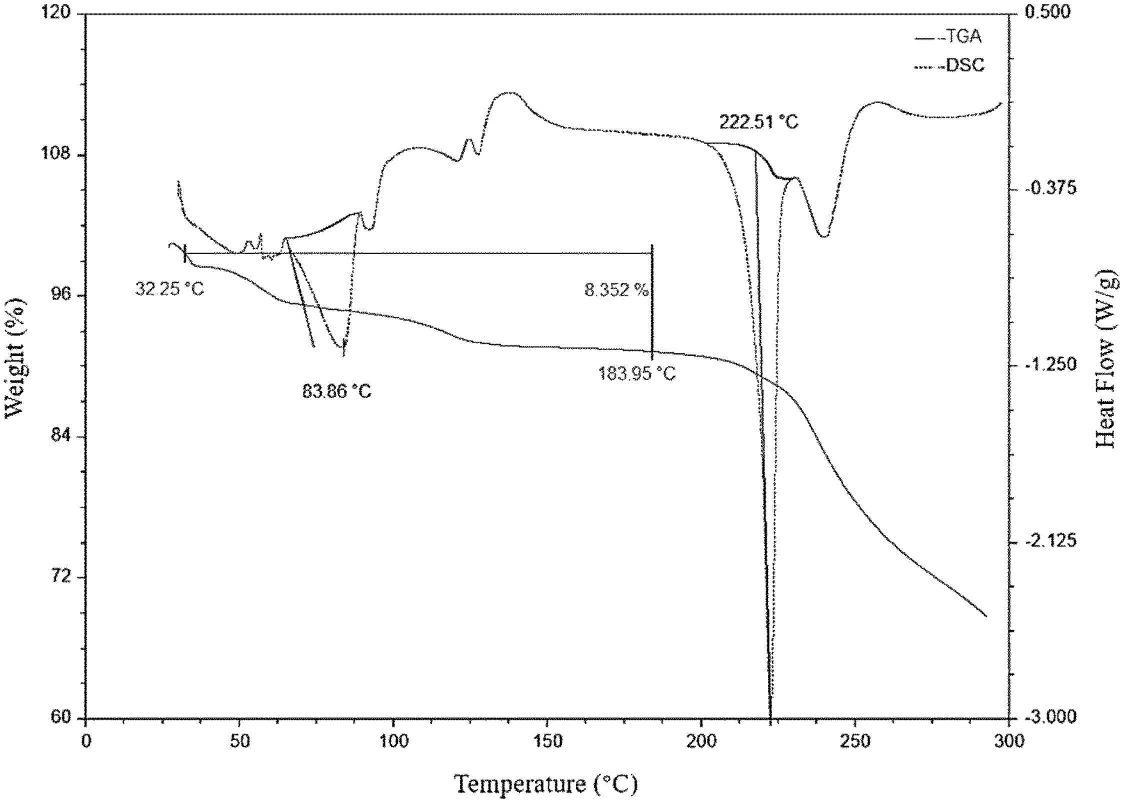
FIG. 34 shows the differential scanning calorimetry and thermal gravimetric analysis pattern of crystal form A of the potassium salt.

13. The salt according to claim 8, wherein the crystal form A of the hydrochloride salt satisfies one or more of the following conditions:

(1) the crystal form A of the hydrochloride salt has a thermal gravimetric analysis and differential scanning calorimetry pattern substantially as shown in FIG. 18;

(2) the crystal form A of the hydrochloride salt has an X-ray powder diffraction (XRPD) pattern substantially as shown in FIG. 17;

the crystal form B of the hydrochloride salt satisfies one or more of the following conditions:

(1) the crystal form B of the hydrochloride salt has an X-ray powder diffraction (XRPD) pattern substantially as shown in FIG. 19;

(2) the crystal form B of the hydrochloride salt has a thermal gravimetric analysis and differential scanning calorimetry pattern substantially as shown in FIG. 20;

the crystal form A of the sulfate salt satisfies one or more of the following conditions:

(1) the crystal form A of the sulfate salt has an X-ray powder diffraction (XRPD) pattern substantially as shown in FIG. 21;

(2) the crystal form A of the sulfate salt has a thermal gravimetric analysis and differential scanning calorimetry pattern substantially as shown in FIG. 22;

the crystal form B of the sulfate salt satisfies one or more of the following conditions:

(1) the crystal form B of the sulfate salt has an X-ray powder diffraction (XRPD) pattern substantially as shown in FIG. 23;

(2) the crystal form B of the sulfate salt has a thermal gravimetric analysis and differential scanning calorimetry pattern substantially as shown in FIG. 24;

the crystal form C of the sulfate salt satisfies one or more of the following conditions:

(1) the crystal form C of the sulfate salt has an X-ray powder diffraction (XRPD) pattern substantially as shown in FIG. 25;

(2) the crystal form C of the sulfate salt has a thermal gravimetric analysis and differential scanning calorimetry pattern substantially as shown in FIG. 26;

the crystal form A of the phosphate salt satisfies one or more of the following conditions:

(1) the crystal form A of the phosphate salt has an X-ray powder diffraction (XRPD) pattern substantially as shown in FIG. 27;

(2) the crystal form A of the phosphate salt has a thermal gravimetric analysis and differential scanning calorimetry pattern substantially as shown in FIG. 28;

the crystal form B of the phosphate salt satisfies one or more of the following conditions:

(1) the crystal form B of the phosphate salt has an X-ray powder diffraction (XRPD) pattern substantially as shown in FIG. 29;

(2) the crystal form B of the phosphate salt has a thermal gravimetric analysis and differential scanning calorimetry pattern substantially as shown in FIG. 30;

the crystal form A of the sodium salt satisfies one or more of the following conditions:

(1) the crystal form A of the sodium salt has an X-ray powder diffraction (XRPD) pattern substantially as shown in FIG. 31;

(2) the crystal form A of the sodium salt has a thermal gravimetric analysis and differential scanning calorimetry pattern substantially as shown in FIG. 32;

the crystal form A of the potassium salt satisfies one or more of the following conditions:

(1) the crystal form A of the potassium salt has an X-ray powder diffraction (XRPD) pattern substantially as shown in FIG. 33;

(2) the crystal form A of the potassium salt has a thermal gravimetric analysis and differential scanning calorimetry pattern substantially as shown in FIG. 34.

14. A pharmaceutical composition, comprising the crystal form of the five-membered-fused six-membered compound represented by formula I according to claim 1, and a pharmaceutical excipient.

15. A pharmaceutical composition, comprising the crystal form of the salt of a five-membered-fused six-membered compound represented by formula I according to claim 8, and a pharmaceutical excipient.

16. A method for inhibiting FLT3 and/or IRAK4 activity comprising administering to a patient an effective amount of the crystal form of the five-membered-fused six-membered compound represented by formula I according to claim 1; wherein diseases treatable by such inhibition are selected from one or more of hematological tumors, solid tumors, autoimmune diseases, inflammatory diseases, cardiovascular diseases, cancer, and central nervous system diseases.

17. A method for inhibiting FLT3 and/or IRAK4 activity comprising administering to a patient an effective amount of the crystal form of the salt of a five-membered-fused six-membered compound represented by formula I according to claim 8; wherein diseases treatable by such inhibition are selected from one or more of hematological tumors, solid tumors, autoimmune diseases, inflammatory diseases, cardiovascular diseases, cancer, and central nervous system diseases.

18. A preparation method for the crystal form of the five-membered-fused six-membered compound represented by formula I according to claim 1, wherein the preparation method for the crystal form A comprises the following steps: adding a poor solvent to a solution of the five-membered-fused six-membered compound represented by formula I, and cooling to crystallize to obtain the crystal form A;

the preparation method for the crystal form C comprises the following steps: volatilizing a suspension of the five-membered-fused six-membered compound represented by formula I to obtain the crystal form C;

when the crystal form is crystal form G, the preparation method comprises the following operation: cooling a solution of the five-membered-fused six-membered compound represented by formula I to obtain the crystal form; wherein the solvent of the solution is an alcohol solvent.

19. The preparation method according to claim 18, satisfying one or more of the following conditions:

(1) in the preparation method for crystal form A, the solvent for the solution of the five-membered-fused six-membered compound represented by formula I is a mixed solvent of a sulfoxide solvent and an alcohol solvent;

(2) in the preparation method for crystal form A, the poor solvent is an alcohol solvent and/or water;

(3) in the preparation method for crystal form A, in the solution of the five-membered-fused six-membered compound represented by formula I, the mass-to-volume ratio of the five-membered-fused six-membered compound represented by formula I to the solvent of the solution of the five-membered-fused six-membered compound represented by formula I is 1:(1-10) g/mL;

(4) in the preparation method for crystal form A, the volume ratio of the solution of the five-membered-fused six-membered compound represented by formula I to the poor solvent is (1-10):18.3;

(5) in the preparation method for crystal form A, the temperature for adding the poor solvent is 20 to 65° C.;

(6) in the preparation method for crystal form A, the temperature for cooling the solution is 30 to 70° C.;

(7) in the preparation method for crystal form A, the rate for cooling is 5 to 15° C./hour;

(8) in the preparation method for crystal form A, the time for cooling is 10 to 30 hours;

(9) in the preparation method for crystal form C, the solvent for the suspension is a mixture of an organic solvent and water;

(10) in the preparation method for crystal form C, the mass-to-volume ratio of the five-membered-fused six-membered compound represented by formula I to the solvent in the suspension is (10-100):1 mg/mL;

(11) in the preparation method for crystal form C, the temperature for volatilizing is room temperature;

(12) n the preparation method for crystal form C, the time for volatilizing is 1 to 5 days;

(13) in the preparation method for crystal form G, the alcohol solvent is methanol;

(14) in the preparation method for crystal form G, the mass-to-volume ratio of the five-membered-fused six-membered compound represented by formula I to the alcohol solvent is (10-100):1 mg/mL;

(15) in the preparation method for crystal form G, the temperature of the solution is 30 to 70° C.;

(16) in the preparation method for crystal form G, the rate for cooling is 3 to 10° C./hour;

(17) in the preparation method for crystal form G, the time for cooling is 1 to 20 hours.

20. A compound represented by formula II-49-3,

II-49-3

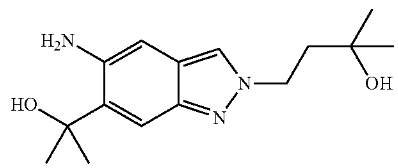

* * * * *